United States Patent [19]

Hwang et al.

[11] Patent Number: 5,770,383

[45] Date of Patent: Jun. 23, 1998

[54] TRICYCLIC RETINOIDS, METHODS FOR THEIR PRODUCTION AND USE

[75] Inventors: Chan Kou Hwang, Boulder, Colo.; Steven K. White, San Diego, Calif.; Youssef L. Bennani, La Jolla, Calif.; Stacie S. Canan Koch; Beth Ann Badea, both of San Diego, Calif.; Jonathan J. Hebert, Mission Viejo, Calif.; Luc J. Farmer, La Jolla, Calif.; Alex M. Nadzan, San Diego, Calif.

[73] Assignee: Ligand Pharmaceuticals, Inc., San Diego, Calif.

[21] Appl. No.: 475,397

[22] Filed: Jun. 7, 1995

Related U.S. Application Data

[63] Continuation-in-part of Ser. No. 366,630, Nov. 9, 1994, abandoned.

[51] Int. Cl.$^6$ .................. G01N 33/53; C07D 221/06; A61K 31/33; C07K 1/14
[52] U.S. Cl. .................. 435/7.1; 514/217; 514/290; 514/454; 514/570; 514/569; 530/350; 530/369; 530/412; 540/586; 546/101; 549/388; 560/8; 562/405
[58] Field of Search ................ 540/586; 546/101; 549/388; 560/8; 565/405; 514/217, 290, 454, 510, 569; 435/7.1; 530/350, 369, 412

[56] References Cited

U.S. PATENT DOCUMENTS

| | | | |
|---|---|---|---|
| Re. 33,533 | 2/1991 | Shroot et al. | 514/23 |
| 4,831,052 | 5/1989 | Shudo | 514/455 |
| 4,925,979 | 5/1990 | Shudo | 562/462 |
| 5,004,730 | 4/1991 | Philippe et al. | 514/29 |
| 5,124,473 | 6/1992 | Shroot et al. | 560/56 |
| 5,196,577 | 3/1993 | Shroot et al. | 562/490 |
| 5,455,265 | 10/1995 | Chandraratna | 514/448 |
| 5,585,244 | 12/1996 | Allegretto et al. | 435/7.1 |
| 5,668,175 | 9/1997 | Evans et al. | 514/569 |
| 5,675,033 | 10/1997 | Vuligonda et al. | 560/100 |
| 5,721,103 | 2/1998 | Boehm et al. | 435/7.1 |

OTHER PUBLICATIONS

Dawson, M., et al., "Effect of Structural Modifications in the C7–C11 Region of the Retinoid Skeleton on Biological Activity in a Series of Aromatic Retinoids," *J. Med. Chem.*, 32:1504–1517 (1989).

Kagechika, H., et al., "Retinobenzoic Acids. 2. Structure–Activity Relationships of Chalcone–4–carboxylic Acids and Flavone–4–carboxylic Acids," *J. Med. Chem.*, 32:834–840 (1989).

Kagechika, H., et al., "Retinobenzoic Acids. 3. Structure–Activity Relationships of Retinoidal Azobenzene–4–carboxylic Acids and Stilbene–4–carboxylic Acids," *J. Med. Chem.*, 32:1098–1108 (1989).

Kagechika, H., et al., "Retinobenzoic Acids. 4. Conformation of Aromatic Amides with Retinoidal Activity. Importance of *trans*–Amide Structure for the Activity," *J. Med. Chem.*, 32:2292–2296 (1989).

*Primary Examiner*—Ponnathapura Achutamurthy
*Attorney, Agent, or Firm*—William L. Respess; J. Scott Elmer

[57] ABSTRACT

Tricyclic retinoids having activity for retinoic acid receptors and/or retinoid X receptors are provided. Also provided are pharmaceutical compositions incorporating such tricyclic retinoid compounds and methods for their therapeutic use.

39 Claims, No Drawings

TRICYCLIC RETINOIDS, METHODS FOR THEIR PRODUCTION AND USE

REFERENCE TO RELATED APPLICATIONS

This application is a Continuation-In-Part application of U.S. patent application Ser. No. 08/366,630, filed Dec. 30, 1994, now abandoned, the entire disclosure of which is herein incorporated by reference.

FIELD OF THE INVENTION

The present invention relates to compounds having activity for retinioic acid receptors and retinoid X receptors, and to methods for the production and therapeutic use of such compounds.

BACKGROUND OF THE INVENTION

The vitamin A mietabolite, retinoic acid, has long been recognized to induce a broad spectrum of biological effects. In addition, a variety of structural analogues of retinoic acid have been synthesized that also have been found to be bioactive. Some, such as Retin-A® and Accutaneol®, have found utility as therapeutic agents for the treatment of various pathological conditions. In addition, synthetic retinoids have been found to mimic many of the pharmacological actions of retinoic acid.

Medical professionals have become very interested in the therapeutic applications of retinoids. Among their uses approved by the FDA is the treatment of severe forms of acne and psoriasis. A large body of evidence also exists that these compounds can be used to arrest alid, to an extent, reverse the effects of skin damage arising from prolonged exposure to the sun. Other evidence exists that these compounds may be useful in the treatment and prevention of a variety of cancerous and pre-cancerous conditions, such as melanoma, cervical cancer, some forms of leukemia, oral leukoplakia and basal and squamous cell carcinomas. Retilloids have also shown an ability to be efficacious in treating and preventing diseases of the eye, caiirdiovascular system, immune system, skin, respiratory and digestive tracts, andl as agents to facilitate wound healing and modulate programmed cell death (apoptosis).

Major insight into the molecular mechanism of retinoic acid signal transduction was gained in 1988, when a member of the steroid/thyroid hormone intracellular receptor superfamily was shown to transduce a retinoic acid signal. Evans, *Science*, 240:889–95 (1988); Giguere et al., *Nature*, 330:624–29 (1987); Petkovich etail., *Nature*, 330: 444–50 (1987). It is now known that retinoids regulate the activity of two distinct intracellular receptor suhfamililies; the Retinoic Acid Receptors (RARs) and the Retinoid X Receptors (RXRs), including their isoforms, RARα, β, γ and RXRα, β, γ. In this regard, an endogenous low-iliolecuilar-weight liganid which modulates the transcriptional activity of the RARs is all-traiiis-retinoic acid (ATRA), while all endogenious ligand for the RXRs is 9-cis retinoic acid (9-cis). Heyman el al., *Cell*, 68:397–406 (1992) and Levin et al. *Nature*, 355:359–61 (1992).

Although both the RARs and RXRs respond to ATRA in vivo, due to the ill i,ivo conversion of some of the ATRA to 9-cis, the receptors differ in several important aspects. First, the RARα and RXRα are significantly divergent in primary structure (e.g., the ligand binding domains of RARα and RXRα have only 27% amino acid identity). These structural differences are reflected in the different relative degrees of responsiveness of RARs and RXRs to various vitamin A metabolites and synthetic retinoids. In addition, distinctly different patterns of tissue distribution are seen for RARs and RXRs. For example, in contrast to the RARs, which are not expressed at high levels in the visceral tissues, RXRα mRNA has been shown to be most abundant in the liver, kidney, lung, muscle and intestine. Finally, the RARs and RXRs have different target gene specificity. For example, response elements have recently been identified in the cellular retinal binding protein type 11 (CRBPII) and Apolipoprotein Al genes which confer responsiveness to RXR, but not RAR. Furthermore, RAR has also been recently shown to repress RXR-mediated activation through the CRBPII RXR response clement (Manglesdorf et al., *Cell*, 66:555–61 (1991)). These data indicate that two retinioic acid responsive pathways are not simply redundant, but instead manifest a complex interplay.

In view of the related, but clearly distinct, nature of these receptors, retinoids which are more selective for the RAR subfamily or the RXR subfamily would be of great value for selectively controlling processes mediated by one or more of the RAR or RXR isoforms, and would provide the capacity for independent control of the physiologic processes mediated by the RARs or RXRs. In addition, pan-agonist retinoids that activate one or more isoforms of both the RARs and RXRs would also be valuable for controlling processes mediated by both of these subfamilies of retinoid receptors. Furthermore, retinoids which preferentially affect one or more but not all of the receptor isoforms also ofler the possibility of increased therapeutic efficacy and reduced side effect profiles when used for therapeutic applications.

Various tricyclic compounds, the majority of which are beta-stibstitulted on the C ring in,, have been disclosed to have retinoid activity, including those compounds disclosed in H. Kagechika et al., "Retinobenzoic Acids. 2. Structure-Activity Relationship of Chalcone-4-30 carboxylic Acids and Flavone-4'-carboxylic Acids", 32 J. *Med. Chem.*, 834 (1989); H. Kagechika et al., "Retinobenzoic Acids. 3. Stiucture-Activity Relationships of Retinoidal Azobenzene-4-carboxylic Acids and Stilbene-4-carboxylic Acids", 32 J. *Med. Chem.*, 1098 (1989); H. Kagechika et al., "Retinobenzoic Acids. 4. Confoormationi of Aromatic Amides with Retinoidal Activity. Importance of trans-Amide Structure for the Activity", 32 J. *Med. Chem.*, 35 2292 (1989); M. I. Dawson et al., "Effect of Structural Modifications in the C7–C11 Region of the Retinoid Skeleton on Biological Activity in a Series of Aromatic Retinoids", 32 J. *Med. Chem.*, 1504 (1989) and U.S. Pat. Nos. 4,831,052, 4,874, 747, 4,925,979, 5,004,730, 5,124,473 and Re 33,533.

SUMMARY OF THE INVENTION

The present invention provides novel tricyclic compounds that have selective retinoid activity on RARs and RXRs or pan-agonist activity on one or more of each of the RAR and RXR isoforms. The present invention also provides pharmaceutical compositions incorporating these novel tricyclic compounds and methods for the therapeutic use of such compounds and pharmaceutical compositions.

These and various other advantages and features of novelty which characterize the invention are pointed out with particularity in the claims annexed hereto and forming a part hereof. Ilowever, for a better understanding of the invention, its advantages, and(i objects obtained by its use, reference should be had to the accompanying drawings and descriptive matter, in which there is illustrated and described preferred embodiments of the invention.

Definitions

In accordance with the present invention and as used herein, the following terms are defined with the following meanings, unless explicitly stated otherwise.

The term alkyl refers to straight-chain, branched-chain or cyclic structures that are optionally saturated or unsaturated (thereby resulting in alkenyl and alkynyl struLctures), as well as combinations thereof.

The term aryl refers to an optionally substituted six-meinbered aromatic ring.

The term heteroaryl refers to an optionally substituted five-niembered or six-memiiber-ed heterocyclic ring containing one or more heteroatoms selected from the group consisting of oxygen, nitrogen and sulfur.

The terms retinoid or retinoids refer to compound(s) that bind and/or- activate one or more retinoid receptors, thereby affecting the transcriptional activity of a target genle to which the activated receptor and compound complex binds.

The term pan-agonist refers to a retinoid that activates at least one mmciibel of both the RAR subfamily (i.e., RARα, RARβ, or RARγ) and the RXR subfamily (i.e., RXRα, RXRβ, or RXRγ) Preferably such pan-agonist retinoids activate all members of both the RAR and RXR subfamilies of retinoid receptors.

DETAILED DESCRIPTION OF EMBODIMENTS OF THE INVENTION

In accordance with a first aspect of the present invention, we have developed tricyclic compounds of the formulae;

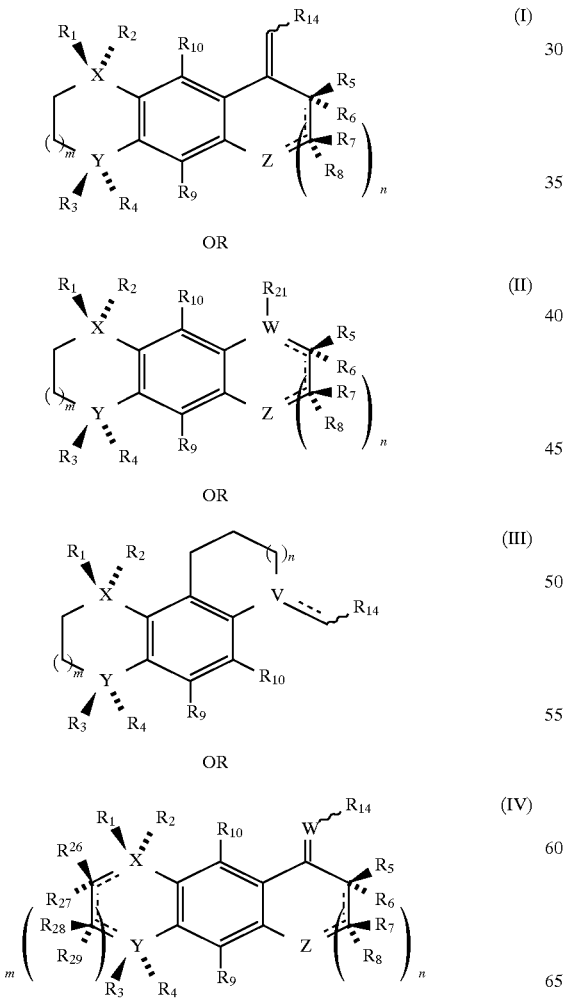

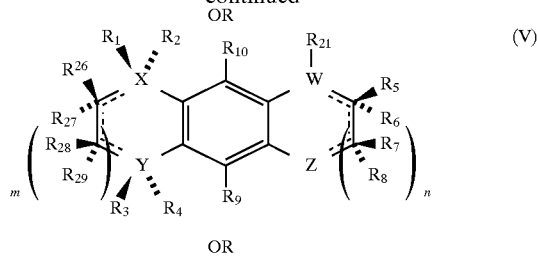

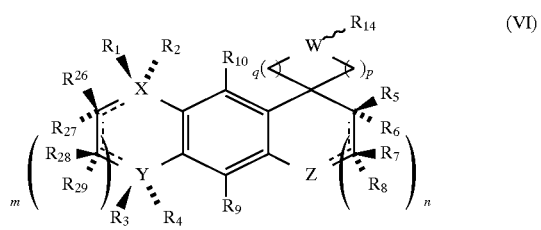

wherein, $R_1$ through $R_4$ each independently are hydrogen, a $C_1$–$C_6$ alkyl, or a $C_7$–$C_{15}$ arylalkyl;

$R_5$ through $R_8$ each independently are hydrogen, a $C_1$–$C_6$ alkyl, or at least two of $R_5$ through $R_8$ taken together are a $C_3$–$C_6$ cycloalkyl;

$R^9$ and $R^{10}$ each independently are hydrogen, a $C_1$–$C_6$ alkyl, F, Cl, Br, $NR_{11}R_{12}$, $NO_2$ or $OR_{13}$, where $R_{11}$ and $R_{12}$ each independently are hydrogen, a $C_1$–$C_8$ alkyl, a $C_7$–$C_{15}$ arylalkyl, a $C_1$–$C_8$ acyl, provided that only one $R_{11}$ or $R_{12}$ can be acyl, or $R_{11}$ and $R_{12}$ taken together are a $C_3$–$C_6$ cycloalkyl, and where $R_{13}$ is hydrogen or a $C_1$–$C_8$ alkyl or a $C_7$–$C_{15}$ arylalkyl;

$R_{14}$ represents:

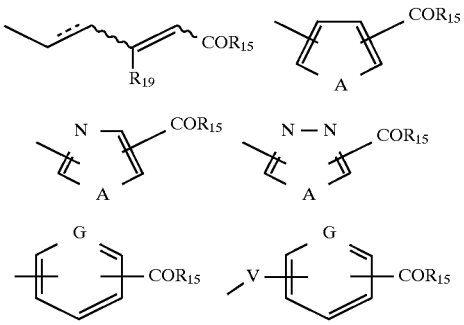

where $R_{15}$ is $OR_{16}$ or $NR_{17}R_{18}$, with $R_{16}$ being hydrogen, a $C_1$–$C_6$ alkyl or a $C_7$–$C_{15}$ arylalkyl, and with $R_{17}$ and $R_{18}$ each independently being hydrogen, a $C_1$–$C_6$ alkyl, a $C_7$–$C_{15}$ arylalkyl, aryl, ortho-, meta-, or para-substituted hydroxyaryl, or taken together are a $C_3$–$C_6$ cycloalkyl, provided that $R_{18}$ must be hydrogen when $R_{17}$ is aryl or hydroxyaryl, $R_{19}$ is a $C_1$–$C_5$ alkyl, and A is O, S or $NR_{20}$, where $R_{20}$ is a hydrogen, $C_1$–$C_6$ alkyl or a $C_7$–$C_{15}$ arylalky;

$R_{21}$, represents:

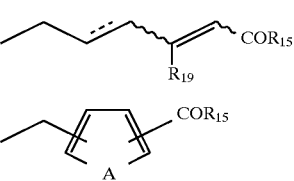

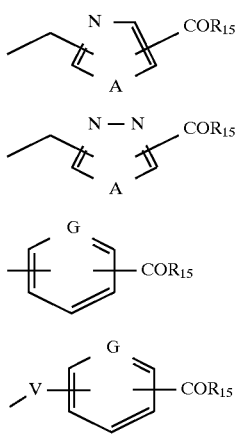

where $R_{15}$, $R_{19}$, and A have the same definitions given above;

$R_{26}$ through $R_{29}$ each independently are hydrogen or a $C_1$–$C_6$ alkyl, or taken together then one each of $R_{26}$ and $R_{27}$ or $R_{28}$ and $R_{29}$ respectively, form a car-boniyl group;

X and Y each independently represent C, O, S, N, SO or $SO_2$, provided, however, that when X or Y are O, S, SO or $SO_2$, then either $R_1$ and $R_2$ or $R_3$ and $R_4$ respectively do not exist, and further provided, that when X or Y is N, then one each of $R_1$ and $R_2$ or $R_3$ and $R_4$ respectively, do not exist;

Z is O, S, $CR_{22}R_{23}$ or $NR_{24}$, where $R_{22}$ through $R_{24}$ each independently are hydrogen or a $C_1$–$C_6$ alkyl or $R_{22}$ and $R_{23}$ taken together are a $C_3$–$C_6$ cycloalkyl;

W is N or $CR_{25}$, where $R_{25}$ is hydrogen or a $C_1$–$C_6$ alkyl;

V is C or N, provided, however, that when V is N, then no double bond exists adjitcenit to V;

G is C or N, provided G cannot be C when W is C;

m is 0 or 1 carbon atoms;

n is 0, 1 or 2 carbon atoms;

q is 1 or 2 carbon atoms;

p is 0, 1 or 2 carbon atoms;

the dashed lines in the structures represent optional double bonds, piovided, however, that the double bonds cannot be contiguous, and further provided that when such optional double bonds exist then one each of $R_5$ and $R_6$ or $R_7$ and $R_8$ respectively do not exist; anld the wavy lines represent olefin bonds that are either in the cis (Z) or trans (F) configuration.

The compounds of the present invention also include all phairma,cetitically acceptable salts, as well as esters, amides and prodr-Ligs. Preferably, such salts, esters and amides, will be formed at the $R_{15}$ and $R_{16}$ positions. As used in this disclosure, pharmaceutically acceptable salts include, but are not limited to: pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamilo, and tris(hydoxymethyl) aminomethane. Additional pharmaceutically acceptable salts aIre known to those skilled in the art.

The compounds of the present invention exhibit retinoid activity and are particularly useful in the treatment of skin-related diseases, including, without limitation, actinic keratoses, arsenic keratoses, inflammatory and non-inflammatory acne, psoriasis, ichithyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin pigmentation agents and to treat and reverse the effects of age and photo damage to the skin. The compounds are also useful for the prevention anid treatment of cancerous and pre-cancerous conditions, including, premalignant and malignant hyperproliferative diseases such as cancers of the breast, skin, prostate, cervix, uterus, COOln, bladder, esophagus, stomach, lung, larynx, oral cavity, blood and lymphatic system, metaplasias, dysplasias, neoplasias, leukoplakias and papillomas of the mucous membranes and in the treatment of Kaposis sarcoma. In addition, the present compounds can be used as agents to treat diseases of the eye, including, without limitation, proliferative vitreoretinopaithy (PVR), retinal detachment, dry eye and other corneopathies, as well as in the treatment and prevention of various cardiovascular diseases, including, without limitation, diseases associated with lipid metabolism such as dyslipidemias, prevention of restenosis and as all agent to increase the level of circulating tissue plasminogen activator (TPA). Other uses for the compounds of the present invention include the prevention and treatment of conditions and diseases aissociated with human papilloma virus (HPV), including warts and genital warts, various inflammatory diseases such is pulmonary fibrosis, ileitis, colitis and Krohn's disease, neurodegenerative diseases such as Alzheimer's disease, Parkinson's disease and Amyotrophic lateral Sclerosis (AL.S), improper pituitary function, including insufficient production of growth hormone, modulation of apoptosis, including both the induction of apoptosis and inhibition of apoptosis via the Fas and Fas-Ligand pathway, including inhibition of T-Cell activated apoptosis, restoration ol hair growth, including combination therapies with the present compounds and other agents such as Minoxidil®, diseases associated with the immune system, including use of the present compounds as immunosuppressaints and irninunostimulanits, modulation of organ trausplant rejection and facilitation of wound healing, including modulation of chelosis. It will also be underst)od by those skilled in the art that the retinoid compounds of the present invention will prove useful in any therapy in which retinoids, including RAR selective retinoids, RXR selective retinoids, and panagonist retinoids will find application.

Furthermore, it will be understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other therapies, including, without limitation, chemotherapeutic agents such as cytostatic and cytotoxic agents, immunological modifiers such as interferons, hitelrleukins, growth hormones and other cytokines, hormone therapies, surgery and radiation therapy.

Representative compounds of the present invention include, without limitation, ethyl (2E,4E)-3-methyl-6-[(Z)-3,4,5,6,7,8-hexahydro-5,5,8,8-tetramethyl-2H-anthracen-1-ylidene ]hexa-2,4-dienoate; (2E,4E)-3-methyl-6[(Z)-3,4,5,6,7,8-hexahydro-5,5,8,8-tetramethyl-2H-anthracen-1-ylidene] hexa-2,4-dienoic acid; ethyl (2E,4E)-3-methyl-6-[(Z)-2,3-5,6,7,8-hexahydro-5,5,8,8-tetramethylcyclopenta[b] napthalen-1-ylidene]hexa-2,4-dienoate; (2E,4E)-3-methyl-6-[(Z)-2,3-5,6,7,8-hexahydro-5,5,8,8,-tetramiethyl-cyclopenta[b]naplitlalein-1-ylidene]hexa-2,4-dienoic acid;

ethyl (2E,4E)-3-methyl-6-[(Z)-1,2,3,6,7,8-hexahydro-1,1,3, 3-tetramethylcycopenta[b]naphthalen-5-ylidene]hexa-2,4-dienoate; (2E,4E)-3-menthyl-6-[(Z)-1,2,3,6,7,8-hexahydro-, 1,1,3,3-tetra-cyclopenta[b]naphthatei-5-ylidene]hex,2,4-dienoc acid; (2E,4E)-3-methyl-6-(2,3,6,7,8,9-hexahydro-2, 2,6,6,9,9-hexamethylbenzo[b]-chromen-4-ylidene)hexa-2, 4-dienoic acid; ethyl (2E,4E)-3-methyl-6-[(Z)-3,4,5,6,7,8-hexahydro-10-nitro-5,5,8,8-tetramethyl-2H-anthracen-1-ylidene]hexa-2,4-dienoate; (2E,4E)-3-methyl-6-[(Z)-3,4,5, 6,7,8-hexahydro-10-nitro-5,5,8,8-tetramethyl-2H-anthracen-1-ylidene]hexa-2,4-dienoic acid; ethyl (2E,4E)-3-methyl-6-[(Z)-3,4,5,6,7,8-hexahydro-4,4,5,5,8,8-hexametyl-2H-anthracen-1-ylidene]hexa-2,4-dienoate; (2E, 4E)-3-methyl-6-[(Z)-3,4,5,6,7,8-hexahydro-4,4,5,5,8,8-hexamethyl-2H-anthracen-1-ylidene]hexa-2,4-dienoic acid; (2E,4E)-3-methlyl-6-[(Z)-2,3,5,6,7,8-hexahydro-3,5,5,8,8-pentamethyl-cyclopenta[b]naphthalen-1-ylidene]hexa-2,4,-dienoic acid; (2E,4E)-3-methyl-6-[(Z)-3,5,6,7-tetrahydro-5, 5,7,7-tetramethyl-2H-5-indacen-1-ylidene]hexa-2,4-dienoic acid; ethyl (2E,4E)-3-methyl-6-[(E)-3,4,5,6,7,8-hexahydro-5,5,8,8-tetramethyl-2H-anthracen-1-ylidene]hexa-2,4-dienoate; (2E,4E)-3-methyl-6-[(E)-3,4,5,6,7,8-hexahydro-5, 5,8,8-tetramethyl-2H-anthracen-1-ylidene]hexa-2,4-dielnoic acid; ethyl (2E,4E)-3-methyl-6[(E)-2,3,5,6,7,8-hexahydro-5,5,8,8-tetramethylcyclopenta[b]naphthalen-1-ylidene]hexa-2,4-dienoate; (2E,4E)-3methyl-6-[(E)-2,3,5,6, 7,8-hexahydro-5,5,8,8-tetrametiylcyclopenta[b]naphthalen-1-ylidene]hexa-2,4-dienoic acid; ethyl(2E,4E)-3-methyl-6-[(E)-1,2,3,6,7,8-hexahydro-1,1,3,3-tetramethylcyclopenta[b]naphthalen-5-ylidene]hexa-2,4-dieiioate; (2E,4E)-3-methyl-6-[(E)-1,2,3,6,7,8-hexahydro-1,1,3,3-tetramethylcyclopenta[b]-5-ylidene]hexa-2,4-dienoic acid; ethyl (2Z,4E)-3-methyl-6-[(E)-1 2,3,6,7,8-hexahydro-1,1,3, 3-tetramethylcyclopenta[b]naphthalen-5-ylidene]hexa-2,4-dienoate; (2Z,4E)-3-methyl-6-[(E)-1,2,3,6,7,8-hexthydo-1, 1,3,3-tetramethylcyclopenta[b]naphthalen-5-ylidene]hexa-2,4-dienoic acid; (2E,4E)-3-methyl-6-(E)-[4,4,6,6,9,9-hexamethyl-1,2,3,4,5,6,7,8-octahydroanthracen-1-ylidene] hexa-2,4-(dienoic acid; ethyl (2E,4E,6E)-3-methyl-6-[1,2,3, 4,7,8,9,10-octahydro-1,1,4,4-tetramethyl-6H-naphthocycloheptene-10-yl]hexa-2,4,6-trienoate; ethyl (2E, 4E,6E)-3-methyl-6-[1,2,3,4,7,8,9,10-octahydro-1,1,4,4-tetramethyl-6H-naphthocycloheptene-10-yl]hexa-2,4,6-trienoate; ethyl (2Z,4E,6E)-3-methyl-6-[1,2,3,4,7,8,9,10-octahydro-1,1,4,4-tetrarnethyl-6H-naphthocycloheptene-10-yl]hexa-2,4,6-trienoate; (2Z,4E,6E)-3-methyl-6-[1,2,3,4, 7,8,9,10-octahydro-1,1,4,4-tetramethyl-6H-naphthocycloheptene-10-yl]hexa-2,4,6-trienoic acid; (2E, 4E)-3-methyl -6-[(E)-3,5,6,7-tetrahydro-5,5,7,7-tetramethyl-2H-5-indacen-1-ylidene]hexa-2,4-dienoic acid; ethyl (2E,4E)-3-methyl-6-[(E)-3,4,5,6,7,8-hexahydro-10-nitro-5,5,8,8-tetramethyl-2H-anthracen-1-ylidene]hexa-2,4-dienoate; (2E,4E)-3-methyl -6-[(E)-53,4,5,6,7,8-hexahydro-10-nitro-5,5,8,8-tetramethyl-2H-anthracen-1-ylidene]hexa-2,4-dienoic acid; (2Z,4E)-3-methyl-6-[(E)-3,4,5,6,7,8-hexahydro-10-nitro-5,5,8,8-tetramethyl-2H-anthracen-1-ylidene]hexa-2,4-dienoic acid; (2E,4E)-3-methyl-6-[(E) 2,3, 6,7,8,9-hexahydro-6,6,9,9-tetramethylbenzo[g]chromnen-4-ylidene]hexa-2,4-dienoic acid; (2Z,4E)-3-methyl-6-[(E)-2, 3,6,7,8,9-hexahydro-6,6,9,9-tetramethylbenzo[g]chromen-4-yliden]hexa-2,4-dienoic acid; (2E,4E)-3-methyl-6-[(E)-,3, 6,7,8,9-hexahydro-6,6,9,9-tetramethylbenzo[g]chromen-4-ylidene]hexa-2,4-dienoic acid; ethyl (2E,4E)-3-methyl-6-(3, 4,5,6,7,8-hexahydro-5,5,8,8-tetramethylanthracen-1-yl) hexa-2,4-dienoate; (2E,4E)-3-methyl-6-(3,4,5,6,7,8-hexahydro-5,5,8,8-tetramethylanthracen-1-yl)hexa-2,4-dienoic acid; (3E,5E)-3-methyl-6-(3,4,5,6,7,8-hexahydro-5, 5,8,8-tetramethylanthracen-1-yl)hexa-3,5-dienoic acid; ethyl (2E,4E)-3-methyl-6-(1,2,3,4,5,6,7,8-octahydro-5,5,8, 8-tetramethylanthracen-1-yl)hexa-2,4-dienoate; (2E,4E)-3-methyl-6-(1,2,3,4,5,6,7,8-octahydro-5,5,8,8-tetramethylanthracen-1-yl)hexa-2,4-dienoic acid; ethyl (2E,4E)-3-methyl-6-(1,2,3,5,6,7,8-heptahydro-5,5,8,8-tetramethylcyclopenta[b]napthalen-1-yl)hexa-2,4-dienoate; (2E,4E)-3-methyl-6-1,2,3(5,6,7,8-heptahydro-5,5,8,8-tetramethyl-cyclopenta[b]naphthalen-1-yl]hexa-2,4-dienoic acid; ethyl (2E,4E)-3-methyl-6-[1,2,3,4,7,8,9,10)-octahydro-1,1,4,4-tetramethyl-6H-naphthocycloheptan-10-yl]hexa-2,4-dienoate; (2E,4E)-3-methyl-6-[1,2,3,4,7,8,9,10-octahydro-1,1,4,4-tetramethyl-6H-naphthocycloheptan-10-yl]hexa-2,4-dienoic acid; ethyl (2Z,4E)-3-methyl-6-[1,2,3, 4,7,8,9,10-octahydro-1,1,4,4-tetramethyl-6H-naphthocycloheptan-10-yl]hexa-2,4-dienoate; (2Z,4E)-3-methyl-6-[1,2,3,4,7,8,9,10-octahydro-1,1,4,4-tetramethyl-6H-naphthocycloheptan-10-yl]hexa-2,4-dienoic acid; (2Z, 4E)-3-methyl-6-[1,2,3,4,7,8,9,10-octahydro-1,1,4,4-tetramethyl-6H-naphthocycloheptan-10-yl]hexa-2,4-dienoic acid; (2Z,4E)-3-methyl-6-[5,6,7,8-tetrahydro-5,5,8, 8-tetramethylnaphthyl-(2,3-b)-2,2-dimethylpyran-4-yl] hexa-2,4-dienoic acid; (2E,4E)-3-methyl-6-[5,6,7,8-tetrahydro-5,5,8,8-tetramethylnaphthyl-(2,3-b)-pyran-4-yl] hexa-2,4-dienoic acid; (2Z,4E)-3-methyl-6-[5,6,7,8-tetrahydro-5,5,8,8-tetramethylnaphthyl-(2,3-b)-pyran-4-yl] hexa-2,4-dienoic acid; (+)-(2E,4E)-3-methyl-6-(1,2,3,4,5,6, 7,8-octahydro-5,5,8,8-tetramethylanthracen-1-yl)hexa-2,4-dienoic acid; (−)-(2E,4E)-3-methyl-6-(1,2,3,4,5,6,7,8-octahydro-5,5,8,8-tetramethylanthracen-1-yl)hexa-2,4-dienoic acid; methyl (2E)-3-methyl-6-(1,2,3,4,6,7,8,9-octahydro-6,6,9,9-tetramethylanthracen-1-yl)hex-2-enoate; (2E)-3-methyl-6-(1,2,3,4,6,7,8,9-octiliydr-6,6,9,9-tetramethylanthracen-1-yl)hex-2-enoic acid; (2E)-3-methyl-6-(1,2,3,4,6,7,8,9-octahydro-6,6,9,9-tetramethylanthracen-1-yl)hex-2-enoic acid; (2E,4E)-3-methyl-6-[(E)-2,3,6,7,8,9-hexahydro-6,6,9,9-tetramethyl-1H-cyclopenta[a] naphthalen-3-ylidene]hexa-2,4-dienoic acid; ethyl (2E,4E)-3-methyl-6-(2,3,6,7,8,9-hexahydro-6,6,9,9-tetramethyl-1H-cyclopenta[a]naphthalen-3-yl]hexa-2,4-dienoate; (2E,4E)-3-methyl-6-(2,3,6,7,8,9-hexahydro-6,6,9,9-tetramethyl-1H-cyclopenta[a]naphthalen-3-yl)hexa-2,4-dienoic acid; ethyl (2E,4E)-3-methyl-6-[(Z)-1,2,3,4,7,8,9-heptahydro-7,7,9,9-tetramethylcyclopenta[f]naphthalen-4-ylidene]hexa-2,4-dienoate; (2E,4E)-3-methyl-6-[(Z)-1,2,3,4,7,8,9-heptahydro-7,7,9,9-tetramethylcyclopenta[f]naphthalen-4-ylidene]hexa-2,4-dienoic acid; ethyl (2E,4E)-3-methyl-6-(7, 7,10,10-tetramethyl-2,3,4,5,7,8,9,10-octahydronaphtho]2,3-6]-azepinyl)hexa-2,4-dienoate; (2E,4E)-3-methyl-6-[7,7,10, 10-tetramethyl-2,3,4,5,7,8,9,10-octahydronaphtho[2,3-6] azepinyl)hexa-2,4-dienoic acid; ethyl 3-methyl-6-(3,4,6,7,8, 9-hexahydro-6,6,9,9-tetramethyl-2H-benzo[g]quinolin-1-yl)hexa-2,4-dienoate; (2E,4E)-3-methyl-6-[3,4,6,7,8,9-hexahydro-6,6,9,9-tetramethyl-2H-1-benzo[g]quinolin-1-yl]hexa-2,4-dienoic acid; ethyl (2E,4E)-3-methyl-6-oxo-6-[5,6,7,8-tetrahydro-5,5,8,8-tetramethyl(2,3naphthyl [b]piperidin-1-yl]hexa-2,4-dienoate; (2E,4E)-3-methyl-6-oxo-6-(3,4,6,7,8,9-hexahydro-6,6,9,9-tetramethyl-2H-benzo [g]quinolin-1-yl)hexa-2,4-dienoic acid; ethyl (2E,4E)-3-methyl-6-oxo-6-[(2,3,5,6,7,8-hexahydro-5,5,8,8-tetramethyl)benzo[f]indol-1-yl]hexa-2,4-dienoate; (2E,4E)-3-methyl-6-oxo-6-[(2,3,5,6,7,8-hexahydro-5,5,8,8-tetramethyl)benzo-[f]-indol-1-yl]hexa-2,4-dienoic acid; ethyl (2E,4E)-3-methyl-6-(2,3,5,6,7,8-hexahydro-5,5,8,8-tetramethylbenzo[f]indol-1-yl]-hexa-2,4-dienoate; (2E,4E)-3-methyl-6-(2,3,5,6,7,8-hexahydro-5,5,8,8-tetramethylbenzo[f]indol-1-yl]hexa-2,4-dienoic acid; ethyl (2E,4E)-3-methyl-6-(7,7,10,10-tetrahydro-5,5,8,8-tetramethyl)benzo[f]quinolin-4-yl)hexa-2,4-dienoate; (2E,4E)-3-methyl-6-(1,2,3,4,7,8,9,10-octahydro-7,7,10,10-tetramethylbenzo[f]quinolin-4-yl)hexa-2,4-dienoic acid; (2E,4E)-3-methyl-6-[(Z)-5,6,7,8-tetrahydro-5,5,8,8-tetramethylnaphthyl(2,3-b-pyran-4-ylidene]hexa-2,4-dienoic acid; (2E,4E)-3-methyl-6-[(E)-3,4,5,6,7,8-hexahydro-2,2,5,5,8,8-hexamethyl-2H-anthracen-1-ylidene]hexa-2,4-dienoic acid; Ethyl-(2E,4E)-3-methyl-6[(Z)-N-acetyl-3,4,5,6,7,8-hexahydro-10-amino-5,5,8,8-tetramethyl-2H-anthracen-1-ylidene]hexa-2,4-dienoate; (2E,4E)-3-methyl-6-[(Z)-N-acetyl-3,4,5,6,7,8-hexahydro-10-(amino-5,5,8,8-tetramethyl-2H-anthiacen-1-ylidene]hexa-2,4-dienoic acid; (2E,4E)-3-methyl-6-[(E)1-ethyl-6,6,9,9-tetramethyl-2,3,6,7,8,9-hexahydro-1H-benzo[g]qinolin-4-ylidene]hexa-2,4-dienoic acid; T-butyl-4-(5-carboxy-penta-2E-4E-dieneylidene)-6,6,9,9-tetramethyl-3,4,6,7,8,9-hexahydro-2H-benzo[g]quinolin-1-carboxylate; (2E,4E)-3-methyl-(6,6,9,9-tetramethyl-2,3,6,9-tetrahydronaphtho[2,3-b]-[1,4]oxazin-4-yl)-hexa-2,4-dienoic acid; (2E,4E)-3-methyl-6-oxo-6-(6,6,9,9-tetrahydro-2,3,6,9-tetrahydronaphtho[2,3-b][1,4]oxazin-4-yl)hexa-2,4-(dienoic acid; (2E,4E)-3-methyl-6-(6-ethyl-1,9,9-trimethyl-7-oxo-2,3,6,7,8,9-hexahydro-1H-pyrido]2,3-g]quinolin-4-ylidene)hexa-2,4-dienoic acid; E-4-[N'-(5,5,8,8-tetramethyl-3,4,5,6,7,8-hexahydro-2H-anthracen-1-ylidene)-hydrazino]benzoic acid; E-4-[N'-(6,6,9,9-tetramethyl-2,3,6,7,8,9-hexahydro-benzo[g]chromen-4-ylidene)-hydrazino] benzoic acid and (2E,4E)-3-mietiiyl-6-(6-ethyl-1,9,9-trimethyl-2,3,6,9-tetrahydro-1H-pyrido[2,3-g]quinolin-4-ylidene)hexa-2,4-dienoic acid.

The compounds of the present invention can be obtained by modification of the compounds disclosed or by a total synthesis approach, by techniques known to those skilled in the art. In this regard, the synthesis of the compounds of the present invention often follow established retinoid synthesis schemes and techniques as described in M. I. Dawson and W. H. Okamura, "Chemistry and Biology of Synthetic Retinoids", Chapters 3, 8, 14 and 16, CRC Press, Inc., Florida (1990); M. I. Dawson and P. D. Hobbs, *The Synthetic Chemisitry of Retinoids, In* Chapter 2: "The Retinoids, Biology, Chemistry and Medicine", M. B. Sporn et al., Eds. (2nd ed.), Raven Press, New York, New York, pp. 5–178 (1994); R. S. H. Liu and A. E. Asato, "Photochemistry and Synthesis of Stereoisomers of Vitamin A," 40 *Tetrahedron,* 1931 (1984); 43 *Cancer Res.,* 5268 (1983); 15 *Eitr. J. Med. Chem.,* 9 (1980); and U.S. Pat. Nos. 4,326,055 and 4,578,498, the disclosures of which are herein incorporated by reference. The sequence of steps of the general schemes of synthesizing the compounds of the present invention are shown below. In addition, more detailed and illustrative synthetic schemes for specific conipounds of the present invention will be found in the Examples included herein.

Scheme I

Synthesis of Compounds of Structure (I)

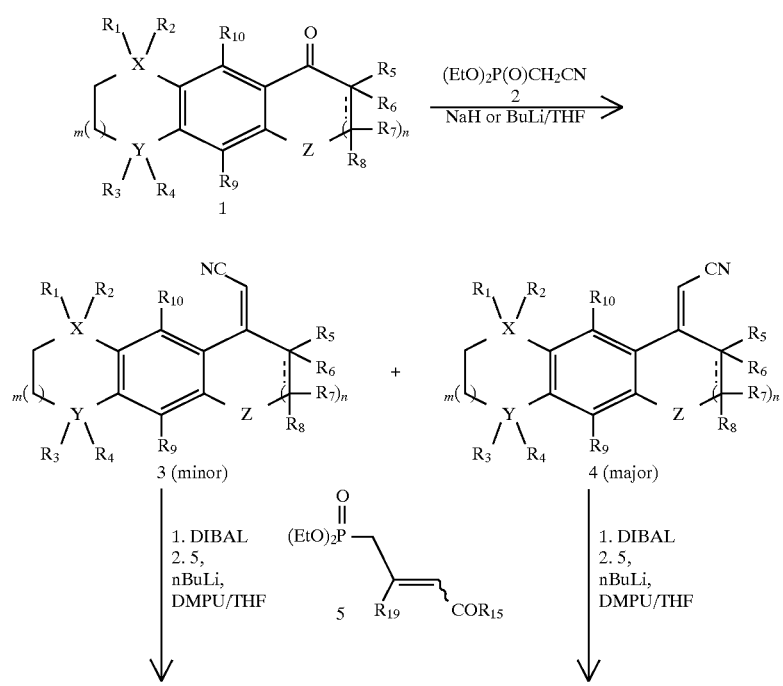

Scheme I
Synthesis of Compounds of Structure (I)

-continued

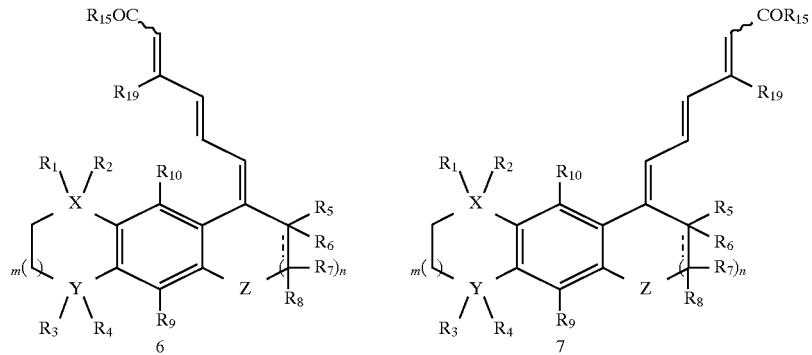

The tricyclic derivatives of the present invention, that is compounds of general structures 6 and 7, may be prepared in accordance with reaction Scheme I. The starting materials for this sequence, ketones of general structure 1, may be prepared from the appropriately substituted octahydroanthracene by oxidation with chromium trioxide in acetic acid at ambient temperature or with chromium trioxide in methylene chloride/pyridine at 0° C. Further, in accordance with this sequence of reactions tricyclic ketones of general structure I are condensed with the sodium or lithium salt of diethyl cyanomethylphosphonate in THF at reduced temperatures in a Homner-Wadsworth-Emmons olefination reaction to provide a mixture of the cis-cyano olefins 3 as the minor products and the tralis-cyano olefins 4 as the major products. The olefinic products may be separated by silica gel flash column chromatography.

The cis-cyano olefins 3 are reduced with DIBAL at −78° C. to give the intermediate enals. The solvent to be used in the reduction includes methylene chloride, hexanes, and THF. The product of the DIBAL reduction, the enal, is reacted with the lithium salt of diethyl 3-ethoxycarbonyl-2-methylprop-2-enylphosphonate (mixture of double bond isomers) in THF at reduced temperatures in a Horner-Wadsworth-Emmons olefination reaction to provide the tricyclic derivatives of general structure 6 where $R_{15}$ is ethyl. The oleflination reaction is preferably conducted in the presence of 1,3-dimethyl-3,4,5,6-tetrahydro-2(1H)-pyrimidinone (DMPU). The acids and salts derived from structure 6 are readily obtainable from the corresponding esters. The ethyl esters may be hydrolyzed in an alkanol solvent at amilbielit temperature with about a three molar excess of base, for example, potassium hydroxide. Alternatively, the ethyl esters may be hydrolyzed in THF/water or acetone/watel at ambient temperature with, for example, excess lithium hydroxide. The hydrolysis solution is acidified and the hydmolysate recovered by conventional means to give as the major product the (2E,4E)-Z-ylidene tricyclic carboxylic acid derivatives of structure 6 where $R_{15}$ is OH. The minor (2Z-4E)-Z-ylidene geometric isomers of general structure 6, by-products of the olefination reaction, are readily isolated by silica gel chromatography of the hydiolysite mixture.

In an analogous fashion, in accordance with reaction Scheme 1, the trans-cyano olefins 4 are transformed into the (2E,4E)-E-ylidene and (2Z, 4E)-E-ylildene tricyclic derivatives 7 where $R_{15}$ is ethoxy and OH.

Scheme II
Synthesis of Compounds of Structure (I)

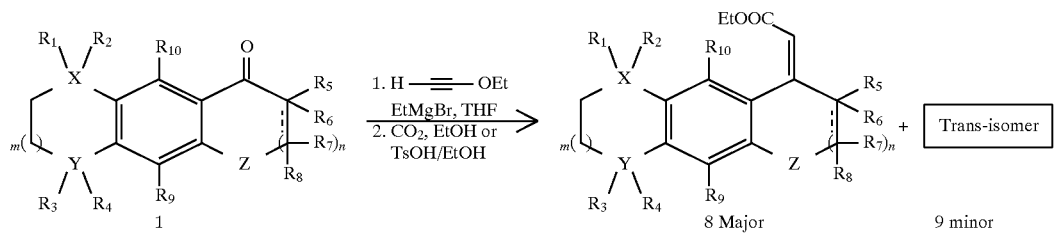

-continued
Scheme II
Synthesis of Compounds of Structure (I)

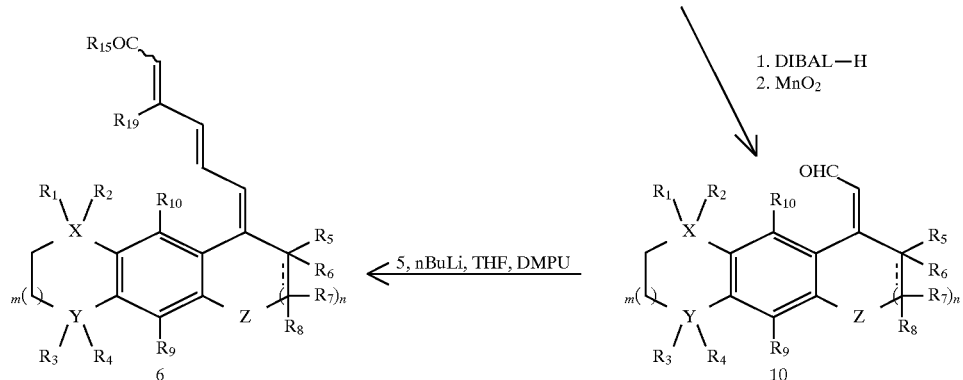

An alternative means for making the tricyclic derivatives of general structure 6 is ill accordance with reaction Scheme II. Tricyclic ketones 1 are treated with ethoxy ethynyl magnesium bromide in THF at 0° C. to ambient temperature. The resulting propairgylic alcohols are isolated by typical extractive means, dissolved in ethanol and treated with carbon dioxide (gas) or, alternatively, a catalytic amount of p-toluensulfonic acid and/or camphor sulfonic acid to provide a mixture of the cis-olefinic esters 8 as the major product and the trans-olefinic esters of general structure 9 as the minor product. The olefinic products may he separated by silica gel flash column chromatography.

The cis-olefinic esters of general structure 8 arie reduced with D113AL at −78° C. to give the intermediate allylic alcohol. The solvent to be used in the reduction includes methylene chloride, hexanes, and TH-IF. The product of the DIBAL reduction, the allylic alcohol, is oxidized with manganese dioxide in methylene chloride at ambient temperature to provide the cis-enals of general structure 10. The enals are converted into tricyclic derivatives of general structure 6 by condensation with the phosphonate 5 by the same processes as those employed in the preparation process of Scheme I to produce tricycles of general structure 6 and 7.

Scheme III
Synthesis of Compounds of Structure (I)

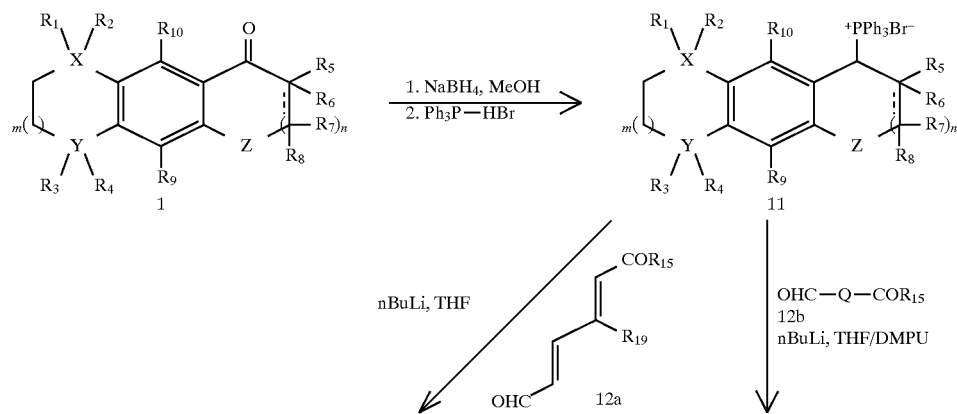

Scheme III
Synthesis of Compounds of Structure (I)

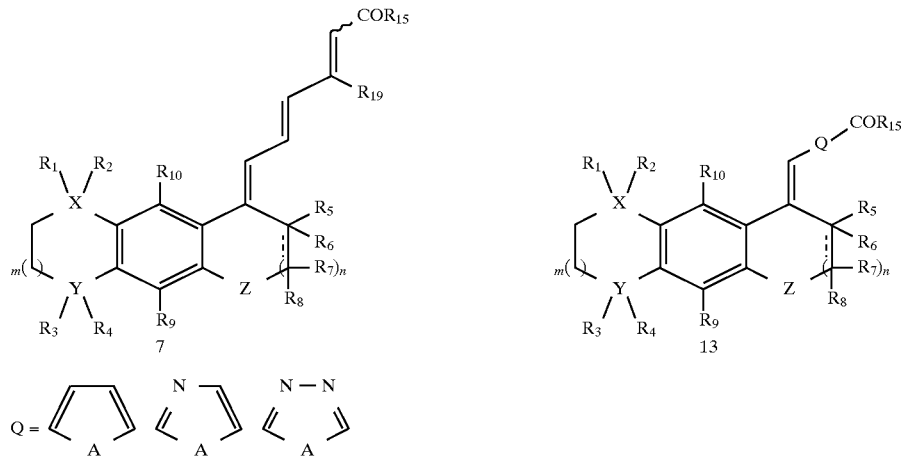

An alternative means for making the tricyclic derivatives of general structure 7 is in accordance with reaction Scheme III. The starting material for this sequence, ketones 1, may he prepared from the appropriately substituted octahydroanthiracenes hy oxidation with chromium trioxide in acetic acid at ambient temperature or with chromiuin trioxide in methylenie chloride/pyridine at low temperature. The tricyclic ketones are reduced withl sodium borohydride in methanol at low temperature and the resultnit benii.ylic alcohols are reacted with triphenylphosphine hydrobromide in methanol at elevated temperature to provide phosphonium salts of general structure 11. Compounds 12a where $R_{15}$ is ethyl and $R_{19}$ is methyl used for the following olefination reaction are prepared from commercially available (triiphenylphosphoranylidene)acetaldehyde and ethyl 3-methyl-4-oxo-crotonate. A Hoiner-Wadsworth-Emnions olefination reaction in THF at reduced temperatures with the lithium salt of compounds 11 and compounds of general structure 12a provide the tricyclic derivatives 7 where $R_{15}$ is ethoxy. The olefination reaction is preferably conducted in the presence of 1,3-dimethyl-3,4,5,6-tetrahydro-2(1H)-pyriinidinone (DMPU). The acids and salts derived from general structure 7 are readily obtainable from the corresponding esters by the salme processes as those employed in the previously described process for tricycles of general structure 6.

Compounds of general structure 13 may be prepared from the lithium salt of the phosphonium bromide of general structure 11 and aldehyde of general structure 12b by the same olefination processes as those employed for the preparation of a compound of general structure 7. The acids and salts derived from general structure 13 are readily obtainable from the corresponding esters by the same processes as those employed in the preparation process of Scheme I for tricycles of general structures 6 and 7.

Scheme IV
Synthesis of Compounds of Structure (I)

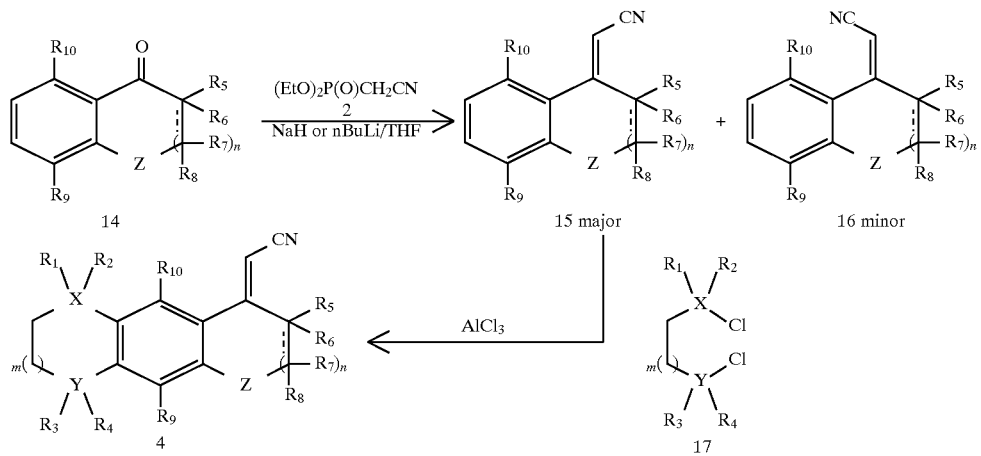

An alternative means for making the intermediate tricyclic derivatives of general structure 4 is in accordance with reaction Scheme IV. The bicyclic ketones 14 are condensed with the sodium or lithium salt of diethyl cyanomethylphosphonate in THF at reduced temiperatuLes in a Horner-Wadsworth-Emmons olefination reaction to provide a mixture of the trai-cyaino olefins 15 as the major products and the cis-cyano olefins 16 as the IlliorI products. The olefinic products may be separated by silica gel flash Colunin chromatography. Trhe tricyclic derivatives of general structure 4 are prepared by aluminum trichloride catalyzed Friedel-Cr-atts alkylation/cyclization of 2,5-dichloro-2,5-dialkylhexanes 17 with the bicycles of general structure 15 and 16 in dichloromethane at ambient temperature.

with one equivalent of DIBAL in methylene chloride at −78° C. to provide aldehydes oi general structure 19. The aidehydes are converted into tricyclic derivatives 20 by condensation with the phosphonates 5 by the same processes as those employed in the process of Scheme I to produce tricycles of general structure 6 and 7.

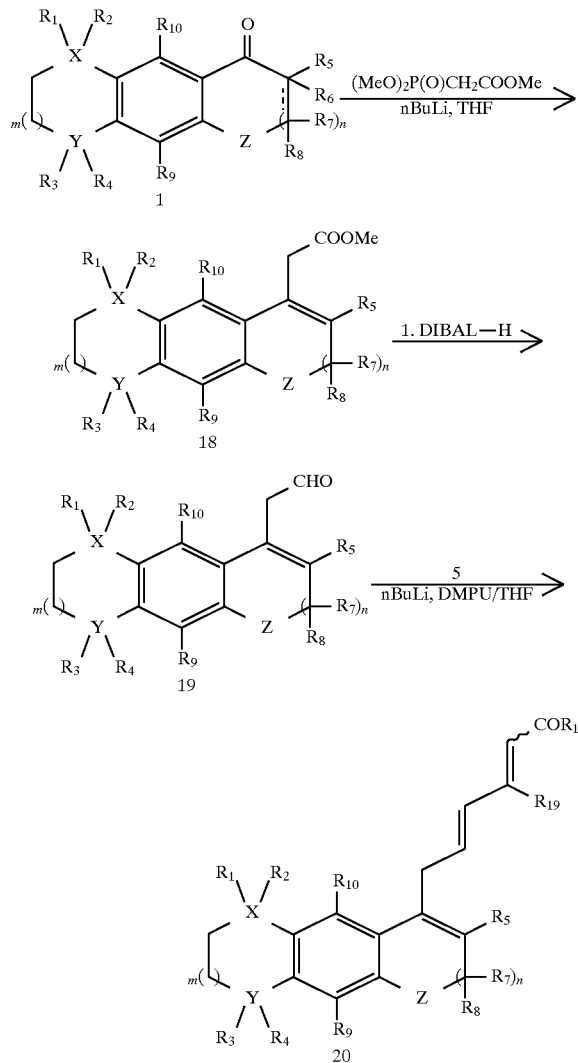

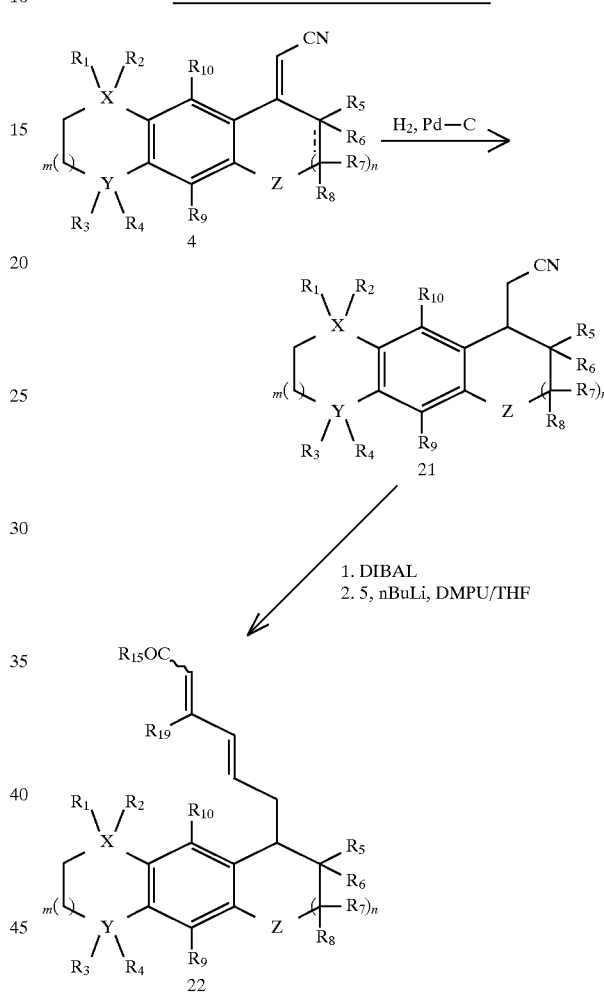

The tricyclic derivatives of general structure 20 can be prepared in accoldanlce with reaction Scheme V. Tricyclic ketones 1 are condensed with the lithium salt of trimethyl phosphonoacetate in THF at elevated temperatures in a liorner-Wadsworthi-Emimiiions olefination reaction to provide the β,γ-unsaturated esters 18. The esters are reduced The tricyclic derivatives of structure 22 can be prepared in accordance with reaction Scheme VI. The previously described unsaturated nitriles 4 (see process foi reaction Scheme I) are reduced by catalytic hydrogenation over 10% palladium-on-carbon in ethyl acetate to provide the saturated nitriles 21. In accordance with the processes employed in reaction Scheme l, the nitriles can be transformed into the tricyclic derivatives of general structure 22.

Scheme VII
Synthesis of Compounds of Structure (II)

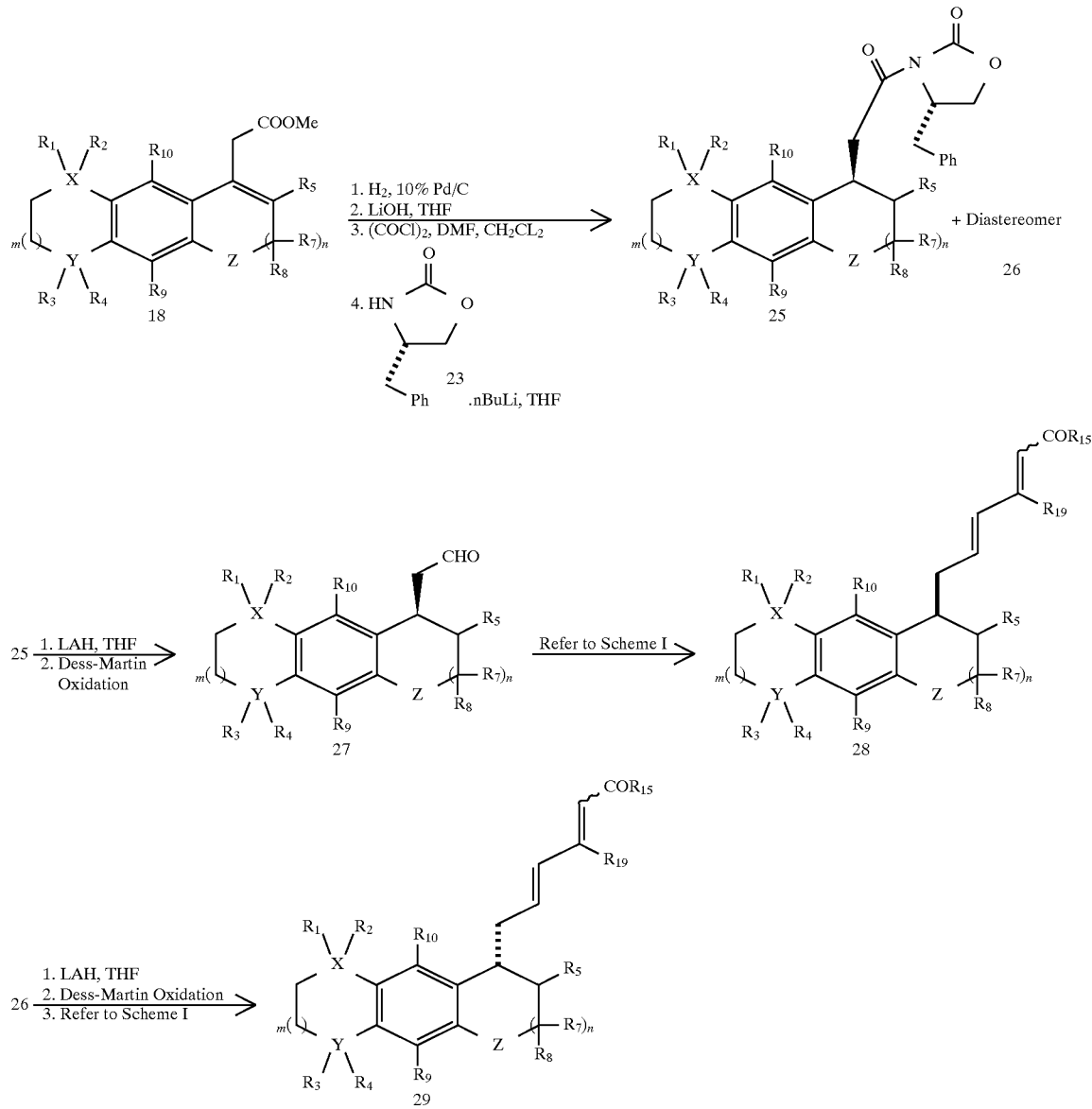

The chiral tricyclic derivatives of general structure 28 and 29 can be prepared in accordance with reaction Scheme VII. The previously described β,γ-unsaturated esters 18 (see reaction Scheme V) are reduced by catalytic hydrogenation over 10% palladitim-on-carboli in ethyl acetate to provide the intermediate saturated esters which are converted to the diastereomeric acyl oxazolidinones of general structure 25 and 26 by couplilng ot the acid chloride derivative with (S)-4-benzyl-2-oxazolidinone. The mixture of amidle diasticomiiers is separated by silica gel chromatography and each is separately reduced with LAH at reduced temperatures in THF, followed by Dess-Martin oxidation in methylene chloride at ambient temperature to provide the diastereomerically pure tricyclic aldehyde, for example tricyclic aldehydes of general structure 27. In accordance with the processes employed in reaction Scheme I, the aldehydes are transformed into the tricyclic derivatives of general structure 28 and 29.

Scheme VIII
Synthesis of Compounds of Structure (II)

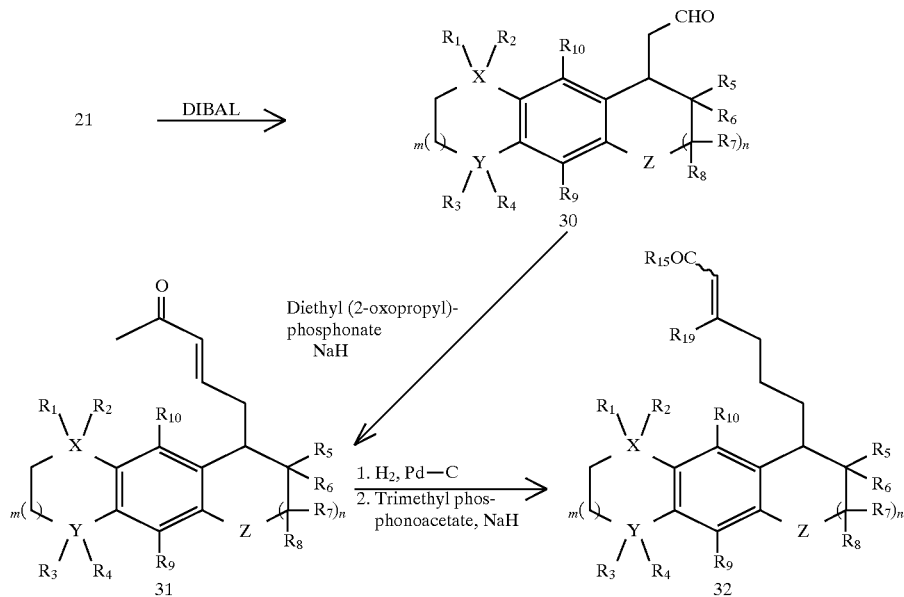

The tricyclic derivatives of general structure 32 can be prepared in accor-daince with reaction Scheme VIII. The previously described saturated nitrites 21 (see Scheme VI) are reduced with DIBAL in methylene chloride at −78° C. to provide aldelhydes ol genelal structure 30. The tricyclic aldehydes can be condensed with the sodium salt of dietliyl (2-oxopropyl)-phosphonate in THF at reduced temperatures in a fIlorner-Wadsworth-Emmonis olefination reaction to provide the α, β-unsaturated ketones 31. The enones 31 can be reduced by catalytic hydrogenation over 10% palladium-oln-carbon in ethyl acetate to provide the intermediate saturated ketones which are condensed with the sodium salt of trimethyl phosphonioacetate in TFIF at reduced temperatures in a Horner-Wa(dsworth-Emnions oletfllationl reaictioni to provide β, γ-esters of general structure 32. The acids and salts derived fromi 32 are readily obtainable from the corresponding esters by the saime processes as those employed in the preparation process of Scheme I for tri-cycles ot general structure 6 and 7.

Scheme IX
Synthesis of Compounds of Structure (III)

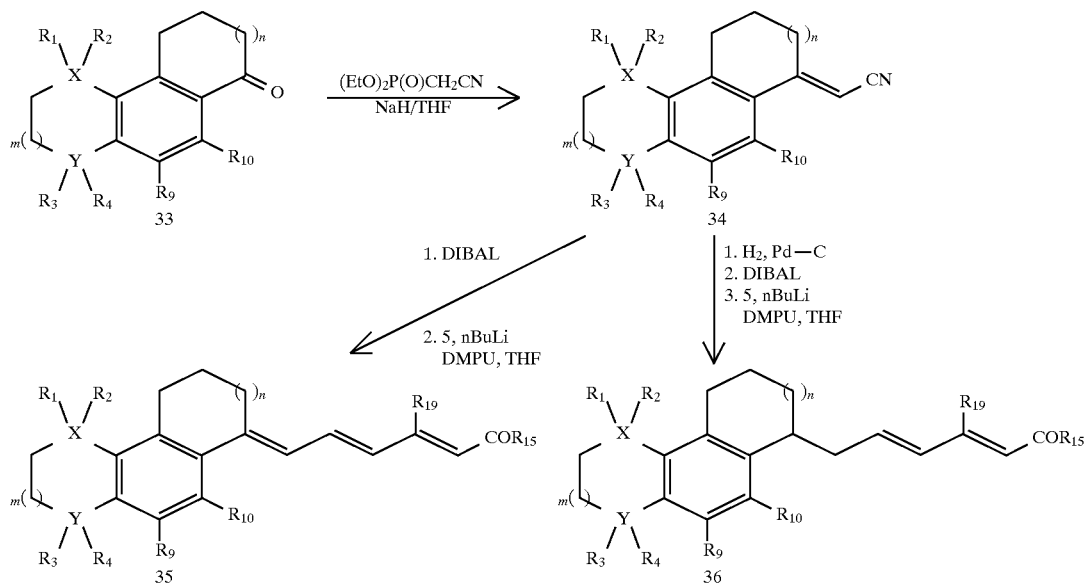

The tricyclic derivatives of general structures 35 and 36 can be prepared in accordance with reaction Scheme IX. The tricyclic trienes 35 can be prepared fronm the corresponding tricyclic ketones 33 in a manner analogous to that described in the preplrLtioll process of Scheme I for tricyclic derivatives of structures 6 and 7. The tricyclic dienes of general structure 36 are prepared from the tricyclic ketones 33 in a manner analogous to that described in the preparation process of Scheme I and Scheme VI for tricyclic derivatives of general structure 22.

with LAH in ethanol at 80° C. to afford the corresponding tricyclic amines 38, which are deprotonated with NaH at 0° C. in THF and alkylated at ambient temperature with ethyl (2E,4E)-6-bromo-3-methylhexa-2,4-dienoate to give aminodienes of general structuire 40. Alternatively, the tricyclic ailines 38 can be acylated by a DCC coupling in methylene

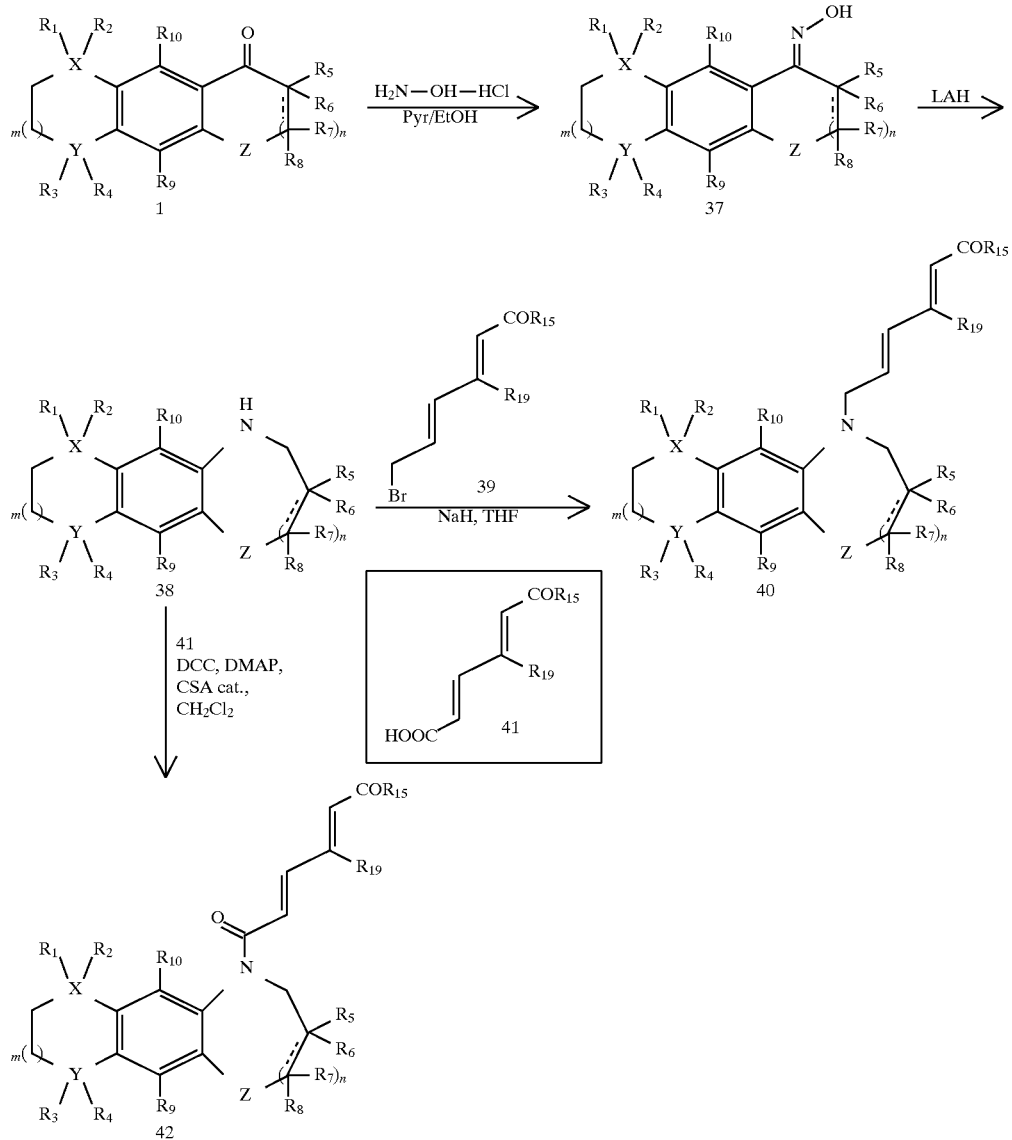

The tricyclic derivatives of general structures 40 and 42 can be prepared in accordance with reaction Scheme X. The previously described tricyclic ketones 1 (see preparation process for reaction Scheme I) are heated at reflux with hydroxylamine hydrochloride in pyridine and ethanol to provide oximes 37. A Beckman rearrangement is effected chloride with (2E,4E)-3-nietlyl-5-calrboxypenta-2,4-dienoate to give amides of general structure 42. The acids and salts derived from the esters are readily obtainable by the same processes as those employed in the preparation process of Scheme I for tricycles of general structure 6 and 7.

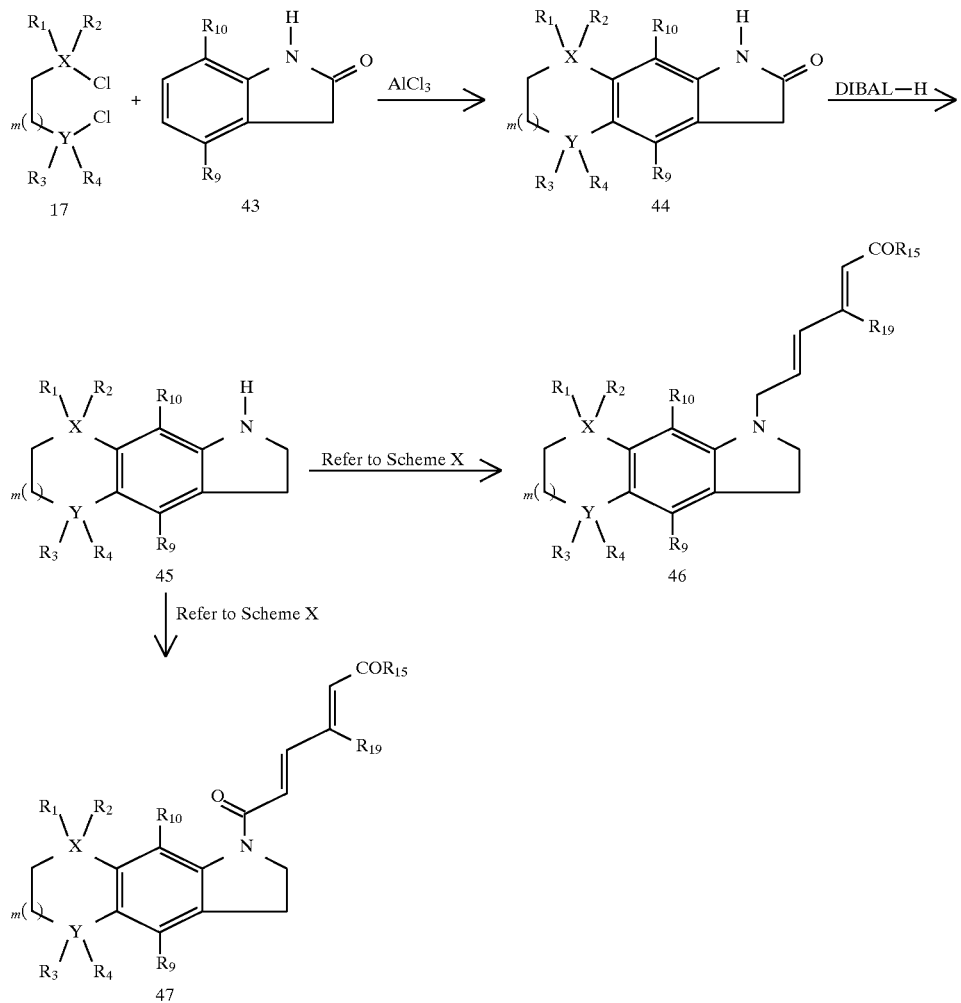

Scheme XI
Synthesis of Compounds of Structure (II)

The tricyclic derivatives of general structure 46 and 47 can be prepared in accordance with reaction Scheme XI. The tricyclic amides 44 can be prepared fmom oxiidole of general structure 43 and 2,5-dichloro-2,5-dialkylhexanes of general structure 17 by aluminum trichlioride catalyzed Friedel-Craifts alkylation/cyclization in dichloromliethaine at ambient temperature. Amides of general struLcture 44 can be reduced with DIBAI in miethyleiie chloride at 25° C. to provide the corresponding amines 45. The amine dienes 46 can be prepared from the amines 45 in a manner analogous to that described in the preparation process of Scheme X for tricyclic derivatives of general structure 40. The desired tricyclic ami(les 47 aie prepared from the corresponding tricyclic amiles of 45 in a manner anialogous to that described in the preparation process of Scheme X for tricyclic derivatives of general structure 42. The acids and salts derived from 46 and 47 are readily obtainable from the corresponding esters by the same processes as those employed in the Scheme I for tricycles of structules 6 and 7.

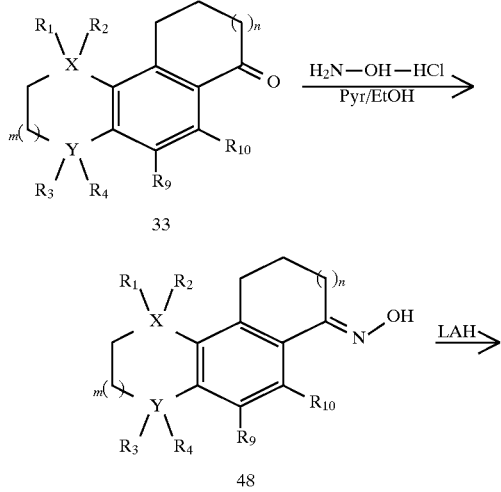

Scheme XII:
Synthesis of Compounds of Structure (III):

Scheme XII:
Synthesis of Compounds of Structure (III):

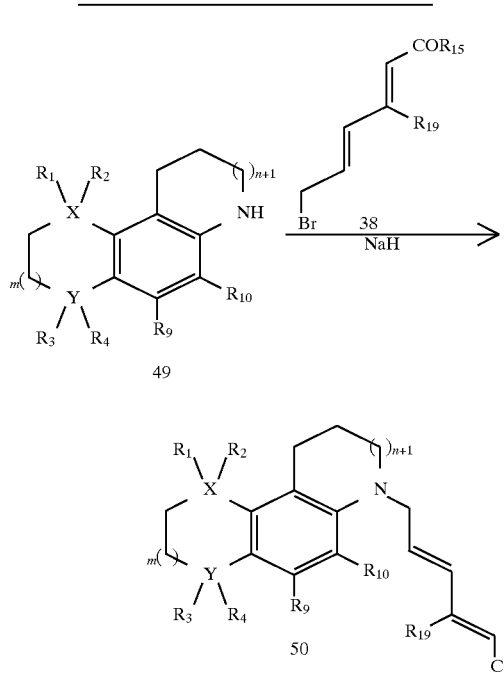

The tricyclic derivatives of general strtIcture 50 can be prepared in accordance with reaction Scheme XII. The tricyclic ketones 33 are transformed to amines of general structure 49 via Beckman type rearrangement of the intermediate oximes 48. Alkylation of the derived amines 49 with suitable alkyl halides of the type 38 provide the desired tricylcic derivatives of general structure 50. The acids and salts derived from 50 are readily obtainable from the corresponding esters by the same processes as those employed in Scheme I for tricycles of structures 6 and 7.

Scheme XIII:
Synthesis of Compounds of Structure (IV):

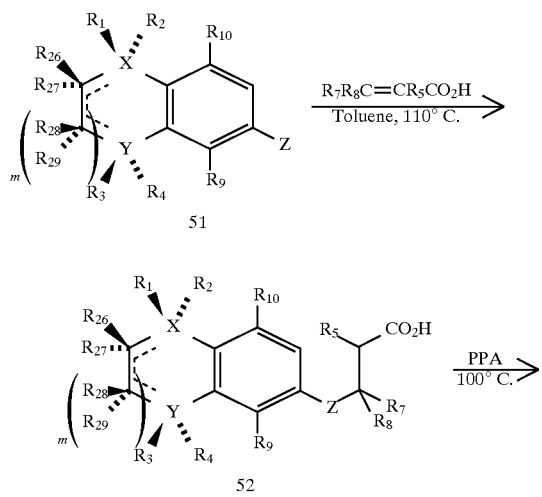

Scheme XIII:
Synthesis of Compounds of Structure (IV):

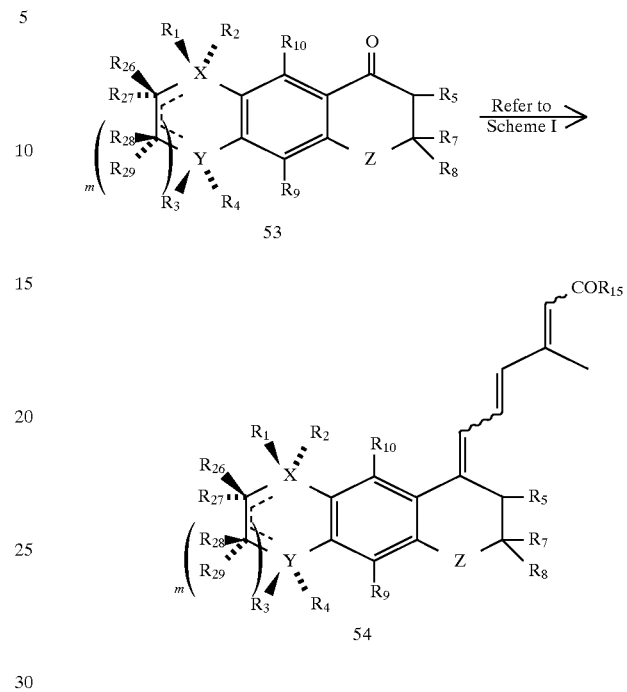

An alternative means for making the intermediate tricyclic derivatives of general structure 54 is in accordance with reaction Scheme XIII. The previously described tricyclic ketones 1 (see Example I) can be prepared in an alternative fashion, starting from the telrahtiydr-oiiaplitliilene 51. A Michael addition is effected by the addition of an acrylic acid (which can be trisubstituted) to the tetrahydronaphthalene 52 in toluene and heating the solution to I I0 ° C. for 8–16 hours. The tricyclic ketones 53 are formed by intramolecular acylation in polyphosphoric acid (PPA) at 100° C. for 8–14 hours. The ketones are converted into tricyclic derivatives 54 by condensation with the phosphonate 5 using the same processes as those employed in the process of Scheme I.

Scheme XIV:
Synthesis of Compounds of Structure (IV):

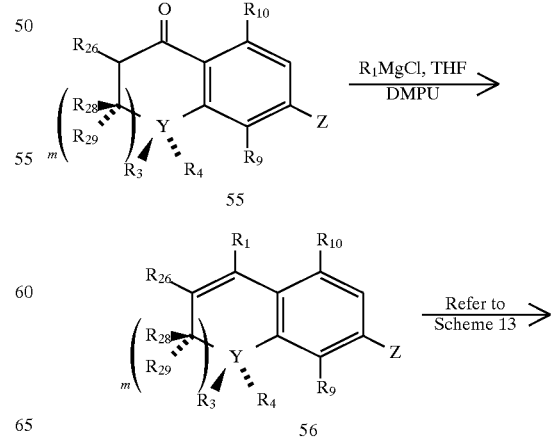

Scheme XIV:
Synthesis of Compounds of Structure (IV):

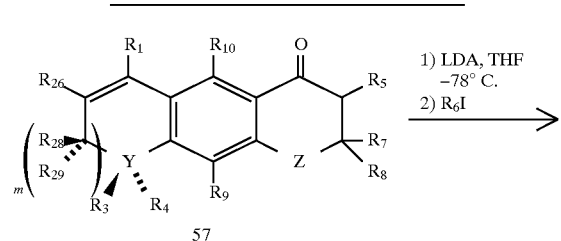

57

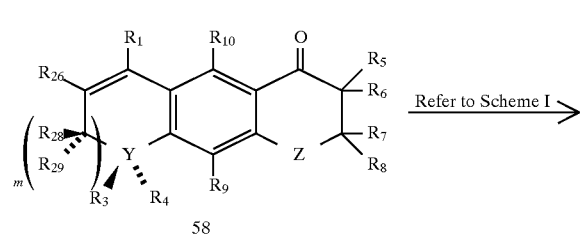

58

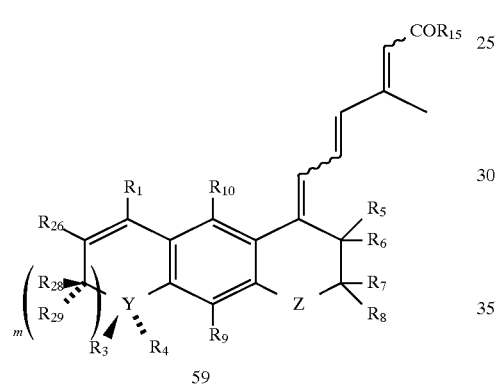

59

The tricyclic derivatives of general structure 59 can be prepared in accordance with reaction Scheme XIV. Tricyclic ketones are condensed with Grignard reagents in THF or diethyl ether at −40° C., in the presence of a co-solvent such as DMPU. Michael addition, followed by intramolecular cyclization in the presence of PPA, as in Scheme XIII, allows for the preparation of intermediate ketones such as 57. The resulting ketone can be alkylated with a variety of electrophiles, in particular alkyl halides, not restricted to methyl iodide. The ketones are converted into tricyclic derivatives 59 by condensation with the phosphonate 5 using the same processes as those employed in the process of Scheme I.

Scheme XV:
Synthesis of Compounds of Structure (VI):

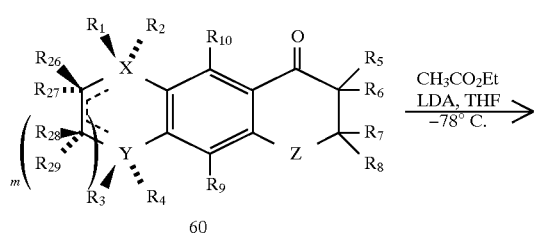

60

Scheme XV:
Synthesis of Compounds of Structure (VI):

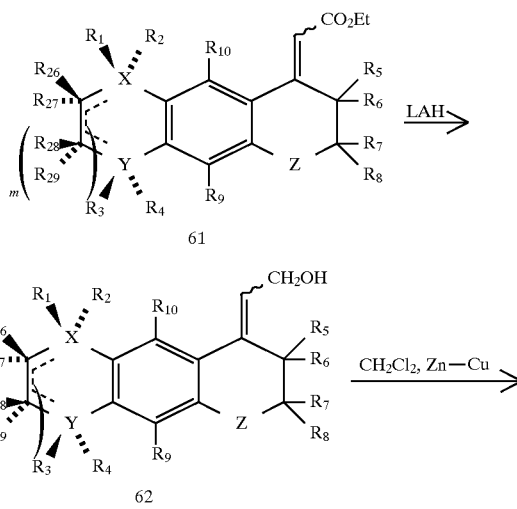

61, 62

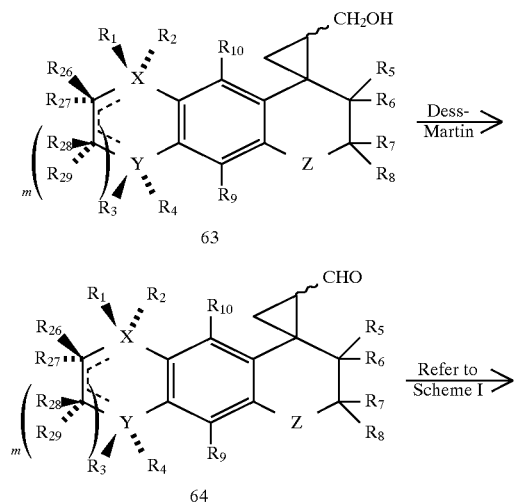

63, 64

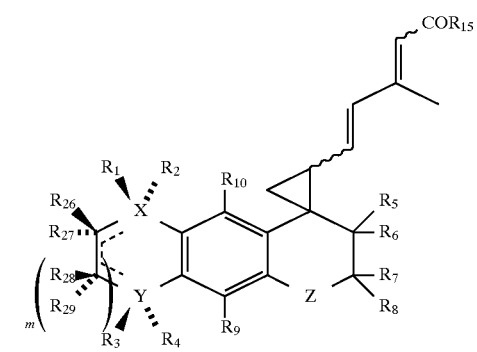

65

The tricyclic derivatives of general structure 65 can be prepared in accordcance with reaction Scheme XV The tricyclic ketones 60 can be transformed into the esters of general structure 61 by low temperature lithio enolate chemistry or a Reformlatsky reaction procedure. Reduction of the ester to the alcohol 62 facilitates the Simmons-Smith reaction. The Simmons-Smith reaction gives the spiro-cyclic cyclopropyl compound of general structure 63. Oxidation of 63, followed by the same processes as those employed in Scheme I prepare the acids and salts of general structure 65.

Scheme XVI:
Synthesis of Compounds of Structure (V):

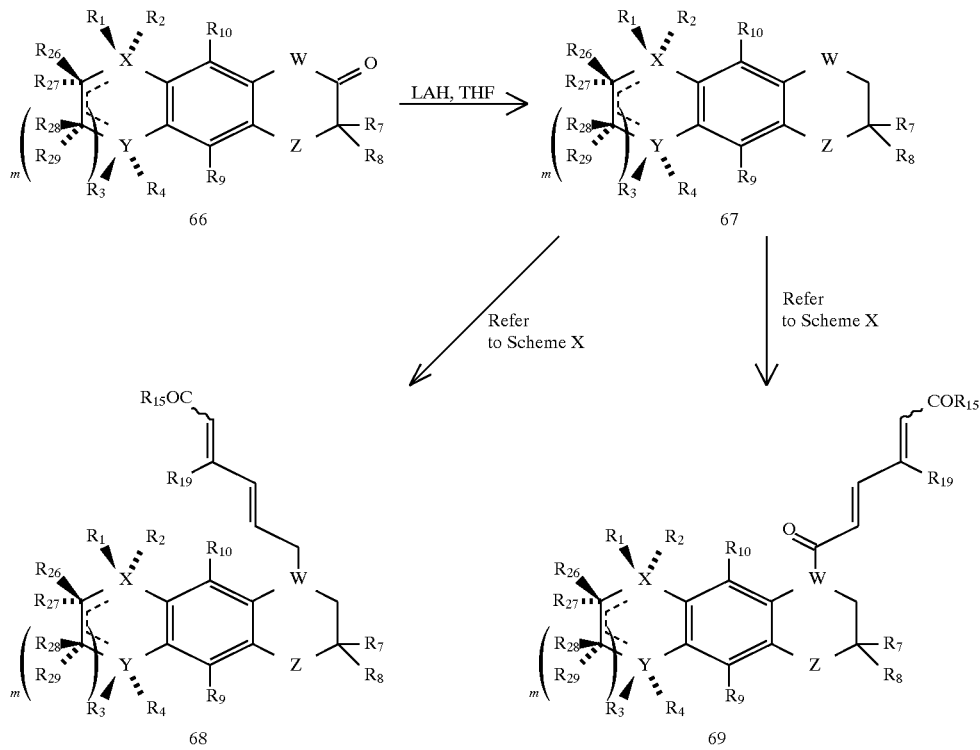

The tricyclic derivatives of general structure 68 or 69 can be prepared in accordance with reaction Scheme XVI. The tricyclic carboxylic derivatives 66 (esters or aimides) can be reduced with lithium aluminum hydride in THF to give the heterocycles of general structure 67. The acids and salts derived from 68 or 69 are readily obtained from the corresponding esters using the same processes as those employed in Scheme X.

Scheme XVII:
Synthesis of Compounds of Structure (IV):

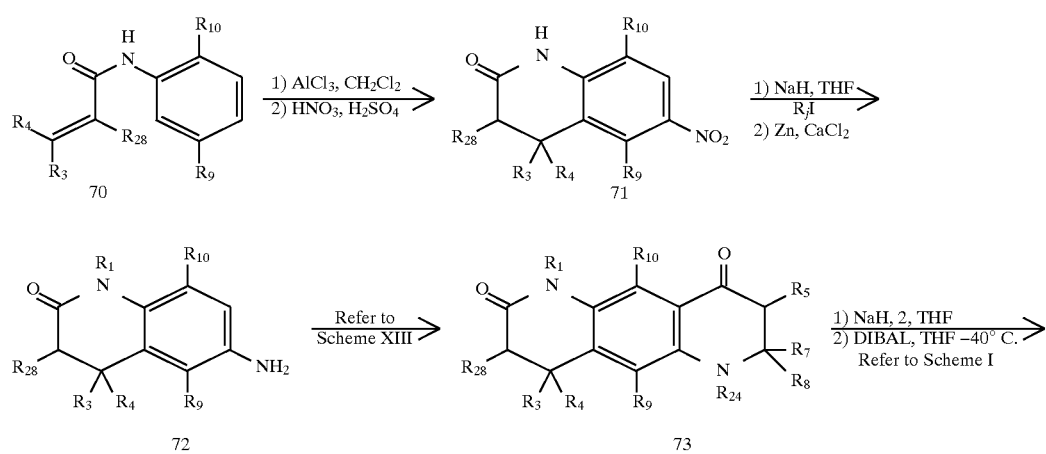

-continued
Scheme XVII:
Synthesis of Compounds of Structure (IV):

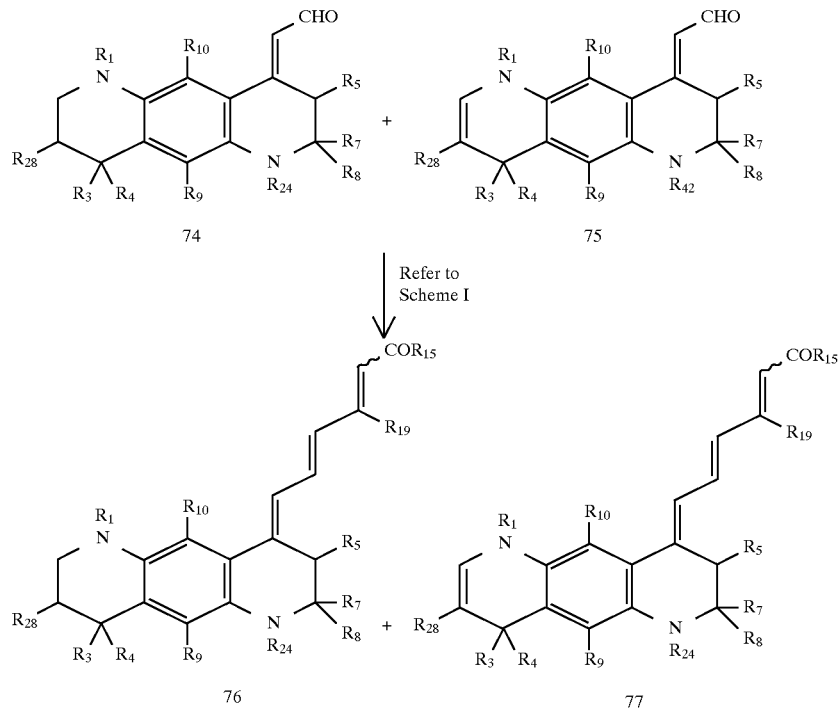

The tricyclic derivatives of general structure 76 or 77 can be prepared 'in accordance with reaction Scheme XVII. The acrylic aicid derivative 70 can be cyclized with $AlCl_3$ in dichloromethane or other nonpolar solvent to give the bicyclic compound 71. The amide can be alkylated to add the $R_1$ group function using sodium hydride in THF and a allkyl halide electrophile. The nitro group can be reduced to the amine using zinc and calciunm chloride monohydrate. Following the formation of the tricylic compound 73, as shown in Scheme XIII, the ketone 73 is converted to the nitrile as in Scheme 1. Reduction with DIBAL givcs tile aldeiydie and amine 74. An intermediate of the amide reduction process is the enamiine compound of general structure 75, which is stable and can be isolated. The mixture of products can be treated with the phosphonate reagent in Scheme I and following the procedures described therein, the acids and salts of general structure 76 or 77 can be obtained.

Scheme XVIII:
Synthesis of Compounds of Structure (IV):

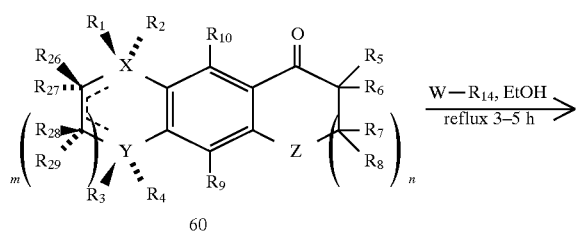

-continued
Scheme XVIII:
Synthesis of Compounds of Structure (IV):

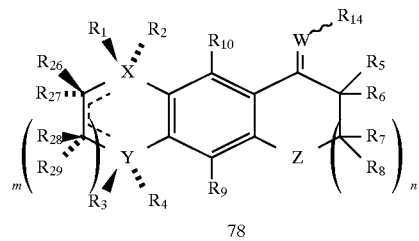

The tricyclic derivatives of general structure 78 can he prepared in accordance with reaction Scheme XVIII. The tricyclic derivatives of general structure 60 can be reacted with various nucleophiles, in particular, but not limited to amine, hydroxylamnine or hydraizine, which following dehydration, give compounds of the general structure 78.

It will be understood by those skilled in the art that certain modifications can be made to the above-described methods that remain within the scope of the present invention. For example, the compounds of the present invention may also be produced in the form of the corresponding amides or esters, or pharmaceutically acceptable salts.

The structural formulas for Compounds 101a and 101 b through 144a and 144b of the present invention are given on the following pages.

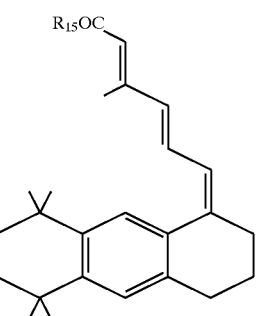
101a: R$_{15}$ = ethoxy
101b: R$_{15}$ = OH
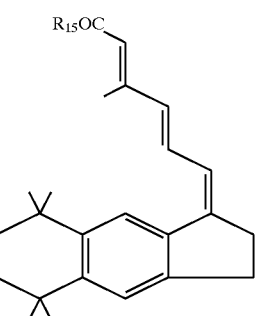
102a: R$_{15}$ = ethoxy
102b: R$_{15}$ = OH
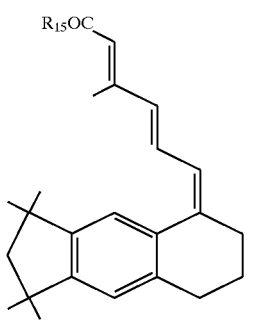
103a: R$_{15}$ = ethoxy
103b: R$_{15}$ = OH
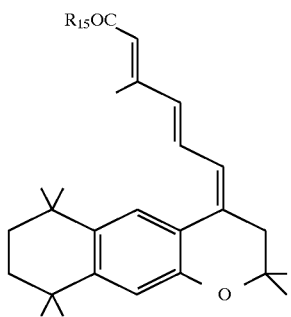
104a: R$_{15}$ = ethoxy
104b: R$_{15}$ = OH
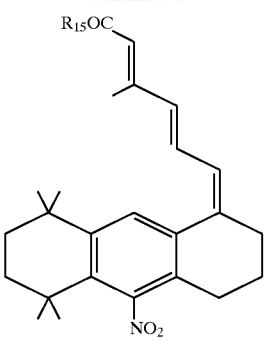
105a: R$_{15}$ = ethoxy
105b: R$_{15}$ = OH
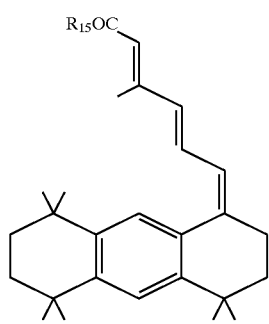
106a: R$_{15}$ = ethoxy
106b: R$_{15}$ = OH
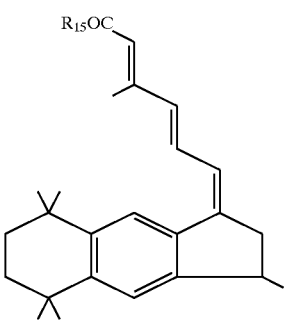
107a: R$_{15}$ = ethoxy
107b: R$_{15}$ = OH
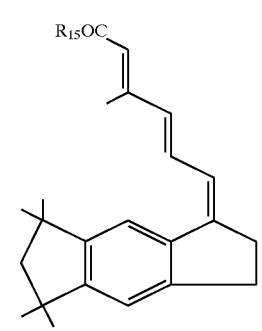
108a: R$_{15}$ = ethoxy
108b: R$_{15}$ = OH -continued
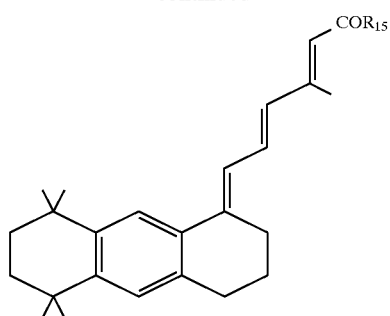
109a: R$_{15}$ = ethoxy
109b: R$_{15}$ = OH
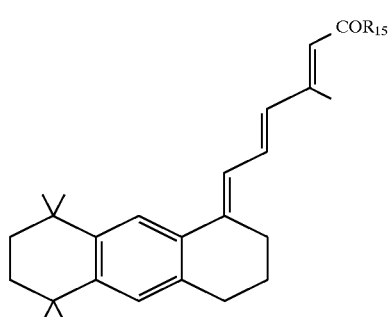
110a: R$_{15}$ = ethoxy
110b: R$_{15}$ = OH
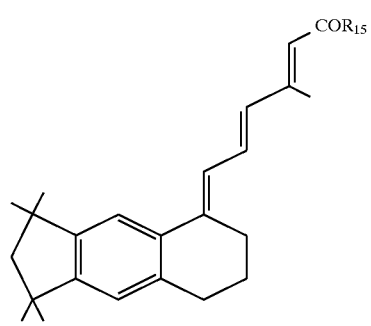
111a: R$_{15}$ = ethoxy
111b: R$_{15}$ = OH
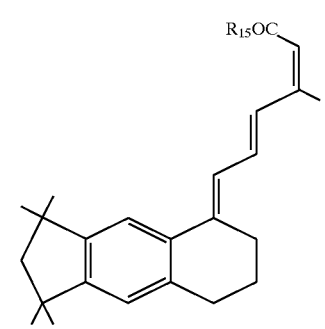
112a: R$_{15}$ = ethoxy
112b: R$_{15}$ = OH
-continued
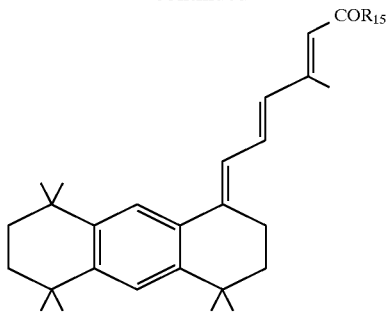
113a: R$_{15}$ = ethoxy
113b: R$_{15}$ = OH
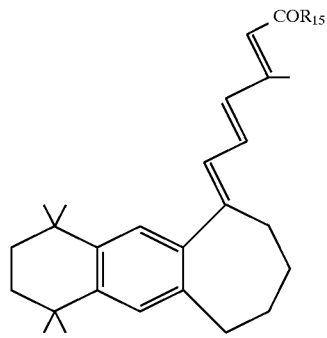
114a: R$_{15}$ = ethoxy
114b: R$_{15}$ = OH
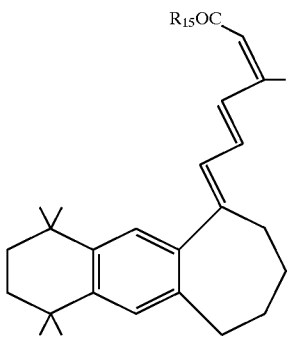
115a: R$_{15}$ = ethoxy
115b: R$_{15}$ = OH
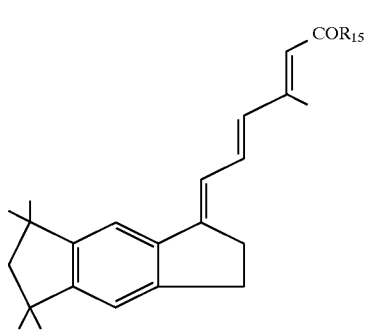
116a: R$_{15}$ = ethoxy
116b: R$_{15}$ = OH -continued
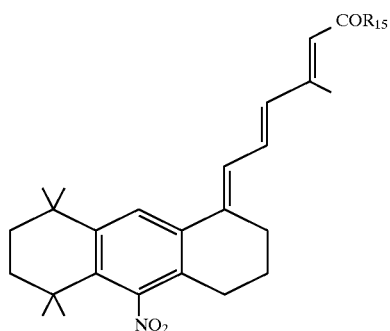
117a: R$_{15}$ = ethoxy
117b: R$_{15}$ = OH
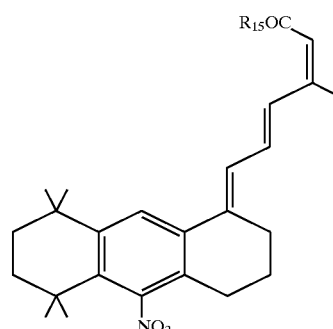
118a: R$_{15}$ = ethoxy
118b: R$_{15}$ = OH
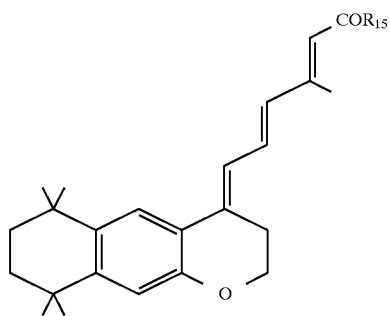
119a: R$_{15}$ = ethoxy
119b: R$_{15}$ = OH
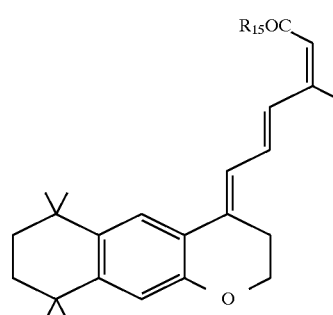
120a: R$_{15}$ = ethoxy
120b: R$_{15}$ = OH
-continued
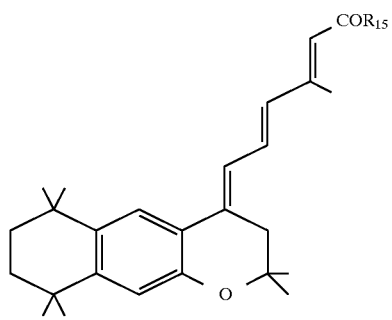
121a: R$_{15}$ = ethoxy
121b: R$_{15}$ = OH
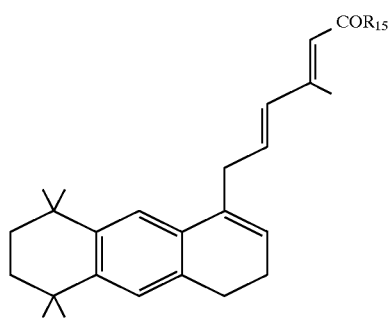
122a: R$_{15}$ = ethoxy
122b: R$_{15}$ = OH
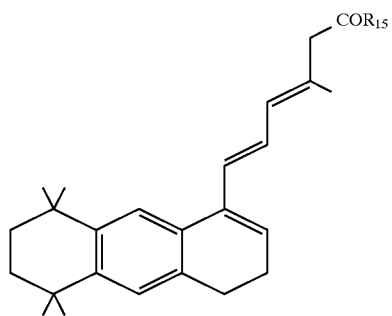
123a: R$_{15}$ = ethoxy
123b: R$_{15}$ = OH
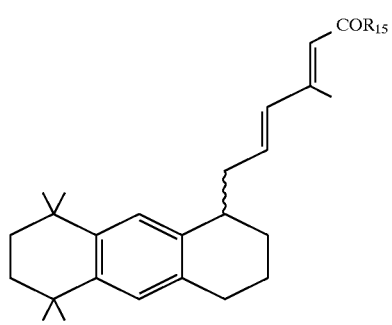
124a: R$_{15}$ = ethoxy
124b: R$_{15}$ = OH

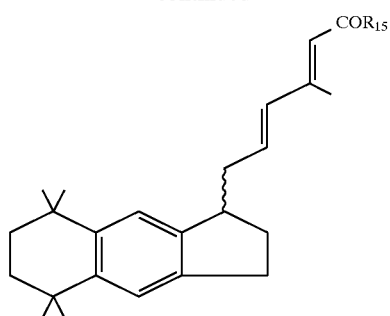
125a: R$_{15}$ = ethoxy
125b: R$_{15}$ = OH
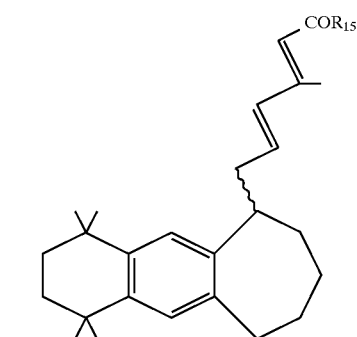
126a: R$_{15}$ = ethoxy
126b: R$_{15}$ = OH
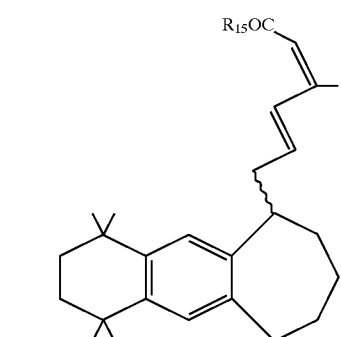
127a: R$_{15}$ = ethoxy
127b: R$_{15}$ = OH
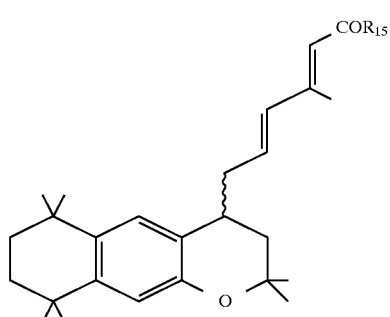
128a: R$_{15}$ = ethoxy
128b: R$_{15}$ = OH
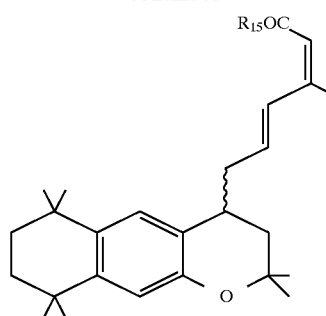
129a: R$_{15}$ = ethoxy
129b: R$_{15}$ = OH
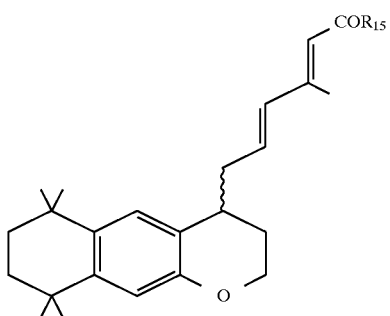
130a: R$_{15}$ = ethoxy
130b: R$_{15}$ = OH
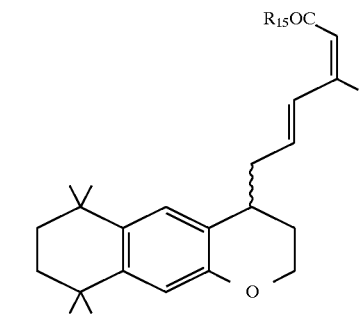
131a: R$_{15}$ = ethoxy
131b: R$_{15}$ = OH
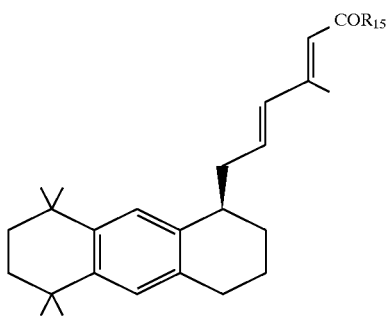
132a: R$_{15}$ = ethoxy
132b: R$_{15}$ = OH

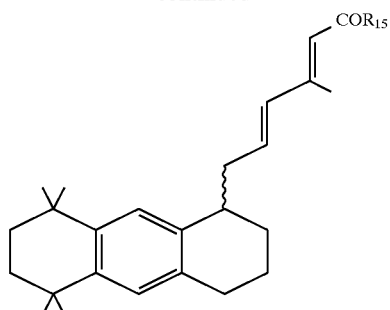
133a: R<sub>15</sub> = ethoxy
133b: R<sub>15</sub> = OH
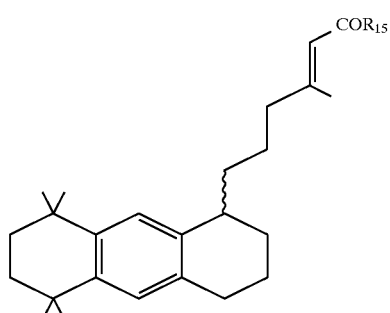
134: R<sub>15</sub> = ethoxy
134: R<sub>15</sub> = OH
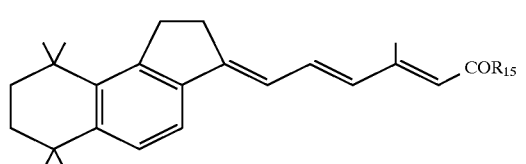
135a: R<sub>15</sub> = ethoxy
135b: R<sub>15</sub> = OH
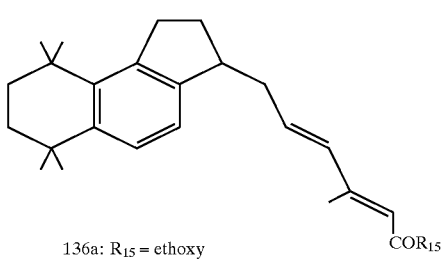
136a: R<sub>15</sub> = ethoxy
136b: R<sub>15</sub> = OH
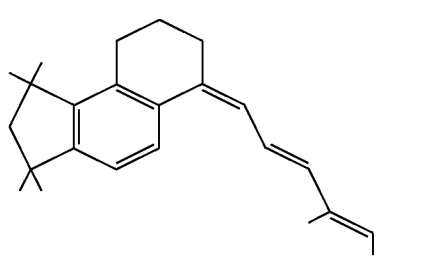
137a: R<sub>15</sub> = ethoxy
137b: R<sub>15</sub> = OH
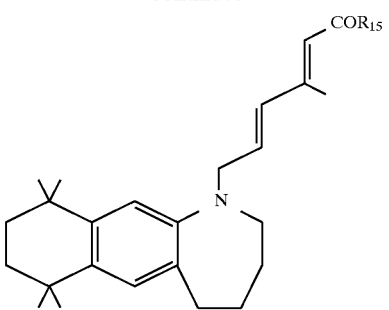
138a: R<sub>15</sub> = ethoxy
138b: R<sub>15</sub> = OH
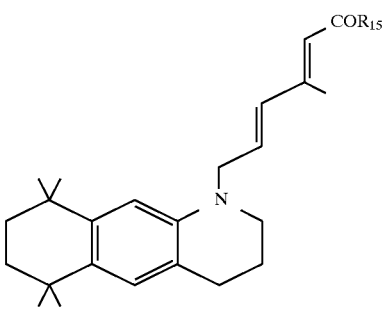
139a: R<sub>15</sub> = ethoxy
139b: R<sub>15</sub> = OH
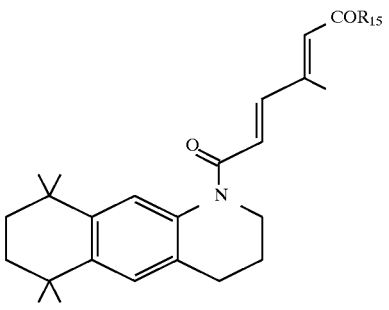
140a: R<sub>15</sub> = ethoxy
140b: R<sub>15</sub> = OH
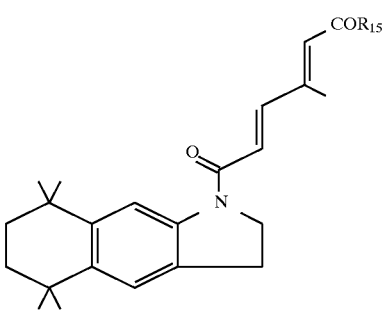
141a: R<sub>15</sub> = ethoxy
141b: R<sub>15</sub> = OH -continued
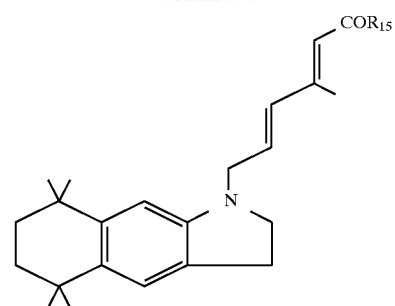
142a: R$_{15}$ = ethoxy
142b: R$_{15}$ = OH
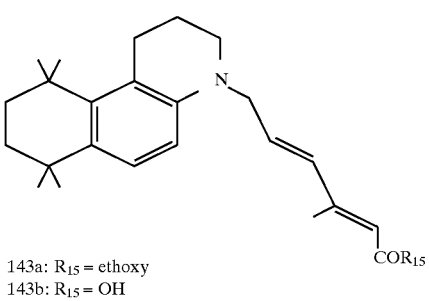
143a: R$_{15}$ = ethoxy
143b: R$_{15}$ = OH
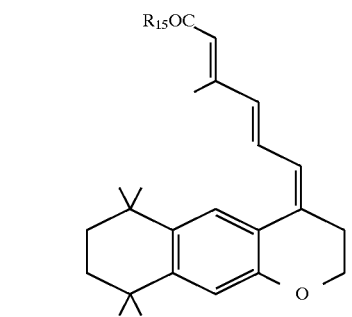
144a: R$_{15}$ = ethoxy
144b: R$_{15}$ = OH
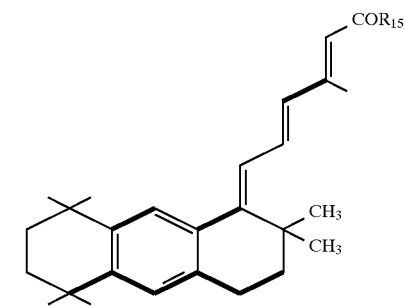
145a: R$_{15}$ = ethoxy
145b: R$_{15}$ = OH
-continued
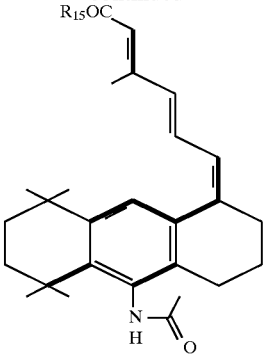
146a: R$_{15}$ = ethoxy
146b: R$_{15}$ = OH
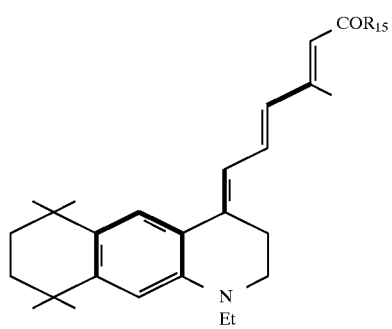
147a: R$_{15}$ = ethoxy
147b: R$_{15}$ = OH
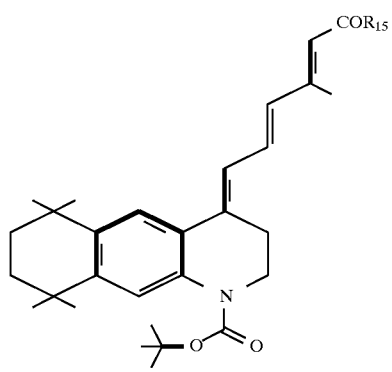
148a: R$_{15}$ = ethoxy
148b: R$_{15}$ = OH
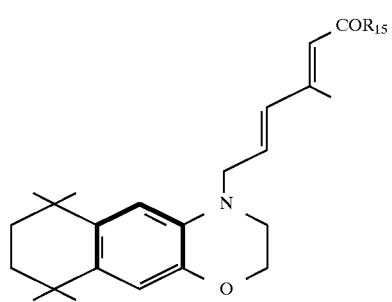
149a: R$_{15}$ = ethoxy
149b: R$_{15}$ = OH

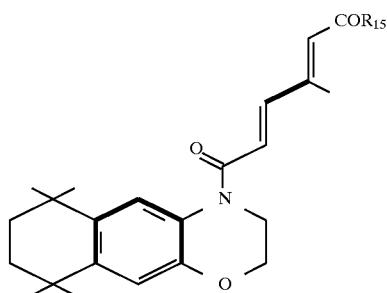

150a: R{15} = ethoxy
150b: R{15} = OH

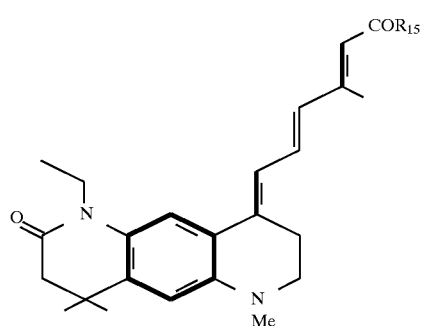

151a: R{15} = ethoxy
151b: R{15} = OH

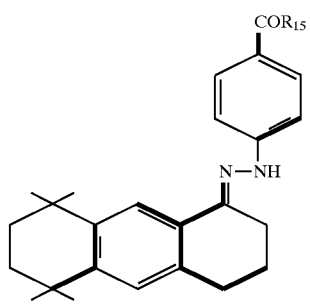

152a: R{15} = ethoxy
152b: R{15} = OH

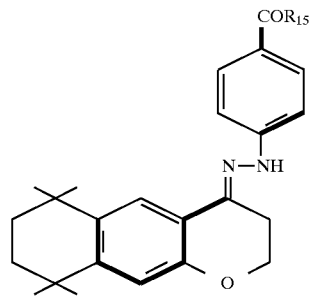

153a: R{15} = ethoxy
153b: R{15} = OH

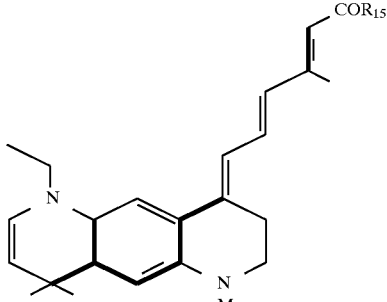

154a: R$_{15}$ = ethoxy
154b: R$_{15}$ = OH

In another aspect, the retinoid compounds of the present invention are combined in a mixture with a pharmaceutically acceptable carrier to provide pharmaceutical compositions useful for treating the biological conditions or disorders noted herein in mammalian, and more preferably, in human patients. The particular carrier employed in these pharmaceutical compositions may take a wide variety of forms depending upon the type of administration desired, e.g., intravenous, oral, topical, suppository or parenteral.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent the most advantageous oral dosage form for the pharmaceutical compositions of the present invention.

For parenteral administration, the carrier will typically comprise sterile water, although other ingredients that aid in solubility or serve as preservatives, may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions such as Eucerin™ (Beiersdorf). Examples of suitable cream bases are Nivea™ Cream (Beiersdorf), cold cream (USP), Purpose Cream™ (Johnson & Johnson) hydrophilic ointment (USP), and Lubriderm™ (Warner-Lambert).

The pharmaceutical compositions and compounds of the present invention will generally be administered in the form of a dosage unit (e.g., tablet, capsule etc.) at from about 1 μg/kg of body weight to about 500 mg/kg of body weight, more preferably from about 10 μg/kg to about 250 mg/kg, and most preferably from about 20 μg/kg to about 100 mg/kg. As recognized by those skilled in the art, the particular quantity of pharmaceutical composition according to the present invention administered to a patient will depend upon a number of factors, including, without limitation, the biological activity desired, the condition of the patient, and tolerance for the drug.

The compounds of this invention also have utility when labeled and used in assays to determine the presence of RARs and RXRs. They are particularly useful due to their ability to selectively bind to members of the RAR and RXR subfamilies and can therefore be used to determine the presence of RAR and RXR isoforms in the presence of other retinoid receptors or related intracellular receptors.

Due to the selective specificity of the compounds of this invention for retinoid receptors, these compounds can also be used to purify samples of RARs and RXRs in vitro. Such purification can be carried out by mixing samples containing retinoid receptors with one or more of the compounds of the present invention, so that the compound (ligand) binds to the receptor, and then separating out the bound ligand/receptor combination by separation techniques which are known to those of skill in the art. These techniques include column separation, filtration, centrifugation, tagging and physical separation, and antibody complexing, among others.

The compounds of the present invention also include racemate, individual stereoisomers and mixtures thereof. These isomers are then isolated by standard resolution techniques, including fractional crystallization and reverse phase and chiral column chromatography.

The compounds and pharmaceutical compositions of the present invention can advantageously be used in the treatment of the diseases and conditions described herein. In this regard, the compounds and compositions will prove particularly useful in the treatment of skin-related diseases and conditions, such as acne, psoriasis, and photo damage, cancerous and precancerous conditions, diseases of the eye, cardiovascular diseases, inflammatory and neurodegenerative diseases, diseases associated with human papilloma virus, improper pituitary function, modulation of apoptosis, diseases of the immune system, wound healing and restoration of hair growth.

Furthermore, the compounds and pharmaceutical compositions of the present invention possess a number of advantages over previously identified retinoid compounds. For example, the compounds are extremely potent activators of RARs and RXRs, preferably displaying 50% maximal activation of one or more of the retinoid receptors at a concentration of less than 100 nM, more preferably at a concentration of less than 50 nM, more preferably yet at a concentration of less than 20 nM, and most preferably at a concentration of less than 10 nM. Also, the RAR and RXR selective compounds of the present invention preferentially activate one subfamily of retinoid receptors at a level at least 2 times greater, preferably at least 5 times greater, more preferably at least 10 times greater, and most preferably at least 100 times greater than the other subfamily of retinoid receptors. In addition, the compounds of the present invention also are easier to synthesize, provide greater stability and bioavailability, and appear to be less teratogenic in comparison to all-trans retinoic acid and 9-cis retinoic acid, known RAR and RXR active compounds, respectively.

The invention will be further illustrated by reference to the following non-limiting Examples.

EXAMPLE 1

Preparation of compound 101a according to Scheme I

Ethyl (2E,4E)-3-methyl-6-[(Z)-3,4,5,6,7,8-hexahydro-5,5,8,8-tetramethyl-2H-anthracen-1-ylidene]hexa-2,4-dienoate (structure 6, where $R_1$, $R_2$, $R_3$, $R_4$, and $R_{19}$ are methyl, $R_5$, $R_6$, $R_7$, $R_8$, $R_9$, and $R_{10}$ are hydrogen, $R_{15}$ is ethoxy, X, Y and Z are carbon, m=n=1)

To a solution of 1,2,3,4,6,7,8,9-octahydro-6,6,9,9-tetramethylanthracene (2.0 g, 8.3 mmol) [prepared by Friedel-Crafts alkylation/annulation of 1,2,3,4-tetrahydronaphthalene with 2,5-dichloro-2,3-dimethylhexane in the presence of aluminum trichloride at 0° C. in dichloromethane] in $CH_2Cl_2$ (100 ml) and pyridine (15 ml) at 0° C. was added $CrO_3$ (8.26 g, 82.6 mmol) in several portions. The reaction mixture was stirred at 0° C. for 30 min, then allowed to warm up to room temperature and stirred for 10 h. The reaction mixture was poured over an ice-acid mixture (1N HCl, 100 ml), extracted with $Et_2O$ (200 ml), dried ($MgSO_4$), concentrated, and purified by column chromatography (25% ether in hexane) to give 3,4,5,6,7,8-hexahydro-5,5,8,8-tetramethyl-2H-anthracen-1-one (740 mg, 35%): $^1H$ NMR(400 MHz, $CDCl_3$) δ 8.01(s, 1H, ArH), 7.17(s, 1H, ArH), 2.90(t, J=6.5 Hz, 2H, $CH_2$, benzylic), 2.60(t, J=6.3 Hz, 2H, $CH_2$), 2.10(m, 2H, $CH_2$), 1.68(s, 4H, $2CH_2$), 1.30(s, 6H, $2CH_3$), 1.29(s, 6H, $2CH_3$).

To a solution of diethyl cyanomethylphosphonate (1.8 g, 10.4 mmol) in THF (4 ml) and DMPU (4 ml) at 0° C. was added NaH (375 mg, 65% in oil, 10.4 mmol) in one portion. The resulting solution was warmed to room temperature for 30 min. To this solution was added 3,4,5,6,7,8-hexahydro-5,5,8,8-tetramethyl-2H-anthracen-1-one (1.08 g, 4.2 mmol) in THF (2 ml). The mixture was then refluxed at 80° C. for 3 hr, cooled, quenched with saturated $NH_4Cl$ (20 ml), extracted with $Et_2O$ (100 ml), dried ($MgSO_4$), concentrated, and purified by column chromatography (10% ether in hexane) to afford cis-(1,2,3,4,6,7,8,9-octahydro-6,6,9,9-tetramethyl-2H-anthracen-1-ylidene)ethanitrile (100 mg, 10%) and trans-(1,2,3,4,6,7,8,9-octahydro-6,6,9,9-tetramethyl-2H-anthracen-1-ylidene)ethanitrile (660 mg, 66%). The cis-nitrile (structure 3) had $^1H$ NMR(400 MHz, $CDCl_3$) δ 8.31(s, 1H, ArH), 7.09(s, 1H, ArH), 5.19(s, 1H, olefinic), 2.80(t, J=6.5 Hz, 2H, $CH_2$, benzylic), 2.55(t, J=6.3 Hz, 2H, $CH_2$), 1.90(m, 2H, $CH_2$), 1.64(s, 4H, $2CH_2$), 1.26(s, 6H, $2CH_3$), 1.25(s, 6H, $2CH_3$). The trans-nitrile (structure 4) had $^1H$ NMR(400 MHz, $CDCl_3$) δ 7.46(s, 1H, ArH), 7.09(s, 1H, ArH), 5.68(s, 1H, CH, olefinic), 2.80(m, 4H, $2CH_2$), 1.90(m, 2H, $CH_2$), 1.65(s, 4H, $2CH_2$), 1.26(s, 6H, $2CH_3$), 1.25(s, 6H, $2CH_3$).

To a solution of the above Z-(3,4,5,6,7,8-hexahydro-5,5,8,8-tetramethyl-2H-anthracen-1-ylidene)ethanitrile (56 mg, 0.2 mmol) in $CH_2Cl_2$ (2 ml) at −78° C. was added DIBAL (0.4 m, 1M in $CH_2Cl_2$, 0.4 mmol). The mixture was stirred at that temperature for 10 min, then quenched with saturated potassium sodium tartrate (10 ml) at −78° C., warmed to room temperature, extracted with EtOAc (50 ml), dried ($MgSO_4$), and concentrated to give essentially pure aldehyde, which was employed for the next reaction without further purification.

A solution of diethyl 3-ethoxycarbonyl-2-methylprop-2-enylphosphonate (86 mg, 0.33 mmol) in THF (1 ml) and DMPU (1 ml) at 0° C. was treated with nBuLi (0.13 ml, 2.5M in hexane, 0.33 mM), then warmed to room temperature for 30 min. The solution was cooled to −78° C., and the above aldehyde (32 mg, 0.11 mmol) in THF (1 ml) was slowly added. Subsequently, the reaction mixture was allowed to warm to room temperature for 30 min, quenched with a saturated solution of $NH_4Cl$ (5 ml), extracted with $Et_2O$ (50 ml), dried ($MgSO_4$), concentrated, and purified by column chromatography (10% ether in hexane) to give the title ester (101a) (39 mg, 85%): $R_f$=0.48(10% ether in hexane); 1H NMR(400 MHz, $CDCl_3$) δ 7.33(s, 1H, ArH), 7.19(dd, J=15.2, 11.2 Hz, 1H, olefinic), 7.07(s, 1H, ArH), 6.32(d, J=15.2 Hz, 1H, olefinic), 6.14(d, J=11.2 Hz, 1H, olefinic), 4.15(q, 2H, $OCH_2$), 2.79(t, J=6.5 Hz, 2H, $CH_2$), 2.50(t, J=5.8 Hz, 2H, $CH_2$), 2.28(s, 3H, $CH_3$), 1.91(m, 2H, $CH_2$), 1.68(s, 4H, $2CH_2$), 1.29(s, 6H, $2CH_3$), 1.27(s, 6H, $2CH_3$), 1.24(t, J=6.8 Hz, 3H $CH_3$).

EXAMPLE 2

Preparation of compound 101b according to Scheme I (2E,4E)-3-Methyl-6-[(Z)-3,4,5,6,7,8-hexahydro-5,5,8,8-tetramethyl-2H-anthracen-1-ylidene]hexa-2,4-dienoic acid (structure 6, where $R_1$, $R_2$, $R_3$, $R_4$, and $R_{19}$ are methyl, $R_5$, $R_6$, $R_7$, $R_8$, $R_9$, and $R_{10}$ are hydrogen, $R_{15}$ is hydroxy, X, Y, and Z are carbon, m=1, and n=1)

To a solution of ester 101a (39 mg, 0.1 mmol) in MeOH (1 ml) and $H_2O$(1 ml) was added KOH (100 mg, 2.5 mmol) at 25° C. The reaction mixture was heated at 80° C. for 3 hr, cooled, acidified (1.1 ml, 2.4 N HCl), extracted with $Et_2O$ (40 ml), dried ($MgSO_4$), concentrated, and purified using column chromatography (50% ether in hexane) to obtain the title compound 101b (35 mg, 95%): $R_f$=0.32(50% ether in hexane); mp 225°–227° C.; $^1$H NMR(400 MHz, $CDCl_3$) δ7.32(s, 1H, ArH), 7.24(dd, J=15.2, 11.2 Hz, 1H, olefinic), 7.07(s, 1H, ArH), 6.34(d, J=15.2 Hz, 1H, olefinic), 6.16(d, J=11.2 Hz, 1H, olefinic), 5.80(s, 1H, olefinic), 2.79(t, J=6.4 Hz, 2H, $CH_2$, benzylic), 2.51(t, J=5.8 Hz, 2H, $CH_2$), 2.34(s, 3H, $CH_3$), 1.92(m, 2H, $CH_2$), 1.68(s, 4H, $2CH_2$), 1.29(s, 6H, $2CH_3$), 1.27(s, 6H $2CH_3$).

EXAMPLE 3

Preparation of compound 102a according to Scheme I

Ethyl (2E,4E)-3-methyl-6-[(Z)-2,3,5,6,7,8-hexahydro-5,5,8,8-tetramethyl-cyclopenta[b]napthalen-1-ylidene]hexa-2,4-dienoate (structure 6, where $R_1$, $R_2$, $R_3$, $R_4$, and $R_{19}$ are methyl, $R_5$, $R_6$, $R_7$, $R_8$, $R_9$, and $R_{10}$ are hydrogen, $R_{15}$ is ethoxy, X, Y, and Z are carbon, m=1, and n=0).

The title compound was prepared in a manner similar to that of compound 101a except that 2,3,5,6,7,8-hexahydro-5,5,8,8-tetramethylcyclopenta[b]naphthalen-1-one [US Pat. No. 2,815,382 (1957)] was used as the starting ketone (structure 1) in Example 1. Compound 102a had $R_f$=0.56 (10% ether in hexane); $^1$H NMR(400 MHz, $CDCl_3$) δ 7.68(s, 1H, ArH), 7.45(dd, J=15.0, 11.6 Hz, 1H, olefinic), 7.24(s, 1H, ArH), 6.25(d, J=15.0 Hz, 1H, olefinic), 6.22(d, J=11.6 Hz, 1H, olefinic), 5.75(s, 1H, olefinic), 4.15(q, 2H, $OCH_2$), 2.88(bm, 2H, $CH_2$, benzylic), 2.79(bm, 2H, $CH_2$, allylic), 2.48(s, 3H, $CH_3$), 1.68(s, 4H, $2CH_2$), 1.31 (s, 26H, $CH_3$), 1.29(m, 9H, $3CH_3$).

EXAMPLE 4

Preparation of Compound 102b According to Scheme I (2E,4E)-3-Methyl-6-[(Z)-2,3-5,6,7,8-hexahydro-5,5,8,8-tetramethyl-cyclopenta [b]naphthalen-1-ylidene]hexa-2,4-dienoic acid (structure 6, where $R_1$, $R_2$, $R_3$, $R_4$, and $R_{19}$ are methyl, $R_5$, $R_6$, $R_7$, $R_8$, $R_9$, and $R_{10}$ are hydrogen, $R_{15}$ is hydroxy, X, Y, and Z are carbon, m=1, and n=0).

The title compound was prepared by hydrolysis of compound 102a employing the standard hydrolysis conditions (KOH, MeOH/$H_2O$) used in Example 2. Compound 102b had $R_f$=0.45 (50% ether in hexane); mp 240°–241° C.; $^1$H NMR(400 MHz, $CDCl_3$) δ 7.67(s, 1H, ArH), 7.53(dd, J=15.0, 11.6 Hz, 1H, olefinic), 7.24(s, 1H, ArH), 6.29(d, J=15.0 Hz, 1H, olefinic), 6.26(d, J=11.6 Hz, 1H, olefinic), 5.80(s, 1H, olefinic), 2.91(bm, 2H, $CH_2$, benzylic), 2.81(bm, 2H, $CH_2$, allylic), 2.40(s, 3H, $CH_3$), 1.69(s, 4H, $2CH_2$), 1.31(s, 6H, $2CH_3$), 1.27(s, 6H, $2CH_3$).

EXAMPLE 5

Preparation of Compound 103a According to Scheme I

Ethyl (2E,4E)-3-methyl-6-[(Z)-1,2,3,6,7,8-hexahydro-1,1,3,3-tetramethyl-cycopenta[b]naphthalen-5-ylidene]hexa-2,4-dienoate (structure 6, where $R_1$, $R_2$, $R_3$, $R_4$ and $R_{19}$ are methyl, $R_5$, $R_6$, $R_7$, $R_8$, $R_9$, and $R_{10}$ are hydrogen, $R_{15}$ is ethoxy, X, Y, and Z are carbon, m=0 and n=1).

The title compound was prepared from 1,2,3,6,7,8-hexahydro-1,1,3,3-tetramethyl-cyclopenta[b]naphthalen-5-one. The preparation of this naphthalen-5-one was achieved as follows. 3,3-Dimethylcrotyl chloride was treated with 1,2,3,4-tetrahydronaphthalene in the presence of aluminum trichloride to give the corresponding 1,2,3,5,6,7,8-heptahdyro-1,1-dimethyl-3-oxo-cyclopenta[b]naphthalene, which was then geminally dimethylated with dimethyl zinc in the presence of titanium tetrachloride to afford 1,2,3,5,6,7,8-heptahdyro- 1,1,3,3-tetramethyl-cyclopenta[b]naphthalene. The naphthalene derivative was then oxidized using $CrO_3$ in acetic acid in a manner similar to that described in Example 1. The title compound 103a had $R_f$=0.85 (10% ether in hexane); $^1$H NMR (400 MHz, $CDCl_3$) δ 7.20 (dd, J=15.2, 11.2 Hz, 1H, olefinic), 7.15 (s, 1H, ArH), 6.91 (s, 1H, ArH), 6.32 (d, J=15.2 Hz, 1H, olefinic), 6.19 (s, J=11.2 Hz, 1H, olefinic), 5.77 (s, 1H, olefinic), 4.16 (q, 2H, $OCH_2$), 2.83 (t J=6.5 Hz, 2H, $CH_2$ benzylic), 2.53 (t, J=6.1 Hz, 2H, $CH_2$ allylic), 2.28 (s, 3H, $CH_3$), 1.91 (m, 2H, $CH_2$, methylene), 1.90 (s, 3H, $CH_2$, methylene), 1.43 (s, 6H, $2CH_3$), 1.32 (s, 6H, $2CH_3$), 1.27 (t, J=6.7 Hz, 3H, $CH_3$).

EXAMPLE 6

Preparation of Compound 103b According to Scheme I (2E,4E)-3-Methyl-6-[(Z)-1,2,3,6,7,8-hexahydro-1,1,3,3-tetra-cyclopenta[b]naphthalen-5-ylidene]hexa-2,4-dienoic acid (structure 6, where $R_1$, $R_2$, $R_3$, $R_4$, and $R_{19}$ are methyl, $R_5$, $R_6$, $R_7$, $R_8$, $R_9$, and $R_{10}$ are hydrogen, $R_{15}$ is hydroxy, X, Y, and Z are carbon, m=0, and n=1).

The title compound was prepared by hydrolysis of ester 103a using the standard hydrolysis conditions employed in Example 2. Compound 103b had $R_f$=0.30 (40% ether in hexane); mp 192°–194° C.; $^1$H NMR (400 MHz, $CDCl_3$) δ 7.26 (dd, J=15.2, 11.2 Hz, 1H, olefinic), 7.14 (s, 1H, ArH), 6.92 (s, 1H, ArH), 6.35 (d, J=15.2 Hz, 1H, olefinic), 6.19 (d, J=11.2 Hz, 1H, olefinic), 5.80(s, 1H, olefinic), 2.83 (t, J=6.5 Hz, 2H, $CH_2$, benzylic), 2.55 (t, J=6.1 Hz, 2H, $CH_2$, allylic), 2.30 (s, 3H, $CH_3$), 1.95 (s, 2H, $CH_2$, methylene), 1.93 (m, 2H, $CH_2$, methylene), 1.32 (s, 6H, $2CH_3$), 1.31 (s, 6H, $2CH_3$).

EXAMPLE 7

Preparation of Compound 104 b According to Scheme I (2E,4E)-3-Methyl-6-(2,3,6,7,8,9-hexahydro-2,2,6,6,9,9-hexamethylbenzo[b]-chromen-4-ylidene)-hexa-2,4-dienoic acid (structure 6, where $R_1$, $R_2$, $R_3$, $R_4$, $R_7$, $R_8$, and $R_{19}$ are methyl, $R_5$, $R_6$, $R_9$, $R_{10}$ are hydrogen, $R_{15}$=OH, X and Y are carbon, Z is oxygen, m=n=1).

The title compound was synthesized in a manner similar to that of compound 101b except 3,4,5,6,7,8-hexahydro-2,2,5,5,8,8-hexamethylnaphtho(2,3-b)-1,2-pyran-4-one (structure 1) was employed as the starting ketone. The synthesis of the pyran-4-one is detailed here. Aluminum trichloride (25 g, 0.18M) was added in portions to a solution of phenol (49.5 g, 0.52M) and 2,5-dichloro-2,5-dimethylhexane (101.0 g, 0.55M) in dichloromethane (700 ml). The reaction mixture was allowed to stir at 25°–40° C. for 2 h, then the dark red mixture was poured onto ice. Aqueous work up (EtOAc extraction) gave 5,6,7,8-tetrahydro-5,5,8,8-tetramethylnaphthalen-2-ol as a white solid, which was recrystallized from hexane to give colorless needles (84.8 g, 0.42 moles, 80%): $^1$H NMR (400 MHz, CDCl$_3$) δ 7.17 (d, 1H), 6.78 (d, 1H), 6.62 (dd, 1H), 4.55 (s, 1H), 1.65 (s, 4H), 1.25 (s, 12H). The hydroxynaphthalene (19.1g, 93.6 mmol) was treated dropwise with acetyl chloride (7.7 g, 98.2 mmol) in 1,2-dichloroethane (250ml) at 0° C. After completion of the addition, aluminum chloride (10 g, 75.2 mmol) was added in portions over 5 min. The mixture was refluxed for 10 h, then stirred at 25° C. for 8 h. GLC analysis indicated the desired keto-phenol was present in 98.6% purity. The reaction mixture was poured onto ice and aqueous work up (EtOAc extract) gave a brown-black solid, which was dissolved in hot methanol, filtered, and concentrated to give a brown viscous semi-solid. Flash chromatography (15% EtOAc/hexane) gave 1-(3-hydroxy-5,5,8,8-tetramethyl-5,6,7,8-tetrahydro-naphthalen-2-yl) ethanone as a light yellow solid. Recrystallization from hexane afforded white crystals (15.2 g, 61.8 mmol, 66%): $^1$H NMR (400 MHz, CDCl$_3$) δ 7.63 (s, 1H,), 6.9 (s, 1H), 2.61 (s, 3H), 1.67 (s, 4H), 1.29 (s, 6H), 1.27 (s, 6H).

A solution of the above hydroxyacetophenone (1.86 g, 7.5 mmol), pyrrolidine (590 mg, 7.5 mmol), acetone (850 mg, 14.6 mmol), and a catalytic amount of p-TsOH in benzene (650 ml) was heated at reflux for 48 hours. The mixture was cooled to 25° C. and diluted with 1N HCl (35 ml). Aqueous work up (Et$_2$O extraction) gave a yellowish brown solid. Recrystallization from hexane afforded 2,3,6,7,8,9-hexahydro-2,2,6,6,9,9-hexamethylbenzo [g]chromen-4-one (structure 1) as fine white crystals (560 mg, 1.95 mmol, 26%): $^1$H NMR (400 MHz, CDCl$_3$) δ 7.3 (s, 1H), 6.85 (s, 1H), 2.68 (s, 2H), 1.68 (s, 4H), 1.45 (s, 6H), 1.26 (s, 12H).

The above tricyclic ketone (556 mg, 1.95 mmol) was olefinated by means of the procedure described in Example 1 to give a crude mixture of cis and trans unsaturated nitriles. Flash chromatography (8% EtOAc/hexane) afforded (E)[2,3,6,7,8,9-hexahydro-2,2,6,6,9,9-hexamethylnaphtho-(2,3-b)-1,2 pyran-4-ylidene]ethanitrile as a light yellow solid (210 mg, 0.68 mmol): $^1$H NMR (400 MHz, CDCl$_3$) d7.35 (s, 1H), 6.8 (s, 1H), 5.7 (s, 1H), 2.82 (s, 2H,), 1.65 (s, 4H), 1.40 (s, 6H), 1.26 (d, 12H); and the (Z)-[2,3,6,7,8,9-hexahydro-2,2,6,6,9,9-hexamethylnaphtho (2,3-b)-1,2 pyran-4-ylidene] ethanitrile as a yellow solid (120 mg, 0.38 mmol): 1H NMR (400 MHz, CDCl$_3$) δ 8.30(s, 1H), 6.3(s, 1H), 5.08 (s, 1H), 2.52 (s, 2H), 1.67 (s, 4H), 1.40 (s, 6H), 1.30 (s, 6H), 1.27 (s, 6H ), 1.25 (s, 6H ).

The cis-nitrile (120 mg, 0.38 mmol) in THF mL was reduced to the corresponding aldehyde (by treatment with DIBAL at −78° under nitrogen). GLC analysis was used to monitor the reaction due to the tendency of the cis product to isomerize in the presence of DIBAL. The reaction was stopped when the appearance of the trans product was detected by GLC. Aqueous work up (EtOAc extraction) gave an orange oily solid (95 mg). Flash chromatography (8% EtOAc/hexane) afforded [(E)-2,3,6,7,8,9-hexahydro-2,2,6,6,9,9-hexamethylnaphtho (2,3-b)-1,2 pyran-4-ylidene] acetaldehyde as a light yellow solid (20 mg, 0.06 mmol, 16% yield): 1H NMR (400 MHz, CDCl$_3$) δ 10.1 (d, 1H), 7.26 (s, 1H), 6.8 (s, 1H), 5.9 (d, 1H), 2.58 (s, 2H), 1.70 (s, 4H), 1.4 (s, 6H), 1.26 (s, 6H), 1.24 (s, 6H).

The above aldehyde (19mg, 0.06 mmol) was converted to the title triene ester using the procedure similar to that described in Example 1. A total of 2.4 eq of phosphonate and base (nBuLi) was used. Aqueous work up, followed by flash chromatography (20% EtOAc/hexane) afforded a mixture of ethyl (2E,4E)- and (2Z,4E)-6-(2,3,6,7,8,9-hexahydro-benzo [g]-chromen-4-ylidene)-3-methylhexa-2,4-dienoate as a yellow oil (23.5mg, 0.055 mmol, 94% yield). $^1$H NMR indicated a 9:1 ratio of isomers favoring the trans product: $^1$H NMR (400 MHz, CDCl$_3$) δ 7.40 (s, 1H), 7.35 (dd, 1H), 6.77 (m, 1H), 6.40 (d, 1H), 6.05 (d, 1H), 5.8 (s, 1H), 4.20 (m, 2H), 2.43 (s, 2H), 2.35 (s, 3H), 1.67 (s, 4H), 1.33 (s, 6H), 1.31 (t, 3H), 1.30 (s, 6H), 1.25 (s, 6H). The isomers could not be separated by chromatography and were used as a mixture in subsequent reactions.

The above mixture of esters (23 mg, 0.054 mmol) was hydrolyzed to the corresponding acids according to the procedure described in Example 2. Removal of solvent gave the title compound as a yellow solid (19mg, 0.048 mmol, 90%). A 2.5mg sample of the crude material was purified by HPLC (80:20=MeOH: 10 mM ammonium acetate) to give the title acid 104b as a bright yellow solid (1.5mg): TLC, R$_f$=0.31(20% acetone/hexane) $^1$H NMR (400 MHz, CDCl$_3$) δ 7.40 (dd, 1H), 7.35 (s, 1H), 6.77 (s, 1H), 6.40 (d, 1H), 6.08 (d, 1H), 5.85 (br s, 1H), 2.45 (s, 2H), 2.35 (s, 3H), 1.70(s, 4H), 1.36 (s, 6H), 1.30 (s, 6H), 1.25 (s, 6H).

EXAMPLE 8

Preparation of Compound 105a According to Scheme I

Ethyl (2E,4E)-3-methyl-6-[(Z)-3,4,5,6,7,8-hexahydro-10-nitro-5,5,8,8-tetramethyl-2H-anthracen-1-ylidene]hexa-2,4-dienoate (structure 6, where R$_1$, R$_2$, R$_3$, R$_4$, and R$_{19}$ are methyl; R$_5$, R$_6$, R$_7$, R$_8$, and R$_{10}$ are hydrogen; R$_9$ is nitro; R$_{15}$ is ethoxy; X, Y, Z are carbon, m=n=1)

The title compound was prepared according to Example 1 except that 10-nitro-1,2,3,4,5,6,7,8-octahydro-5,5,8,8-tetramethylanthracene was used as the starting material. The synthesis of this intermediate is described below.

1,2,3,4,5,6,7,8-Octahydro-5,5,8,8-tetramethylanthracene (1.1 g, 4.5 mmol) was suspended in acetic acid (4 mL) and concentrated sulfuric acid (0.5 mL). The mixture was cooled to 10° C., and nitric acid (3 mL) was added dropwise so that the internal temperature remained below 20° C. The mixture was allowed to warm to room temperature and stirred for 1 h. The dark red mixture was diluted with ice/water (10 mL) and extracted with EtOAc (3×20 mL). The EtOAc layer was washed with water, saturated aqueous NaHCO$_3$, water, and brine. The solution was dried (Na$_2$SO$_4$), filtered, and concentrated to give a brown oil. The crude product was crystallized with CH$_2$Cl$_2$,ether/hexanes to give 10-nitro-1,2,3,4,5,,6,7,8-octahydro-5,5,8,8-tetramethylanthracene 1.2 g (94%) as a yellow solid: mp 129.3°–130.7° C.; IR (thin film) 2930 s, 2864 s, 1526 s, 1470 m, 1435 m, 1369 s, 1269 w, 1128 w, 918 w, 754 m cm$^{-1}$; $^1$H NMR (400 MHz, CDCl$_3$) δ 7.14 (s, 1H, aromatic), 2.72 (br s, 2H, CH$_2$), 2.50 (br s, 2H, CH$_2$), 1.75 (m, 6H, 3CH$_2$), 1.65 (m, 2H, CH$_2$), 1.32 (s, 6H, 2CH$_3$), 1.29 (s, 6H, 2CH$_3$).

10-Nitro-1,2,3,4,5,6,7,8-octahydro-5,5,8,8-tetramethylanthracen-1-one (structure 1, where R$_1$, R$_2$, R$_3$, R$_4$ are methyl; R$_5$, R$_6$, R$_7$, R$_8$, and R$_{10}$ are hydrogen; R$_9$ is nitro; X, Y, Z are carbon, m=n=1) was prepared according to Example 1 except chromium trioxide in acetic acid was used as the oxidant to give 148 mg (83% based on recovered starting material) of the ketone as a yellow solid: mp 134.0°–136.5° C.; IR (thin film) 2964 s, 2931 s, 1693 s, 1597 s, 1531 s, 1468 s, 1413 m, 1389 s, 1372 s, 1337 m, 1263 s, 1249 s, 1232 m, 1178 m, 1053 m, 912 m, 750 m cm$^{-1}$; $^1$H NMR (400 MHz, CDCl$_3$) δ 8.17 (s 1H, aromatic), 2.71 (t, J=6.2 Hz, 2H, CH$_2$), 2.63 (t, J=6.6 Hz, 2H, CH$_2$), 2.12 (m, 2H, CH$_2$); 1.74 (m, 2H, CH$_2$), 1.70 (m, 2H, CH$_2$), 1.35 (s, 6H, 2CH$_3$), 1.33 (s, 6H, 2CH$_3$); MS (Cl) m/e 302 (MH$^+$, 100), 289 (30), 272 (9).

Using the procedure described in Example 1, the above ketone was transformed into the title compound 105a which was obtained as a yellow oil: $^1$H NMR (400 MHz, CDCl$_3$)

δ 7.42 (s, 1H, aromatic), 6.98 (dd, J=15.2, 11.0 Hz, 1H, olefonic), 6.34 (d, J=15.2 Hz, 1H, olefonic), 6.21 (d, J=11.0 Hz, 1H, olefonic), 5.77 (s, 1H, olefonic), 4.14 (q, J=7.0 Hz, 2H, —OCH$_2$), 256 (t, J=6.6 Hz, 2H, CH$_2$), 2.44 (br t, J=6.2 Hz, 2H, CH$_2$), 2.23 (d, J=0.8 Hz, 3H, CH$_3$ allylic), 1.88 (m, 2H, CH$_2$), 1.71 (m, 2H, CH$_2$), 1.66 (m, 2H, CH$_2$), 1.30 (s, 6H, 2CH$_3$), 1.28 (s, 6H, 2CH$_3$), 1.28 (t, J=7.0 Hz, 3H, CH$_3$ ethyl).

EXAMPLE 9

Preparation of Compound 105b According to Scheme I (2E,4E)-3-Methyl-6-[(Z)-3,4,5,6,7,8-hexahydro-10-nitro-5,5,8,8-tetramethyl-2H-anthracen-1-ylidene]hexa-2,4-dienoic acid (structure 6, where $R_1$, $R_2$, $R_3$, $R_4$, and $R_{19}$ are methyl; $R_5$, $R_6$, $R_7$, $R_8$, and $R_{10}$ are hydrogen; $R_9$ is nitro; $R_{15}$ is hydroxy, X, Y, Z are carbon, m=n=1).

Compound 105a was hydrolyzed using the procedure of Example 2, to give the title compound 105b 3.3 mg (31%) as a yellow film: $^1$H NMR (400 MHz, CDCl$_3$) δ 7.45 (s, 1H, aromatic), 7.08 (dd, J=15.2, 11.2 Hz, 1H, olefonic), 6.42 (d, J=15.2 Hz, 1H, olefonic), 6.25 (d, J=1 1.2 Hz, 1H, olefonic), 5.84 (s, 1H, olefonic), 2.60 (t, J=6.6 Hz, 2H, CH$_2$), 2.49 (br t, J=6.3 Hz, 2H, CH$_2$), 2.29 (d, J=0.8 Hz, 3H, CH$_3$ allylic), 1.93 (m, 2H, CH$_2$), 1.75 (m, 2H, CH$_2$), 1.69 (m, 2H, CH$_2$), 1.34 (s, 6H, 2CH$_3$), 1.33 (s, 6H, 2CH$_3$).

EXAMPLE 10

Preparation of Compound 106a According to Scheme II

Ethyl (2E,4E)-3-methyl-6-[(Z)-3,4,5,6,7,8-hexahydro-4,5,,5,5,8,8-hexamethyl-2H-anthracen-1-ylidene]hexa-2,4-dienoate (structure 6, where $R_1$, $R_2$, $R_3$, $R_4$, and $R_{19}$ are methyl, $R_5$, $R_6$, $R_7$, $R_8$, $R_9$, $R_{10}$ are H, $R_{15}$ is ethoxy, X and Y are carbon; Z is C(CH$_3$)2; m=n=1).

A 100 mL round-bottom flask was flame dried under a nitrogen atmosphere, charged with dichloromethane (20.0 mL) and cooled to −40° C. A solution of titanium tetrachloride in toluene (2.0M, 11.7 mL; 23.4 mM) was added, followed by a solution of dimethylzinc in toluene (10M, 11.7 mL, 11.7 mM). The mixture was stirred at −40° C. for 30 min and a solution of 3,4,5,6,7,8-hexahydro-5,5,8,8-tetramethyl-2H-anthracen-1-one (1.0 g, 3.9 mmol, from Example 1) in dichloromethane (20 mL) was slowly added. The reaction mixture was warmed to room temperature and stirred for 36 h. The mixture was poured onto a solution of methanol and dry ice, followed by saturated ammonium chloride. The solution mixture was extracted with CH$_2$Cl$_2$, washed with water (3×20 mL), and brine (3×20 mL). The solvent was evaporated and the crude residue was purified by flash chromatography using hexanes as an eluent to give 937 mg of 1,1,5,5,8,8-hexamethyl-1,2,3,4,5,6,7,8-octahydroanthracene, 89% yield: $^1$H NMR (400 MHz, CDCl$_3$) δ 7.23 (1H, Ar), 6.93 (1H, Ar), 2.70 (t, J=8.0 Hz, 2H), 1.78 (m, 2 H), 1.65 (s, 4 H), 1.63 (m, 2 H), 1.27 (s, 3H), 1.26 (s, 6 H), 1.25 (s, 3H).

A solution of chromium trioxide (13.55 mL of a 10% CrO$_3$/AcOH solution) was slowly added to a solution of finely ground 1,1,5,5,8,8-hexamethyl-1,2,3,4,5,6,7,8-octahydroanthracene (861 mg, 3.18 mmol) in AcOH (12 mL) at 25° C. The mixture was stirred for 30 min. Ice water (100 mL) was added, and the mixture was extracted with EtOAc (3×50 mL). The organic extracts were combined and twice treated with Et$_3$N (10 mL), and washed and with sat. NaHCO$_3$ (20 mL), water (2×20 mL) and brine (2×20 mL). The solvent was evaporated and the crude residue was purified by silica gel chromatography (hexanes:EtOAc 9:1) to give 831 mg of pure 3,4,5,6,7,8-hexahydro-4,4,5,5,8,8-hexamethyl-2H-anthracen-1-one (structure 1 where $R_1$, $R_2$, $R_3$, and $R_4$ are methyl, $R_5$, $R_6$, $R_7$, $R_8$, $R_9$, and $R_{10}$ are hydrogen, X and Y are carbon, Z is C(CH$_3$)$_2$ and m=n=1):
$^1$H NMR (400 MHz, CDCl$_3$) δ 7.97 (s, 1H, Ar), 7.31 (s, 1H, Ar), 2.68 (t, J=8.0 Hz, 2H), 1.98 (t, J=6.0 Hz, 2H), 1.68 (s, 4H) 1.37 (s, 3H), 1.30 (s, 3H), 1.29 (s, 3H). The above ketone was transformed to the title compound as outlined in Scheme II.

A 50 mL round-bottom flask was flame-dried and charged with anhydrous THF (10 mL) and ethyl magnesium bromide (2.65 mL of 1M solution in THF, 2.65 mM) and the structure was cooled to 0° C. Under a nitrogen atmosphere, a solution of ethyl ethynyl ether (0.375 mL of a 50% solution in hexanes, Aldrich Inc., 2.63 mM) was slowly added. The crude mixture was warmed to room temperature and stirred for 20 min. A solution of 4,4,5,5,8,8-hexamethyl-1,2,3,4,5,6,7,8-octahydroanthracen-1-one (0.50 g, 1.76 mmol) in THF (10 mL) was slowly added and stirring was continued for 2 h. The reaction mixture was quenched with a sat. solution of ammonium chloride and extracted with diethyl ether. The organic layer was dried over MgSO$_4$, and the solvent evaporated. The crude residue was dissolved in ethanol (20 mL) and CO$_2$ (dry ice) was bubbled through the solution for 3 h. After stirring for 12 h at 25° C., the solvent was evaporated and the residue was purified by silica gel chromatography to give 455 mg (73% yield) of a mixture of (Z) and (E) esters in a 3.5:1 ratio. The mixture of esters (455 mg, 1.28 mmol) was dissolved in anhydrous dichloromethane (5.0 mL) and cooled to −78° C. DIBAL in dichloromethane (3.2 mL of 1.0M solution, 3.2 mM) was added and the mixture stirred for 15 min. The reaction was quenched at −78° C. using a saturated solution of Rochelle salt and extracted with dichloromethane. The organic layer was dried over MgSO$_4$, then evaporated to give a white residue which was purified by chromatography to afford the corresponding cis allylic alcohol (211 mg) and trans allylic alcohol (37 mg). The cis-alcohol 2-[(Z)-3,4,5,6,7,8-hexahydro-4,4,5,5,8,8-hexamethyl-2H-anthracene-1-ylidine] ethanol: $^1$H NMR (400 MHz, CDCl$_3$) δ 7.25 (s, 1H, Ar), 7.03 (s, 1H, Ar), 5.57 (t, J=4.5 Hz, 1H), 4.43 (t, J=4.5 Hz, 2H), 2.46 (m, 2H), 1.75 (m, 2H), 1.67 (s, 4H), 1.28 (s, 18H). The trans-alcohol 2-[(E)-3,4,5,6,7,8-hexahydro-4,4,5,5,8,8-hexamethyl-2H-anthracene-1-ylidine] ethanol; $^1$H NMR (400 MHz, CDCl$_3$) δ 7.56 (s, 1H, Ar), 7.02 (s, 1H, Ar), 6.15 (t, J=4.5 Hz, 1H), 4.39 (t, J=4.5 Hz, 2H), 2.46 (m, 2H), 1.75 (m, 2H), 1.68 (s, 4H), 1.27 (s, 18H).

To a solution of 2-[(Z)-3,4,5,6,7,8-hexahydro-4,4,5,5,8,8-hexamethyl-2H-anthracene-1-ylidine] ethanol (100 mg, 0.32 mmol) in dichloromethane (2.0 mL) was added a total of 200 mg of MnO$_2$ in 4 portions. The mixture was stirred for 1 h, then filtered through a pad of celite and thoroughly rinsed with dichloromethane (total of 20 mL). The solvent was evaporated to give 93 mg of the virtually pure corresponding aldehyde (98% yield) which was used directly in the next step. A flame-dried 25 mL round-bottom flask was charged into diethyl 3-ethoxycarbonyl-2-methylprop-2-enylphosphonate (142 mg, 0.53 mmol) and anhydrous THF (15.0 mL) and the solution was cooled to 0° C. Anhydrous DMPU (0.25 mL) and nBuLi in hexanes (0.34 mL of 1.5M solution, 0.51 mM) were added. The mixture was stirred at 0° C. for 20 min, then cooled to −78° C. A solution of the above aldehyde in THF (3.0 mL) was added dropwise. After stirring at −78° C. for 10 min, the mixture was allowed to warm to room temperature. After 30 min, the reaction was quenched with a saturated aqueous solution of ammonium chloride and extracted with EtOAc. The organic layer was dried over $MgSO_4$ and the solvent was evaporated. The residue was purified by chromatography to give the title ester 106a (108 mg, 86% yield): $^1$H NMR (400 MHz, $CDCl_3$) δ 7.25 (m, 3H, 2ArH and 1 vinylic H), 6.38 (d, J=16 Hz, 1H), 6.27 (d, J=12 Hz, 1H), 5.80 (s, 1H), 4.1 (q, J=4.5 Hz, 2H, O—$CH_2$—), 2.55 (t, J=4.5 Hz, 2H), 2.32 (s, 3H, $CH_3$), 1.78 (t, J=4.0 Hz, 2H), 1.69 (s, 4H), 1.30 (s, 18H), 1.28 (t, J=4.0 Hz, 3H). $^1$H NMR data indicated the presence of a geometric isomer at the 2,3 double bond in a ratio of trans:cis 5:1.

EXAMPLE 11

Preparation of Compound 106b According to Scheme II (2E,4E)-3-Methyl-6-[(Z)-1,2,3,4,5,6,7,8-hexahydro-4,4,5,5,8,8-hexamethyl-2H-anthracen-1-ylidene]hexa-2,4-dienoic acid (structure 6 where $R_1$, $R_2$, $R_3$, $R_4$, and $R_{19}$ are methyl; $R_5$, $R_6$, $R_7$, $R_8$, $R_9$, and $R_{10}$ are H; $Ri_{15}$ is hydroxy; X and Y are carbon; Z is $C(CH_3)_2$; m=n=1).

To a solution of the above compound 106a (108 mg, 0.23 mmol) in ethanol (3.0 mL) was added NaOH (100 mg) and water (3.0 mL). The mixture was heated at 70° C. for 4 h, then cooled to room temperature, acidified using 1 N HCl, and extracted with EtOAc (20 mL). The organic layer was washed with water (2×10 mL), brine (2×10 miL) and dried over $MgSO_4$. The solvent was evaporated and the residue was recrystallized from acetone-water three times to give the geometrically pure title acid 106b in 56%: $^1$H NMR (400 MHz, $CDCl_3$) δ 7.25 (m, 3H, 2ArH and 1 vinylic H), 6.38 (d, J=16 Hz, 1H), 6.27 (d, J=12 Hz, 1H), 5.80 (s, 1H), 2.55 (t, J=4.5 Hz, 2), 2.32 (s, 3H, $CH_3$), 1.78 (t, J=4.0 Hz, 2H), 1.69 (s, 4H), 1.3 (s, 18H).

EXAMPLE 12

Preparation of Compound 107b According to Scheme II (2E,4E)-3-Methyl-6-[(Z)-2,3,5,6,7,8-hexahydro-3,5,5,8,8-pentamethyl-cyclopenta [b]naphthalen-1-ylidene]hexa-2,4-dienoic acid (structure 6, where $R_1$, $R_2$, $R_3$, $R_4$ and $R_{19}$ are methyl; $R_5$, $R_6$, $R_9$ and $R_{10}$ are hydrogen; $R_{15}$ is hydroxy; X and Y are carbon; Z is $CHCH_3$; m=1 and n=0)

The title acid was prepared from 2,3,5,6,7,8-hexahydro-3,5,5,8,8-pentamethyl-cyclopenta [b]naphthalen-1-one. The preparation of the above naphthalen-1-one is shown below. Friedel-Crafts alkylation of crotonic acid with 1,2,3,4-tetrahydro-1,1,4,4-tetramethylnaphthalene in the presence aluminum trichloride gave the corresponding enone, which was then cyclized to the naphthalen-1-one using PPA at 110° C. for 3 h). Procedures similar to those in Examples 10 and 11 afforded the compound 107b: $R_f$=0.25 (40% ether in hexane); mp 216°–218° C.; $^1$H NMR (400 MHz, $CDCl_3$) d: 7.66(s, 1H, ArH), 7.54(dd, J=15.1, 11.6 Hz, 1H, olefinic), 7.22(s, 1H, ArH), 6.31(d, J=15.1 Hz, 1H, olefinic), 6.27(d, J=11.6 Hz, 1H, olefinic), 5.82(s, 1H, olefinic), 3.20(m, 1H), 2.99(m, 1H, allylic), 2.42(m, 4H, $CH_3$, allylic), 1.71(s, 4H, $2CH_2$), 1.33(m, 6H, $2CH_3$), 1.30(m, 9H, $3CH_3$).

EXAMPLE 13

Preparation of Compound 108b According to Scheme II (2E,4E)-3-Methyl-6-[(Z)-3,5,6,7-tetrahydro-5,5,7,7-tetramethyl-2H-5-indacen-1-ylidene]hexa-2,4-dienoic acid (structure 6, where $R_1$, $R_2$, $R_3$, $R_4$, and $R_{19}$ are methyl; $R_5$, $R_6$, $R_7$, $R_8$, $R_9$ and $R_{10}$ are hydrogen; $R_{15}$ is hydroxy; X, Y and Z are carbon; m=n=0)

The title acid was prepared from 5,5,7,7-tetramethyl-3,5,6,7-tetrahydro-2H-5-indacen-1-one using procedures similar to those of Examples 10 and 11. The above indacen-1-one was prepared in a manner similar to that of 1,2,3,6,7,8-hexahydro-1,1,3,3-tetramethyl-cyclopenta[b]naphthalene-5-one in Example 5, except that indane was employed as the starting material. The title compound 108b had $R_f$=0.35 (50% ether in hexane); mp 159°–161° C.; $^1$H NMR (400 MHz, $CDCl_3$) d: 7.52(dd, J=15.4, 12.9 Hz, 1H, olefinic), 7.43(s, 1H, ArH), 7.06(s, 1H, ArH), 6.31(d, J=15.4 Hz, 1H, olefinic), 6.28(d, J=12.9 Hz, 1H, olefinic), 5.83(s, 1H, olefinic), 2.95(m, 2H, $CH_2$, benzylic), 2.88(m, 2H, $CH_2$, allylic), 2.40(s, 3H, $CH_3$), 1.96(s, 2H, $CH_2$), 1.34(m, 6H, $2CH_3$), 1.32(s, 6H, $2CH_3$).

EXAMPLE 14

Preparation of Compound 109a According to Scheme III

Ethyl (2E,4E)-3-methyl-6-[(E)-3,4,5,6,7,8-hexahydro-5,5,8,8-tetramethyl-2H-anthracen-1-ylidene]hexa-2,4-dienoate (structure 7, where $R_1$, $R_2$, $R_3$, $R_4$, and $R_{19}$ are methyl; $R_5$, $R_6$, $R_7$, $R_8$, $R_9$, $R_{10}$ are hydrogen; $R_{15}$ is ethoxy; X, Y, and Z are carbon; m=n=1).

To a solution of 3,4,5,6,7,8-hexahydro-5,5,8,8-tetramethyl-2H-anthracen-1-one (512 mg, 2 mmol, from Example 1) in MeOH(10 ml) was added $NaBH_4$ (76 mg, 2 mmol) at 0° C. The reaction mixture was stirred at that temperature for 30 min, then quenched with sat. aqueous $NH_4Cl$ (5 ml), extracted with ether (50 ml), dried ($MgSO_4$), and concentrated under reduced pressure to give the corresponding tricyclic alcohol, which was used without further purification. To the above alcohol (516 mg, 2 mmol) in MeOH (5 ml) was added $Ph_3P$-HBr (686 mg, 2 mmol) at 25° C. The mixture was heated at 85° C. for 5 h. Removal of the solvent, followed by addition of hexane (100 ml) gave a white solid, which was then filtered to give pure 3,4,5,6,7,8-hexahydro-5,5,8,8-tetramethyl-2H-anthracen-1-triphenylphosphonium bromide (697 mg, 60%).

To a solution of the above phosphonium salt (581 mg, 1 mmol) in THF (8 ml) was added nBuLi (0.4 ml, 2.5M, 1 mM) at 0° C. and the resulting dark-red solution was stirred at that temperature for 30 min to afford the ylide. To this freshly prepared ylide was added ethyl (2E,4E)-3-methyl-5-formylpenta-2,4-dienoate. [The ethyl dienoate was prepared by the condensation of ethyl-3-methyl-4-oxocrotonate and (triphenylphosphoranylidene)acetaldehyde in benzene at 85° C. for 3 h using benzoic acid as a catalyst (168 mg, 1 mmol) in THF(5 ml) at 0° C., and the resulting mixture was stirred at this temperature for 30 min.] The reaction mixture was quenched with $NH_4Cl$ (10 ml), extracted with ether (50 ml), dried($MgSO_4$), concentrated, and purified by chromatography (10% ether in hexane) to give the pure title compound 109a (372 mg, 95%): $R_f$=0.52 (10% ether in hexane); $^1$H NMR(400 MHz, $CDCl_3$) δ 7.58 (s, 1H, ArH), 7.04 (dd, J=11.2, 15.0 Hz, 1H, olefinic), 7.02 (s, 1H, ArH), 6.69 (d, J=11.2 Hz, 1H, olefinic), 6.39 (d, J=15.0 Hz, 1H, olefinic), 5.79 (s, 1H, olefinic), 4.16 (q, 2H, $OCH_2$), 2.75 (t, J=6.1 Hz, 2H, $CH_2$, benzylic), 2.68 (t, J=5.9 Hz, 2H, $CH_2$, allylic), 2.36 (s, 3H, $CH_3$), 1.85 (m, 2H, $CH_2$), 1.65 (s, 4H, $2CH_2$), 1.31 (s, 6H, $2CH_3$), 1.25 (m, 9H, $3CH_3$).

EXAMPLE 15

Preparation of Compound 109b According to Scheme III (2E,4E)-3-Methyl -6-[(E)-3,4,5,6,7,8-hexahydro-5,5,8,8-tetramethyl-2H-anthracen-1-ylidene]hexa-2,4-dienoic acid (structure 7, where $R_1$, $R_2$, $R_3$, $R_4$, and $R_{19}$ are methyl, $R_5$, $R_6$, $R_7$, $R_8$, $R_9$, and $R_{10}$ are hydrogen, $R_{15}$ is hydroxy, X, Y, and Z are carbon, m=n=1).

The title acid was prepared from hydrolysis of compound 109a using the standard conditions employed in Example 2. Compound 109b had $R_f$=0.25 (50% ether in hexane); mp 230°–231° C.; $^1$H NMR (400 MHz, CDCl$_3$) δ 7.60(s, 1H, ArH), 7.09(dd, J=1.2, 15.0 Hz, 1H, olefinic), 7.03(s, 1H, ArH), 6.70 (d, J=11.2 Hz, 1H, olefinic), 6.43 (d, J=15.0 Hz, 1H, olefinic), 5.82 (s, 1H, olefinic), 2.77 (t, J=6.1 Hz, 2H, CH$_2$, benzylic), 2.70 (t, J=5.9 Hz, 2H, CH$_2$, allylic), 2.37 (s, 3H, CH$_3$), 1.86 (m, 2H, CH$_2$), 1.67 (s, 4H, 2CH$_2$), 1.31 (s, 6H, 2CH$_3$), 1.26 (s, 6H, 2CH$_3$).

EXAMPLE 16

Preparation of Compound 110a According to Scheme III

Ethyl (2E,4E)-3-methyl-6-[(E)-2,3,5,6,7,8-hexahydro-5,5,8,8-tetramethyl-cyclopenta[b]naphthalen-1-ylidene]hexa-2,4-dienoate (structure 7, where $R_1$, $R_2$, $R_3$, $R_4$, and $R_{19}$ are methyl; $R_5$, $R_6$, $R_7$, $R_8$, $R_9$, and $R_{10}$ are hydrogen; $R_{15}$ is ethoxy; X, Y, and Z are carbon; m=1, n=0).

The title compound was prepared in a manner similar to that of compound 59a except that 2,3,5,6,7,8-hexahydro-5,5,8,8-tetramethylcyclopenta[b]-1-one [U.S. Pat. No. 2.815.382 (1957)] was used in place of 3,4,6,7,8-hexahydro-5,5,8,8-tetramethyl-2H-anthracen-1-one for the NaBH$_4$ reduction step in Example 14. Compound 110a had mp 128°–129° C., $^1$H NMR(400 MHz, CDCl$_3$) δ 7.47 (s, 1H, ArH), 7.23 (s, 1H, ArH), 6.85 (dd, J=11.3, 15.2 Hz, 1H, olefinic), 6.62 (d, J=11.3 Hz, 1H, olefinic), 6.31 (d, J=15.2 Hz, 1H, olefinic), 5.75 (s, 1H, olefinic), 4.17 (q, 2H, OCH$_2$), 3.05–2.85 (m, 4H, 2CH$_2$, benzylic and allylic), 2.45 (s, 3H, CH$_3$), 1.65 (s, 4H, CH$_2$), 1.28 (s, 6H, 2CH$_3$), 1.27 (m, 9H, 3CH$_3$).

EXAMPLE 17

Preparation of Compound 110b According to Scheme III (2E,4E)-3-Methyl-6-[(E)-2,3,5,6,7,8-hexahydro-5,5,8,8-tetramethyl-cyclopenta[b]naphthalen-1-ylidene]hexa-2,4-dienoic acid (structure 7, where $R_1$, $R_2$, $R_3$, $R_4$, and $R_{19}$ are methyl; $R_5$, $R_6$, $R_7$, $R_8$, $R_9$, and $R_{10}$ are hydrogen; $R_{15}$ is hydroxy; X, Y, and Z are carbon; m=1, and n=0).

The title acid was prepared by hydrolysis of compound 110a using the standard hydrolysis conditions in Example 2. Compound 110b had mp 200°–202° C., $^1$H NMR (400 MHz, CDCl$_3$) δ 7.47 (s, 1H, ArH), 7.23 (s, 1H, ArH), 6.92 (dd, J=11.3, 15.1 Hz, 1H, olefinic), 6.63 (d, J=11.3 Hz, 1H, olefinic), 6.35 (d, J=15.1 Hz, 1H, olefinic), 5.79 (s, 1H, olefinic), 3.02–2.91 (m, 4H, 2CH$_2$, benzylic and allylic), 2.37 (s, 3H, CH$_3$), 1.67 (s, 4H, 2CH$_2$), 1.30 (s, 6H, 2CH$_3$), 1.27 (s, 6H, 2CH$_3$).

EXAMPLE 18

Preparation of Compound 111a According to Scheme III

Ethyl (2E,4E)-3-methyl-6-[(E)-1,2,3,6,7,8-hexahydro-1,1,3,3-tetramethylcyclopenta[b]naphthalen-5-ylidene]hexa-2,4-dienoate (structure 7, where $R_1$, $R_2$, $R_3$, $R_4$, and $R_{19}$ are methyl; $R_5$, $R_6$, $R_7$, $R_8$, $R_9$, and $R_{10}$ are hydrogen; $R_{15}$ is ethoxy; X, Y, and Z are carbon; m=0, and n=1).

The title compound was prepared in a manner similar to that of compound 59a except that 1,2,3,6,7,8-hexahydro-1,1,3,3-tetramethylcyclopenta[b]naphthalen-1-one (the preparation of the title ketone is described in example 5) was used as the starting ketone in the NaBH$_4$ reduction step of Example 14. Compound 111a had $R_f$=0.84 (10% ether in hexane); $^1$H NMR (400 MHz, CDCl$_3$) δ 7.4 (s, 1H, ArH), 7.07 (dd, J=15.0, 11.3 Hz, 1H, olefinic), 6.86 (s, 1H, ArH), 6.75 (d, J=11.3 Hz, 1H, olefinic), 6.42 (d, J=15.0 Hz, 1H, olefinic), 5.81 (s, 1H, olefinic), 4.15 (q, 2H, OCH$_2$), 2.82 (t, J=6.0 Hz, 2H, CH$_2$, benzylic), 2.73 (t, J=5.71 Hz, 2H, CH$_2$, allylic), 2.38 (s, 3H, CH$_3$), 1.91 (s, CH$_2$, 2H), 1.89 (m, 2H, CH$_2$), 1.32 (s, 6H, 2Ch$_3$), 1.30 (m, 9H, 3CH$_3$).

EXAMPLE 19

Preparation of Compound 111b According to Scheme III (2E,4E)-3-Methyl-6-[(E)-1,2,3,6,7,8-hexahydro-1,1,3,3-tetramethylcyclopenta[b]-5-ylidene]hexa-2,4-dienoic acid (structure 7, where $R_1$, $R_2$, $R_3$, $R_4$, and $R_{19}$ are methyl, $R_5$, $R_6$, $R_7$, $R_8$, $R_9$, and $R_{10}$ are hydrogen, $R_{15}$ is hydroxy, X, Y, and Z are carbon, m=0, and n=1)

The title compound was prepared from hydrolysis of ester 111a using the standard hydrolysis conditions employed in Example 2. Acid 111b had $R_f$=0.40 (30% ether in hexane), mp 207°–209° C., $^1$H NMR (400 MHz, CDCl$_3$) δ 7.41 (s, 1H, ArH), 7.10 (dd, J=15.0, 11.3 Hz, 1H, olefinic), 6.87 (s, 1H, ArH), 6.77 (d, J=11.3 Hz, 1H, olefinic), 6.45 (d, J=15.0 Hz, 1H, olefinic), 5.84 (s, 1H, olefinic), 2.83 (t, J=6.0 Hz, 2H, CH$_2$, benzylic), 2.73 (t, J=5.7 Hz, 2H, CH$_2$, allylic), 2.40 (s, 3H, CH$_3$), 1.91 (s, 2H, CH$_2$), 1.88 (m, 2H, CH$_2$), 1.34 (s, 6H, 2CH$_3$), 1.30 (s, 6H, 2CH$_3$).

EXAMPLE 20

Preparation of Compound 112a According to Scheme I & III

Ethyl (2Z,4E)-3-methyl-6-[(E)-1,2,3,6,7,8-hexahydro-1,1,3,3-tetramethylcyclopenta[b]naphthalen-5-ylidene]hexa-2,4-dienoate (structure 7, where $R_1$, $R_2$, $R_3$, $R_4$, and $R_{19}$ are methyl; $R_5$, $R_6$, $R_7$, $R_8$, $R_9$, and $R_{10}$ are hydrogen; $R_{15}$ is ethoxy; X, Y, and Z are carbon; m=0, and n=1)

The title compound was obtained as a by-product from the preparation of compound 111a of Example 18. Compound 112a had $R_f$=0.85 (10% ether in hexane); $^1$H NMR (400 MHz, CDCl$_3$) δ 7.92 (d, J=15.2 Hz, 1H, olefinic), 7.46 (s, 1H, ArH), 7.12 (dd, J=15.2, 11.2 Hz, 1H, olefinic), 6.90 (d, J=11.2 Hz, 1H, olefinic), 6.86 (s, 1H, ArH), 5.82 (s, 1H, olefinic), 4.20 (q, 2H, OCH$_2$), 2.90 (t, J=5.9 Hz, 2H, CH$_2$, benzylic), 2.75 (t, J=5.7 Hz, 2H, Ch$_2$, allylic), 2.10 (s, 3H, CH$_3$), 1.95 (s, 2H, CH$_2$), 1.93 (m, 2H, CH$_2$,), 1.32 (s, 6H, 2Ch$_3$), 1.30 (m, 9H, 3CH$_3$).

EXAMPLE 21

Preparation of Compound 112b According to Scheme I (2Z,4E)-3-Methyl-6-[(E)-1,2,3,6,7,8-hexahydro-1,1,3,3-tetramethylcyclopenta[b]naphthalen-5-ylidene]hexa-2,4-dienoic acid (structure 7, where $R_1$, $R_2$, $R_3$, $R_4$, and $R_{19}$ are methyl; $R_5$, $R_6$, $R_7$, $R_8$, $R_9$, and $R_{10}$ are hydrogen; $R_{15}$ is hydroxy; X, Y, and Z are carbon; m=0, and n=1)

The title compound was prepared from hydrolysis of compound 112a using the standard hydrolysis conditions described in Example 2. Compound 112b had $R_f$=0.50 (30% ether in hexane); $^1$H NMR (400 MHz, CDCl$_3$) δ 7.85 (d, J=15.2 Hz, 1H, olefinic), 7.46 (s, 1H, ArH), 7.12 (dd, J=15.2, 11.3 Hz, 1H, olefinic), 6.90 (d, J=11.3 Hz, 1H, olefinic), 6.86 (s, 1H, ArH), 5.69 (s, 1H, olefinic), 2.82 (t, J=6.1 Hz, 2H, CH$_2$, benzylic), 2.23 (t, J=5.9 Hz, 2H, CH$_2$, allylic), 2.14 (s, 3H, CH$_3$), 1.91 (s, 2H, CH$_2$), 1.89 (m, 2H, CH$_2$), 1.25 (s, 6H, 2CH$_3$), 1.22 (s, 6H, 2CH$_3$).

EXAMPLE 22

Preparation of Compound 113b According to Scheme II (2E,4E)-3-Methyl-6-[(E)-3,4,5,6,7,8-hexahydro-4,4,5,5,8, 8-hexamethyl-2H-anthracen-1-ylidene]hexa-2,4-dienoic acid (structure 7, where R$_1$, R$_2$, R$_3$, R$_4$, and R$_{19}$ are methyl; R$_5$, R$_6$, R$_7$, R$_8$, R$_9$, and R$_{10}$ are hydrogen; R$_{15}$ is hydroxy; X and Y are carbon; Z is C(CH$_3$)$_2$; m=n=1).

This compound was prepared starting from 2-[(E)-3,4,5, 6,7,8-hexahydro-2H-4,4,5,5,8,8-hexamethylanthracene-1-ylidine] ethanol as described for the (2E,4E,6Z)-isomer (Examples 10 and 11). Compound 113b had: $^1$H NMR (400 MHz, CDCl$_3$) δ 7.59 (s, 1H, Ar); 7.08 (d J=12 Hz, 1H,), 7.0 (s, 1H, Ar), 6.7 (d, J=12 Hz, 1H), 6.28 (d, J=12 Hz, 1H), 5.82 (s, 1H), 2.7 (t, J=4.5 Hz, 2H), 2.37 (s, 3H, CH$_3$), 1.68 (t, J=4.0 Hz, 2H), 1.66 (s, 4H), 1.3 (s, 18H).

EXAMPLE 23

Preparation of Compounds 114a According to Scheme I

Ethyl (2E,4E,6E)-3-methyl-6-[1,2,3,4,7,8,9,10-octahydro-1, 1,4,4-tetramethyl-6H-naphthocycloheptene-10-yl]hexa-2,4, 6-trienoate (structure 7 where R$_1$, R$_2$, R$_3$, R$_4$ and R$_{19}$ are methyl, R$_5$, R$_6$, R$_7$, R$_8$, R$_9$, and R$_{10}$ are hydrogen; R$_{15}$ is ethoxy; X, Y and Z are carbon; m=1 and n=2).

The title ester was prepared from 1-benzosuberone (Aldrich) according to Scheme I following the representative procedure for compounds 59a and 59b as outlined in Examples 14 and 15. Compound 114a had R$_f$=0.5 (5% EtOAc-hexanes); $^1$H-NMR (400 MHz, CDCl$_3$) δ 7.11 (s, 1H, ArH), 7.00 (s, 1H, ArH), 6.99 (m, 1H, olefinic), 6.33 (d, J=16 Hz, 1H, olefinic), 6.21 (d, J=16 Hz, 1H, olefinic), 5.80 (s, 1H, olefinic), 4.20 (m, 2H, —OCH$_2$CH$_3$), 2.67 (d, J=16 Hz, 4H, 2CH$_2$), 2.39 (s, 3H, CH$_3$), 1.78 (s, 4H, 2CH$_2$), 1.68 (s, 4H, 2CH$_2$), 1.33 (m, 15H, 4CH$_3$;—CH$_2$CH$_3$).

EXAMPLE 24

Preparation of Compound 114b According to Scheme I (2E, 4E, 6E)-3-Methyl-6-[1,2,3,4,7,8,9,10-octahydro-1,1,4, 4-tetramethyl-6H-naphthocycloheptene-10-yl]hexa-2,4,6-trienoic acid. (structure 7 where R$_1$, R$_2$, R$_3$, R$_4$ and R$_{19}$ are methyl; R$_5$, R$_6$, R$_7$, R$_8$, R$_9$, and R$_{10}$, are hydrogen; R$_{15}$ is hydroxy; X, Y and Z are carbon; m=1 and n=2).

The title compound was prepared from ester 114a following the standard hydrolysis procedure as outlined in Example 2. Compound 114b had R$_f$=0.3 (15% EtOAc-hexanes); mp 244°–246° C.; $^1$H-NMR (400 MHz, CDCl$_3$) δ 7.12 (s, 1H, ArH), 7.02 (m, 1H, olefinic), 7.00 (s, 1H, ArH), 6.38 (d, J=16 Hz, 1H, olefinic), 6.25 (d, J=16 Hz, 1H, olefinic), 5.85, (s, 1H, olefinic), 2.72 (t, J=16 Hz, 2H, CH$_2$), 2.62 (t, J=16 Hz, 2H, CH$_2$), 2.40 (s, 3H, Ch$_3$), 1,80 (m, 4H, 2CH$_2$), 1.68 (s, 4H, 2CH$_2$), 1.31 (s, 6H, 2CH$_3$), 1.30 (s, 6H, 2CH$_3$).

EXAMPLE 25

Preparation of Compound 115a According to Scheme I

Ethyl (2Z, 4E, 6E)-3-methyl-6-[1,2,3,4,7,8,9,10-octahydro-1,1,4,4-tetramethyl-6H-naphthocycloheptene-10-yl]hexa-2, 4,6-trienoate (Structure 7, where R$_1$, R$_2$, R$_3$, R$_4$ and R$_{19}$ are methyl, R$_5$, R$_6$, R$_7$, R$_8$, R$_9$, and R$_{10}$ are hydrogen; R$_{15}$ is ethoxy; X, Y and Z are carbon; m=1 and n=2).

The title compound was prepared as a by-product from the synthesis of compound 114a (Example 23). The title compound 115a had R$_f$=0.3 (15% EtOAc-hexanes); $^1$H-NMR (400 MHz, CDCl$_3$) δ 7.82 (d, J=16 Hz, 1H, olefinic), 7.12 (s, 1H, ArH)., 7.00 (s, 1H, ArH), 6.38 (d, J=16 Hz, 1H, olefinic), 5.68 (s, 1H, olefinic), 4.15 (q, J=8 Hz, 2H, —OCH$_2$CH$_3$), 2.65 (d, J=16 Hz, 4H, 2CH$_2$), 2.28 (s, 3H, CH$_3$), 1.72 (s, 4H, 2CH$_2$), 1.68 (s, 4H, 2CH$_2$), 1.23 (s, 6H, 2CH$_3$), 1.27 (s, 6H, 2CH$_3$), 0.9 (t, J=8 Hz, 3H, —OCH$_2$CH$_3$).

EXAMPLE 26

Preparation of Compound 115b According to Scheme I (2Z,4E)-3-Methyl-6-[1,2,3,4,7,8,9,10-octahydro-1,1,4,4-tetramethyl-6H-naphthocycloheptene-10-yl]hexa-2,4,6-trienoic acid (structure 7, where R$_1$, R$_2$, R$_3$, R$_4$, and R$_{19}$ are methyl; R$_5$, R$_6$, R$_7$, R$_8$, R$_9$ and R$_{10}$ are hydrogen; R$_{15}$ is ethoxy; X, Y and Z are carbon; m=1 and n=2).

The title acid was prepared from ester 115a using the hydrolysis procedure outlined in Example 2. Compound 115b had R$_f$=0.5 (10% MeOH-CHCl$_3$); $^1$H-NMR (400 MHz, CDCl$_3$) δ 7.76 (d, J=16 Hz, 1H, olefinic), 7.11 (s, 1H, ArH)., 7.04 (m, 1H, olefinic), 6.99 (s, 1H, ArH), 6.32 (d, J=16 Hz, 1H, olefinic), 5.69 (s, 1H, olefinic), 2.65 (d, J=16 Hz, 4H, 2CH$_2$), 2.10 (s, 3H, CH$_3$), 1.65 (s, 4H, 2CH$_2$), 1.27 (s, 6H, 2CH$_3$), 1.31 (s, 6H, 2CH$_3$).

EXAMPLE 27

Preparation of Compound 116b According to Scheme I (2E,4E)-3-Methyl-6-[(E)-3,5,6,7-tetrahydro-5,5,7,7-tetramethyl-2H-5-indacen-1-ylidene]hexa-2,4-dienoic acid (structure 7, where R$_1$, R$_2$, R$_3$, R$_4$, and R$_{19}$ are methyl; R$_5$, R$_6$, R$_7$, R$_8$, R$_9$ and R$_{10}$ are hydrogen; R$_{15}$ is hydroxy; X, Y and Z are carbon; m=n=0).

The title acid was prepared from 5,5,7,7-tetramethyl-3,5, 6,7-tetrahydro-2H-5-indacen-1-one in a manner similar to that of compound 59b in Example 14. Compound 116b had R$_f$=0.36 (50% ether in hexane), amorphous material; $^1$H NMR(400 MHz, CDCl$_3$) δ: 7.27 (s, 1H, ArH), 7.02 (s, 1H, ArH), 6.92 (dd, J=15.1, 12.5 Hz, 1H, olefinic), 6.68 (a, J=12.5 Hz, 1H, olefinic), 6.35 (d, J=15.1 Hz, 1H, olefinic), 5.89 (s, 1H, olefinic), 3.02 (m, 2H, CH$_2$), 2.98 (m, 2H, CH$_2$), 2.38 (s, 3H, CH$_3$), 1.94 (s, 2H, CH$_2$), 1.32 (s, 6H, 2CH$_3$), 1.30 (s, 6H, 2CH$_3$).

EXAMPLE 28

Preparation of Compound 117a According to Scheme I

Ethyl (2E,4E)-3-methyl-6-[(E)-3,4,5,6,7,8-hexahydro-10-nitro-5,5,8,8-tetramethyl-2H-anthracen-1-ylidene]hexa-2,4-dienoate (structure 7, where R$_1$, R$_2$, R$_3$, R$_4$, and R$_{19}$ are methyl; R$_5$, R$_6$, R$_7$, R$_8$, and R$_{10}$ are hydrogen; R$_9$ is nitro; R$_{15}$ is ethoxy, X, Y, Z are carbon, m=n=1).

The title compound was prepared from 10-nitro-1,2,3,4, 5,6,7,8-octahydro-5,5,8,8-tetramethylanthracen-1-one (of Example 8) using a procedure similar to that described in Example 1. Compound 117a was obtained as a yellow oil: $^1$H NMR (400 MHz, CDCl$_3$) δ 7.72 (s, 1H, aromatic), 7.01 (dd, J=15.1, 11.2 Hz, 1H, olefinic), 6.72 (d, J=1 1.2 Hz, 1H, olefinic), 6.46 (d, J=15.1 Hz, 1H, olefinic), 5.84 (s, 1H, olefinic), 4.19 (q, J=7.1 Hz, 2H, —OCH$_2$), 2.67 (br t, J=5.6

Hz, 2H, CH$_2$), 2.55 (t, J=6.3 Hz, 2H, CH$_2$), 2.37 (d, J=1.0 Hz, 3H, CH$_3$ allylic), 1.85 (app quintet, J=6.3 Hz, 2H, CH$_2$), 1.75 (m, 2H, CH$_2$), 1.67 (m, 2H, CH$_2$), 1.35 (s, 6H, 2CH$_3$), 1.32 (s, 6H, 2CH$_3$), 1.30 (t, J=7.1 Hz, 3H, CH$_3$ ethyl).

EXAMPLE 29

Preparation of Compound 117b According to Scheme I (2E,4E)-3-Methyl-6-[(E)-3,4,5,6,7,8-hexahydro-10-nitro-5, 5,8,8-tetramethyl-2H-anthracen-1-ylidene]hexa-2,4-dienoic acid (structure 7, where R$_1$, R$_2$, R$_3$, R$_4$, and R$_{19}$ are methyl; R$_5$, R$_6$, R$_7$, R$_8$, and R$_{10}$ are hydrogen; R$_9$ is nitro; R$_{15}$ is hydroxy, X, Y, Z are carbon, m=n=1).

The title acid was prepared from compound 117a using standard hydrolysis conditions outlined in Example 2. Compound 117b was obtained as a yellow solid (75% yield): $^1$H NMR (400MHz, CDCl$_3$) δ 7.73(s, 1H,aromatic), 7.02 (br t, 1H, olefinic), 6.70(d, J=11.1 Hz, 1H, olefinic), 6.49 (d, J=14.9 Hz, 1H, olefinic), 5.86 (s, 1H, olefinic), 2.68 (br t, 2H, CH$_2$), 2.55 (br t, 2H, CH$_2$), 2.36 (s, 3H, CH$_3$ allylic), 1.86 (m, 2H, CH$_2$), 1.74 (m, 2H, CH$_2$), 1.69 (m, 2H, CH$_2$), 1.35 (s, 6H, 2CH$_3$), 1.32 (s, 6H, 2CH$_3$).

EXAMPLE 30

Preparation of Compound 118b According to Scheme I (2Z,4E)-3-Methyl-6-[(E)-3,4,5,6,7,8-hexahydro-10-nitro-5, 5,8,8-tetramethyl-2H-anthracen-1-ylidene]hexa-2,4-dienoic acid (structure 7, where R$_1$, R$_2$, R$_3$, R$_4$, and R$_{19}$ are methyl; R$_5$, R$_6$, R$_7$, R$_8$, and R$_{10}$ are hydrogen; R$_9$ is nitro; R$_{15}$ is hydroxy, X, Y, Z are carbon, m=n=1).

Obtained as a by-product from synthesis of compound 117a (Example 28) after hydrolysis of the ester using conditions outlined in Example 2. Compound 118b had $^1$H NMR (400 MHz, CDCl$_3$) δ 7.91 (d, J=15.2 Hz, 1H, olefinic), 7.74 (s, 1H, aromatic), 7.02 (br t, 1H, olefinic), 6.81 (d, J=11.4 Hz, 1H, olefinic), 5.78 (br s, 1H, olefinic), 2.67 (br t, J=6.2 Hz, 2H, CH$_2$), 2.55 (t, J=6.2 Hz, 2H, CH$_2$), 2.11 (s, 3H, CH$_3$ allylic), 1.85 (m, 2H, CH$_2$), 1.74 (m, 2H, CH$_2$), 1.68 (m, 2H, CH$_2$), 1.35 (s, 6H, 2CH$_3$), 1.32 (s, 6H, 2CH$_3$).

EXAMPLE 31

Preparation of Compound 119b According to Scheme I and Scheme IV (2E,4E)-3-Methyl-6-[(E)-2,3,6,7,8,9-hexahydro-6,6,9,9-tetramethyl-benzo[g]chromen-4-ylidene]hexa-2,4-dienoic acid (structure 7, where R$_1$, R$_2$, R$_3$, R$_4$, and R$_{19}$ are methyl; R$_5$, R$_6$, R$_7$, R$_8$, R$_9$, R$_{10}$ are hydrogen; R$_{15}$ is hydroxy; X and Y are carbon; Z is oxygen; m=n=1).

In a manner similar to that described in Example 7 above, an isomeric mixture of (E, Z)-(chromen-4-ylidene) acetonitrile (550mg, 3.5 mmol) was converted to (E)-(2,3, 6,7,8,9-hexahydro-6,6,9,9-tetramethylbenzo[g]chromen-4-ylidene)acetonitrile. Flash chromatography (20% EtOAc/hexanes) of the crude brown solid gave the tricyclic nitrile as a light yellow solid (511 mg 1.82 mmol, 52%): $^1$H NMR (400 MHz, CDCl$_3$) δ 7.4 (s, 1H), 6.82 (s, 1H), 5.7 (s, 1H), 4.25 (t, 2H), 3.0 (t, 2H), 1.67 (s, 4H), 1.26 (s, 6H), 1.24 (s, 6H).

The tricyclic nitrile (1.85 g, 6.6 mmol) was then converted to (E)-(2,3,6,7,8,9-hexahydro-6,6,9,9-tetramethylbenzo[g] chromen-4-ylidene)acetaldehyde using CH$_2$Cl$_2$ as solvent in place of THF. The crude brown oil was purified by flash chromatography (20% EtOAc/hexane) to give the aldehyde as a yellow/orange solid (640 mg, 2.3 mmol, 40%): $^1$H NMR (400 MHz, CDCl$_3$) δ 10.12 (d, 1H ), 7.6 (s, 1H), 6.82 (s, 1H), 6.55 (d, 1H), 4.30 (t, 2H, 3.25 (t, 2H), 1.68 (s, 4 H ), 1.25 (s, 12H).

The tricyclic aldehyde (640 mg, 2.2 mmol) was then transformed to a mixture of ethyl (2E,4E)- and (2Z,4E)-3-methyl-6-[(E) 2,3,6,7,8,9-hexahydro-6,6,9,9-tetramethyl-benzo[g]chromen-4-ylidene]hexa-2,4-dienoates. NaH was used in place of n-BuLi and 2 equivalents of phosphonate and base were used. The aldehyde was added at 0° C. and warmed to 15° C. over 1 h. Aqueous work up (and Et$_2$O extraction) gave the esters as a yellow oil (820 mg, 2.08 mmol, 93%). Flash chromatography (8% EtOAc/hexane) gave the trans -isomer as a yellow solid (191 mg): $^1$H NMR (400 MHz, CDCl$_3$) δ 7.55 (s, 1H), 6.95 (dd, 1H), 6.8 (s, 1H), 6.72 (d, 1H), 6.42 (d, 1H ), 5.80 (s, 1H), 4.20 (m, 4H), 2.8 (t, 2H), 2.36 (s, 3 H ), 1.68 (s, 4 H), 1.3 (t, 3H ), 1.27 (s, 12H ).

Using the procedure of Example 7, the above ester (191 mg, 0.48 mmol) was converted into the title acid. Compound 119b was obtained as a yellow solid (168 mg, 45 mmol, 96%): TLC R$_f$=0.20 (40% Et$_2$O/Hexane); mp 198.2° C.; $^1$H NMR (400 MHz, CDCl$_3$) δ 7.55 (s, 1H), 6.95 (dd, 1H), 6.8 (s, 1H), 6.72 (d, 1H), 6.42 (d, 1H), 5.80 (s, 1H), 4.20(m, 2H), 2.8 (t, 2H), 2.36 (s, 3H), 1.68 (s, 4H), 1.27 (s, 12H).

EXAMPLE 32

Preparation of Compound 120b According to Schemes II and IV (2Z,4E)-3-Methyl-6-[(E)-2,3,6,7,8,9-hexahydro-6,6,9,9-tetramethylbenzo[g]chromen-4-ylidene]hexa-2,4-dienoic acid (structure 7, where R$_1$, R$_2$, R$_3$, R$_4$, and R$_{19}$ are methyl; R$_5$, R$_6$, R$_7$, R$_8$, R$_9$, R$_{10}$ are hydrogen; R$_{15}$ is hydroxy; X and Y are carbon; Z is oxygen; m=n=1).

The isomeric mixture of esters described above in Example 31 was purified by flash chromatography (8% EtOAc/hexane) to give ethyl(2Z,4E)-3-methyl-6-[(E)2,3,6, 7,8,9-hexahydro-6,6,9,9-tetramethyl-benzo[g]chromen-4-ylidene]hexa-2,4-dienoate as a yellow oil (131 mg): $^1$H NMR (400 MHz, CDCl$_3$) δ 7.95 (d, 1H), 7.58 (s, 1H), 6.95 (dd, 1H), 6.85 (d, 1H), 6.80 (s, 1H), 5.67 (s, 1H), 4.20 (m, 4H), 2.8 (t, 2H), 2.10 (s, 3H), 1.68 (s, 4 H), 1.3 t, 3H), 1.27 (s, 12H).

Employing the procedure described in Example 2, the above ester (131 mg, 0.33 mmol) was converted to the title acid. Acid 120b was obtained as a yellow oily solid (108mg, 29.7 mmol, 90%): TLC R$_f$=0.28 (40% Et$_2$O/Hexane); $^1$H NMR (400 MHz, CDCl$_3$) δ 7.95 (d, 1H), 7.58 (s, 1H), 6.95 (dd, 1H), 6.85 (d, 1H), 6.80 (s, 1H), 5.67 (s, 1H), 4.20 (m, 2H), 2.8 (t, 2H), 2.10 (s, 3H), 1.68 (s, 4 H), 1.27 (s, 12H).

EXAMPLE 33

Preparation of Compound 121b According to Schemes I and II (2E,4E)-3-Methyl-6-[(E)-2,3,6,7,8,9-hexahydro-2,2,6,6,9, 9-hexamethyl-benzo[g]chromen-4-ylidene]hexa-2,4-dienoic acid (structure 7, where R$_1$, R$_2$, R$_3$, R$_4$, R$_7$, R$_8$, and R$_{19}$ are methyl; R$_5$, R$_6$, R$_9$, R$_{10}$ are hydrogen; R$_{15}$ is hydroxy; X and Y are carbon; Z is oxygen; m=n=1).

Using the procedure described in Example 31, 2-[(E)-3, 4,5,6,7,8-hexahydro-2,2,5,5,8,8-hexamethylnaphtho-(2,3-b) -1,2 pyran-4-ylidene]ethanitrile (500 mg, 1.6 mmol) was reduced with DIBAL in CH$_2$Cl$_{12}$ to give the corresponding aldehyde. Aqueous work up gave 2-(E)-[3,4,5,6,7,8-hexahydro-2,2,5,5,8,8-hexamethylnaphtho-(2,3-b)-1, 2-pyran-4-ylidene]acetaldehyde which was purified by flash chromatography (8% EtOAc/hexane) to afford a light yellow solid (220mg, 0.71 mmol, 45% yield): $^1$H NMR (400 MHz, CDCl$_3$) δ 10.1 (d, 1H), 7.52 (s, 1H), 6.8 (s, 1H), 6.60 (d, 1H), 3.05 (s, 2H), 1.70 (s, 4H), 1.4 (s, 6H), 1.25 (s, 12H).

The above aldehyde was converted to the corresponding triene ester in a manner similar to that described in Example 23. Aqueous work up gave a yellow oil which partially solidified on standing. Flash chromatography (20% EtOAc/hexane) afforded ethyl (2E,4E)-3-methyl-6-[(E)-5,6,7,8-tetrahydro-5,5,8,8-tetramethyl naphthyl (2,3-b ) 2,2-dimethylpyran-4-yl]hexa-2,4-dienoate as a bright yellow solid (115 mg, 0.27 mmol, 83% yield): $^1$H NMR (400 MHz, CDCl$_3$) δ 7.50 (s, 1H), 6.95 (dd, 1H), 6.75 (m, 2H), 6.45 (d, 1H), 5.8 (s, 1H), 4.10 (m, 2H), 2.66 (s, 2H), 2.39 (s, 3H), 1.65 (s, 4H), 1.33 (s, 6H), 1.31 (t, 3H), 1.30 (s, 6H), 1.25 (s, 6H).

The above ester (60.5mg, 0.143 mmol) was hydrolyzed to the corresponding acid using the procedure described in Example 2 to give the title compound as a bright yellow solid (50 mg, 0.127 mmol , 88%): TLC R$_f$=0.10 (20% EtOAc/Hexane); $^1$H NMR (400 MHz, CDCl$_3$) δ 7.50 (s, 1H), 7.02 (dd, 1H), 6.79 (d, 11H), 6.75(s, 1H), 6.50 (d, 1H), 5.87 (s, 1H), 2.66 (s, 2H ), 2.40(s, 3H ), 1.68(4s, H), 1.38(s, 6H), 1.30 (s, 6H), 1.25 (s, 6H).

EXAMPLE 34

Preparation of Compound 122a According to Scheme V

Ethyl (2E,4E)-3-methyl-6-(3,4,5,6,7,8-hexahydro-5,5,8,8-tetramethylanthracen-1-yl) hexa-2,4-dienoate (structure 20, where R$_1$, R$_2$, R$_3$, R$_4$, and R$_{19}$ are methyl; R$_5$, R$_7$, R$_8$, R$_9$, and R$_{10}$ are hydrogen; R$_{15}$ is ethoxy; X, Y, and Z are carbon; m=n=1).

To a solution of trimethyl phosphonoacetate (5.68 g, 31 mmol) in THF (15 ml) was added dropwise nBuLi (9.3 ml, 2.5 M, 23 mM) at 0° C., and the resulting solution was stirred at that temperature for 30 min. 3,4,5,6,7,8-hexahydro-5,5,8,8-tetramethyl-2H-anthracen-1-one (2.0 g, 7.8 mmol) in THF (10 ml) was added at 25° C., and the mixture was stirred at that temperature for 30 min. Standard work-up procedures as detailed in Example 1, followed by purification of the product by column chromatography (10% ether in hexane) gave methyl (3,4,5,6,7,8-hexahydro-5,5,8, 8-tetramethylanthracen-1-yl)acetate (1.33 g, 55%): $^1$H NMR (400 MHz, CDCl$_3$) δ 7.15 (s, 1H, ArH), 7.04 (s, 1H, ArH), 5.94 (br t, 1H, olefinic), 3.68 (s, 2H, OCH$_3$), 3.43 (s, 2H, CH$_2$), 2.74 (t, J=7.9 Hz, 2H, CH$_2$, benzylic), 2.31 (m, CH$_2$, 2H, allylic), 1.66 (s, 4H, 2CH$_2$), 1.27 (s, 12H, 4CH$_3$).

To a solution of the above methyl ester (312 mg, 1 mmol) in CH$_2$Cl$_2$ (5 ml) was added dropwise DIBAL (1 ml, 1M, 1.0 mM) at −78° C. The resulting mixture was stirred at −78° C. for 30 min, then warmed to room temperature, followed by standard work-up procedure as described in Example 1. Purification of the corresponding aldehyde by chromatography (10% ether in hexane) gave pure (3,4,5,6,7,8-hexahydro-5,5,8,8-teramethylanthracen-1 -yl)-acetaldehyde (140 mg, 50%): $^1$H NMR(400 MHz, CDCl$_3$) δ 9.64 (t, J=2.6 Hz, 1H, CHO), 7.07 (s, 1H, ArH), 7.03 (s, 1H, ArH), 5.98 (br t, 1H, olefinic), 3.44 (s, 2H, CH$_2$), 2.77 (t, J=7.9 Hz, 2H, CH$_2$, benzylic), 2.35 (m, 2H, CH$_2$, allylic), 1.66 (s, 4H, 2CH$_2$), 1.27 (s, 6H, 2CH$_3$), 1.26 (s, 6H, 2CH$_3$).

The above aldehyde was coupled with the anoin of diethyl 3-ethoxycarbonyl-2-methylprop-2-enylphosphonate, as described for compound 51a in Example 1, to give the title compound 122a: R$^f$=0.25 (10% ether in hexane) $^1$H NMR (400 MHz, CDCl$_3$) δ 7.15 (s, 1H, ArH), 7.09 (s, 1H, ArH), 6.07 (m, 2H, olefinic), 5.85 (s, 1H, olefinic), 5.65 (br t, 1H, olefinic), 4.02 (q, 2H, OCH$_2$), 3.12 (br d, 2H, CH$_2$, allylic), 2.61 (t, J=7.8 Hz, 2H, CH$_2$, benzylic), 2.30 (s, 3H, CH$_3$), 2.09 (m, 2H, CH$_2$, allylic), 1.60 (s, 4H, 2CH$_2$), 1.27 (s, 6H, 2CH$_3$), 1.24 (s, 6H, 2CH$_3$), 0.98 (t, J=7.0 Hz, 3H, CH$_3$).

EXAMPLE 35

Preparation of Compound 122b According to Scheme V (2E,4E)-3-Methyl-6-(3,4,5,6,7,8-hexahydro-5,5,8,8-tetramethylanthracen-1-yl)-hexa-2,4-dienoic acid (structure 20a, where R$_1$, R$_2$, R$_3$, R$_4$, and R$_{19}$ are methyl; R$_5$, R$_7$, R$_8$, R$_9$, and R$_{10}$ are hydrogen; R$_{15}$ is hydroxy; X, Y, and Z are carbon; m=n=1).

The title compound was prepared by hydrolysis of compound 122a using the standard conditions described in Example 2. Compound 122b had mp 171°–173° C., $^1$H NMR (400 MHz, CDCl$_3$) δ 7.15 (s, 1H, ArH), 7.06 (s, 1H, ArH), 6.26 (m, 2H, olefinic), 5.81 (brt, 1H, olefinic), 5.74 (s, 1H, olefinic), 3.30 (br s, 2H, CH$_2$, allylic), 2.72 (t, J=8.0 Hz, 2H, CH$_2$, benzylic), 2.27 (m, 2H, CH$_2$, allylic), 2.26 (s, 3H, CH$_3$), 1.66 (s, 4H, 2CH$_2$), 1.25 (s, 6H, 2Ch$_3$), 1.24 (s, 6H, 2CH$_3$).

EXAMPLE 36

Preparation of Compound 123b According to Scheme V (3E,5E)-3-Methyl-6-(3,4,5,6,7,8-hexahydro-5,5,8,8-tetramethylanthracen-1-yl)hexa-3,5-dienoic acid (structure 20b, where R$_1$, R$_2$, R$_3$, R$_4$, and R$_{19}$ are methyl; R$_5$, R$_6$, R$_7$, R$_8$, R$_9$, and R$_{10}$ are hydrogen; R$_{15}$ is hydroxy; X, Y, and Z are carbon; m=n=1)

The title compound was prepared as a by-product from the hydrolysis of compound 122a of Examples 34 and 35. Compound 123b had R$_f$=0.30 (50% ether in hexane); mp 183°–185° C.; $^1$H NMR: (400 MHz, CDCl$_3$) δ 7.32 (s, 1H, ArH), 7.10 (s, 1H, ArH), 7.07 (d, J=10.8 Hz, 1H, olefinic), 6.78 (dd, J=15.8, 10.8 Hz, 1H, olefinic), 6.43 (d, J=15.8 Hz, 1H, olefinic), 6.15 (br t, 1H, olefinic), 3.15 (s, 2H, CH$_2$, α-methylene), 2.69 (t, J=7.5 Hz, 2H, CH$_2$, benzylic), 2.30 (m, 2H, CH$_2$, allylic), 1.90 (s, 3H, CH$_3$), 1.68 (s, 4H, 2CH$_2$), 1.30 (s, 6H, 2CH$_3$), 1.29 (s, 6H, 2CH$_3$).

EXAMPLE 37

Preparation of Compound 124a According to Scheme VI

Ethyl (2E,4E)-3-methyl-6-(1,2,3,4,5,6,7,8-octahydro-5,5,8, 8-tetramethylanthracen-1-yl)-hexa-2,4-dienoate (structure 22, where R$_1$, R$_2$, R$_3$, R$_4$, and R$_{19}$ are methyl; R$_5$, R$_6$, R$_7$, R$_8$, R$_9$, and R$_{10}$ are hydrogen; R$_{15}$ is ethoxy; X, Y, and Z are carbon; m=n=1).

To a solution of [(E)-3,4,5,6,7,8,9-hexahydro-5,5,8,8-tetramethyl-2H-anthracen-1-ylidene]ethanitrile (56 mg, 0.2 mmol from Example 1) in EtOAc (5 ml) was added 5 mg of 10% Pd-C catalyst, and the reaction mixture was treated with hydrogen gas at 1 atm for 3 h. Removal of the catalyst by filtration, and concentration of organic solvent gave essentially pure saturated nitrile which was used for the next reaction without further purification. The saturated nitrile was then sequentially subjected to DIBAL reduction and Wittig coupling reaction using conditions similar to those described in Example 1 to afford, after column chromatography, the title compound 124a: R$_f$=0.55(10% ether in hexane); $^1$H NMR(400 MHz, CDCl$_3$) δ 7.09 (s, 1H, ArH), 6.98 (s, 1H, ArH), 6.20 (m, 1H, olefinic), 6.12 (d, J=15.7 Hz, 1H, olefinic), 5.70 (s, 1H, olefinic), 4.13 (q, 2H, OCH$_2$), 2.85 (m, 1H, CH), 2.79 (br t, 2H, CH$_2$, benzylic), 2.60 (m, 1H, CH, allylic), 2.37 (m, 1H, CH, allylic), 2.30 (s, 3H, CH$_3$), 1.80 (m, 2H, CH$_2$, methylene), 1.65 (m, 2H, CH$_2$, methylene), 1.63 (s, 6H, 2CH$_2$), 1.27 (s, 6H, 2CH$_3$), 1.26 (s, 6H, 2CH$_3$), 1.26 (t, J=6.8 Hz, 3H, CH$_3$).

EXAMPLE 38

Preparation of Compound 124b According to Scheme VI (2E,4E)-3-Methyl-6-(1,2,3,4,5,6,7,8-octahydro-5,5,8,8-tetramethylanthracen-1-yl)hexa-2,4-dienoic acid (structure 22, where R$_1$, R$_2$, R$_3$, R$_4$, and R$_{19}$ are methyl; R$_5$, R$_6$, R$_7$, R$_8$, R$_9$, and R$_{10}$ are hydrogen; R$_{15}$ is hydroxy; X, Y, and Z are carbon; m=n=1).

Compound 124a was subjected to hydrolysis using the standard conditions of Example 2 to obtain the title acid 124b: R$_f$=0.48(50% ether in hexane); mp 178°–179° C.; $^1$NMR(400 MHz, CDCl$_3$) δ 7.07 (s, 1H, ArH), 6.98 (s, 1H, ArH). 6.23 (m, 1H, olefinic), 6.15 (d, J=15.6 Hz, 1H, olefinic), 5.72 (s, 1H, olefinic), 2.86 (m, 1H), 2.70 (br t, 2H, CH$_2$, benzylic), 2.60 (m, 1H, allylic), 2.42 (m, 1H, allylic), 2.30 (s, 3H, CH$_3$), 1.80 (m, 2H, CH$_2$, methylene), 1.68 (m, 2H, CH$_2$, methylene), 1.64 (s, 4H, 2CH$_2$), 1.25 (s, 6H, 2CH$_3$), 1.24 (s, 6H, 2CH$_3$).

EXAMPLE 39

Preparation of Compound 125a According to Scheme VI

Ethyl (2E,4E)-3-methyl-6-(1,2,3,5,6,7,8-heptahydro-5,5,8,8-tetramethyl-cyclopenta[b]napthalen-1-yl)hexa-2,4-dienoate (structure 22, where R$_1$, R$_2$, R$_3$, R$_4$, and R$_{19}$ are methyl, R$_5$, R$_6$, R$_7$, R$_8$, R$_9$, R$_{10}$ are hydrogen, R$_{15}$ is ethoxy, X, Y, Z are carbon, m=1, and n=0).

The title compound was prepared in a manner similar to that of compound 124a except that 2-[(E)-2,3,5,6,7,8-hexahydro-5,5,8,8-tetramethyl-cyclopenta[b]naphthalen-1-ylidene]ethanitrile was employed as the starting material. The starting nitrile was prepared by condensation of 2,3,5,6,7,8hexahydro-5,5,8,8-tetramethyl-cyclopenta[b]indan-1-one (U.S. Pat. No. 2,815,382 (1957)) with the sodium anion of cyanomethylphosphonate. Title compound 125a had R$_f$=0.50 (10% ether in hexane); $^1$H NMR(400 MHz, CDCl$_3$) δ 7.15 (s, 1H, ArH), 7.12 (s, 1H, ArH), 6.20 (m, 1H, olefinic), 6.15 (d, J=15.7 HZ, 1H, olefinic), 5.69 (s, 1H, olefinic), 4.14 (q, 2H, OCH$_2$), 3.15 (m, 1H, CH), 2.85 (m, 1H, benzylic), 2.75 (m, 1H, benzylic), 2.65 (m, 1H, allylic), 2.32 (m, 1H, allylic), 2.27 (s, 3H, CH$_3$), 2.20 (m, 1H, methylene), 1.69 (m, 1H, methylene), 1.65 (s, 4H, 2CH$_2$), 1.26 (s, 6H, 2CH$_3$), 1.24 (m, 9H, 3CH$_3$).

EXAMPLE 40

Preparation of Compound 125b According to Scheme VI (2E,4E)-3-Methyl-6-1,2,3,5,6,7,8-heptahydro-5,5,8,8-tetramethyl-cyclopenta[b]naphthalen-1-yl)hexa-2,4-dienoic acid (structure 22, where R$_1$, R$_2$, R$_3$, R$_4$, and R$_{19}$ are methyl; R$_5$, R$_6$, R$_7$, R$_8$, R$_9$, and R$_{10}$ are hydrogen; R$_{15}$ is hydroxy; X, Y, and Z are carbon; m=1, and n=0).

The title compound was prepared by hydrolysis of compound 125a using the standard condition of Example 2. Compound 125b had R$_f$=0.48(50% ether in hexane); mp 169°–170° C.; $^1$H NMR(400 MHz, CDCl$_3$) δ 7.16 (s, 1H, ArH), 7.12 (s, 1H, ArH), 6.24 (m, 1H, olefinic), 6.18 (d, J=15.7 Hz, 1H, olefinic), 5.72 (s, 1H, olefinic), 3.18 (m, 1H, methine), 2.85 (m, 1H, benzylic), 2.78 (m, 1H, benzylic), 2.65 (m, 1H, allylic), 2.33 (m, 1H, allylic), 2.29 (s, 3H, CH$_3$), 2.17 (m, 1H, methylene), 1.70 (m, 1H, methylene), 1.65 (s, 4H, 2CH$_2$), 1.27 (s, 6H, 2CH$_3$), 1.25 (s, 6H, 2CH$_3$).

EXAMPLE 41

Preparation of Compound 126a According to Scheme VI

Ethyl (2E,4E)-3-methyl-6-[1,2,3,4,7,8,9,10-octahydro-1,1,4,4-tetramethyl-6H-naphthocycloheptan-10-yl]hexa-2,4-dienoate (structure 22 where R$_1$, R$_2$, R$_3$, R$_4$ and R$_{19}$ are methyl; R$_5$, R$_6$, R$_7$, R$_8$, R$_9$, and R$_{10}$, are hydrogen; R$_{15}$ is ethoxy; X, Y and Z are carbon; m=1 and n=2)

To 11.0 g of diethyl cyanomethylphosphonate in 16 mL of dry THF was added 1.97 g of NaH to 25° C. The solution was stirred for 50 minutes, followed by addition of 4 g of 1-benzosuberone (Aldrich) in 5 mL of dry THF. The reaction was warmed to 80° C. for 12–16 h, cooled to room temperature and poured into saturated NH$_4$Cl solution. The products were extracted with EtOAc, washed with H$_2$O and brine, dried over MgSO$_4$, filtered and concentrated. The crude product was purified by chromatography (SiO$_2$, 10% EtOAc-hexanes) to give 4.1 g of (E)-2-[2-cyanomethenyl]benzosubarane: $^1$H-NMR (400 MHz, CDCl$_3$) δ 7.12–7.32 (m, 4H, ArH), 5.31 (s, 1H, olefinic), 2.75–2.78 (m, 4H, 2CH$_2$), 1.90 (m, 2H, CH$_2$), 1.80 (m, 2H, CH$_2$).

To 2.1 g of (E)-2-[2-cyanomethenyl]benzosubarane in 20 mL of CH$_2$Cl$_2$ and 3.15 g of dichlorodimethylhexane at 25° was added 3.06 g of aluminum trichloride. The mixture was stirred for 10 minutes, poured into H$_2$O, and the product was extracted with 20% EtOAc-hexanes. The organic layer was washed with H$_2$O and brine, dried over MgSO$_4$, filtered and concentrated. Purification by chromatography (SiO$_2$, hexanes) gave 1.8 g of pure 2-[1,1,4,4-tetramethyl-1,2,3,4,7,8,9,10-octahydro-6H-naphthocycloheptan-10-yl]cyanomethylene: $^1$NMR (400 MHz, CDCl$_3$) δ 7.02 (s, 1H, ArH), 7.01 (s, 1H, ArH), 5.30 (s, 1H, CH), 2.78 (t, J=12 Hz, 2H, CH$_2$), 2.70 (t, J=12 Hz, 2H, CH$_2$), 1.85 (m, 2H, CH$_2$), 1.75 (m, 2H, CH$_2$), 1.60 (s, 4H, 2CH$_2$), 1.27 (s, 6H, 2CH$_3$), 1.23 (s, 6H, 2CH$_3$).

To 614 mg (2.10 mmol) of the above nitrile in CH$_2$Cl$_2$ (8 ml) at −78° C. was added 1.68 mL (1.5 molar solution) of DIBAL. The mixture was stirred for 20 minutes at −78° C., then poured onto potassium-sodium tartrate solution, acidified with 1N HCl, and the product extracted with ether. The ether layer was washed with H$_2$O, brine, dried over MgSO$_4$, filtered and concentrated. The crude product was purified by silica gel flash chromatography (5% EtOAc-hexanes) to give 412 mg of [1,2,3,4,7,8,9,10-octahydro-1,1,4,4-tetramethyl-6H-naphthocycloheptan-10-yl]ethenal: $^1$H-NMR (400 MHz, CDCl$_3$) δ 10.12 (d, J=12 Hz, 1H, CHO), 7.12 (s, 1H, ArH), 7.00 (s, 1H, ArH), 6.10 (d, J=12 Hz, 1H, olefinic), 2.92 (t, J=16 Hz, 2H, CH$_2$), 2.72 (t, J=16 Hz, 2H, CH$_2$), 1.87 (m, 2H, CH$_2$), 1.80 (m, 2H, CH$_2$), 1.68 (s, 4H, 2CH$_2$), 1.27 (s, 6H, 2CH$_3$), 1.23 (s, 6H, 2CH$_3$).

To 150 mg of aldehyde in EtOAc (3 ml) was added 15 mg of 10% Pd/C, and the mixture was stirred under one atmosphere of H$_2$ gas for 2 hours, then filtered through a silica gel plug, and concentrated to give 140 mg of (1,2,3,4,7,8,9,10-octahydro-1,1,4,4-tetramethyl-6H-naphthocycloheptan-10-yl)ethanal: R$_f$=0.4 (10% EtOAc-hexanes); $^1$H-NMR (400 MHz, CDCl$_3$) δ 9.80 (s, 1H, CHO), 6.95 (s, 1H, ArH), 6.90 (s, 1H, ArH), 3.70 (m, 2H, CH$_2$), 3.50 (m, 1H, CH), 3.00 (m, 2H, CH$_2$), 2.6–2.8 (m, 2H, CH$_2$), 1.80 (m, 4H, 2CH$_2$), 1.60 (s, 4H, 2CH$_2$), 1.32 (s, 6H, 2CH$_3$), 1.28 (s, 6H, 2CH$_3$).

To 372 mg of triethyl 3-methyl-4-phosphonocrotonate in 14 mL of dry 2:1 anhydrous THF-DMPU at −78° C. was added 0.57 mL of a 2.5M nBuLi solution in THF. The reaction was stirred for 10 minutes at −78° C., followed by addition of 140 mg of the above (1,1,4,4-tetramethyl-1,2,3, 4,7,8,9,10-octahydro-6H-naphthocyclohept ene-10-yl) ethanal in 3 mL of dry THF. The reaction was stirred for an additional 10 minutes at −78° C., then warmed to room temperature. The reaction was poured into saturated $NH_4Cl$ and the product extracted with ether. The ether layer was washed with $H_2O$ and brine, dried over $MgSO_4$, filtered and concentrated. The crude product was purified by preparative TLC ($SiO_2$, 5% EtOAc-hexanes) to give 140 mg of the title ester 126a: $R_f$=0.6, (5% EtOAc-hexanes); $^1$H-NMR (400 MHz, $CDCl_3$) δ 6.99 (s, 2H, ArH), 6.13 (m, 2H, olefinic), 5.65 (s, 1H, olefinic), 4.12 (m, 2H —$OCH_2CH_3$), 2.91 (m, 2H, $CH_2$), 2.81 (t, J=16 Hz, 2H, $CH_2$), 2.70 (m, 1H, CH), 2.56 (m, 2H, $CH_2$), 1.68 (s, 4H, $2CH_2$), 1.20–1.30 (m, 15H, $OCH_2CH_3$+$4CH_3$). A small amount (40 mg) of the corresponding Z,E-isomer was obtained as well.

EXAMPLE 42

Preparation of Compound 126b According to Scheme VI (2E,4E)-3-Methyl-6-[1,1,4,4-tetramethyl-1,2,3,4,7,8,9,10-octahydro-6H-naphthocycloheptan-10-yl]hexa-2,4-dienoic acid. (structure 22, where $R_1$, $R_2$, $R_3$, $R_4$ and $R_{19}$ are methyl; $R_5$, $R_6$, $R_7$, $R_8$, $R_9$, and $R_{10}$, are hydrogen; $R_{15}$ is hydroxy; X, Y and Z are carbon; m=1 and n=2)

Compound 126a (15 mg) was hydrolyzed by the standard method described in Example 2. The title compound was crystallized from EtOAc-hexanes to give 8.2 mg of 126b: $R_f$=0.3 (15% EtOAc-hexanes); $^1$H-NMR (400 MHz, $CDCl_3$) δ 7.00 (s, 2H, ArH), 6.19 (m, 2H, olefinic), 5.70 (s, 1H, olefinic), 2.91 (m, 2H, CH), 2.80 (t, J=16 Hz, 2H, $CH_2$), 2.70 (m, 1,H CH), 2.51 (m, 2H, $CH_2$), 2.21 (s, 3H, $CH_3$), 1.70 (m, 4H, $2CH_2$), 1.61 (s, 4H, $2CH_2$), 1.20–1.22 (m, 12H, $4CH_3$).

EXAMPLE 43

Preparation of Compounds 127a and 127b According to Scheme VI

Ethyl (2Z,4E)-3-methyl-6-[1,2,3,4,7,8,9,10-octahydro-1,1,4,4-tetramethyl-6H-naphthocycloheptan-10-yl]hexa-2,4-dienoate. (structure 22, where $R_1$, $R_2$, $R_3$, $R_4$ and $R_{19}$ are methyl; $R_5$, $R_6$, $R_7$, $R_8$, $R_9$, and $R_{10}$ are hydrogen; $R_{15}$ is ethoxy; X, Y and Z are carbon; m=1 and n=2)

Prepared as a minor by-product from Example 41. Compound 127a had $R_f$=0.6; (5% EtOAc-hexanes); $^1$H-NMR (400 MHz, $CDCl_3$) δ 7.66 (d, J=16 Hz, 1H, olefinic), 6.98 (s, 2H, ArH), 6.13 (m, 1H, olefinic), 5.58 (s, 1H, olefinic), 4.42 (m, 2H, $OCH_2CH_3$), 2.91 (m, 2H, CH), 2.81 (t, J=8 Hz, 2H, $CH_2$), 2.74 (m, 1H, CH), 2.61 (m, 2H, $CH_2$), 2.00 (s, 3H, $CH_3$), 1.65 (m, 4H, $2CH_2$), 1.62 (s, 4H, $2CH_2$), 1.30–1.32 (m, 15H, $OCH_2CH_3$+$4CH_3$).

(2Z,4E)-3-Methyl-6-[1,2,3,4,7,8,9,10-octahydro-1,1,4,4-tetramethyl-6H-naphthocycloheptan-10-yl]hexa-2,4-dienoic acid. (structure 22, where $R_1$, $R_2$, $R_3$, $R_4$ and $R_{19}$ are methyl; $R_5$, $R_6$, $R_7$, $R_8$, $R_9$, and $R_{10}$, are hydrogen; $R_{15}$ is hydroxy; X, Y and Z are carbon; m=1 and n=2)

The title compound was prepared from compound 127a by the hydrolysis method described in Example 2. Compound 127b had $R_f$=0.3 (15% EtOAc-hexanes); $^1$H-NMR (400 MHz, $CDCl_3$) δ 7.66 (d, J=16 Hz, 1H, olefinic), 6.99 (s, 2H, ArH), 6.25 (m, 1H, olefinic), 5.50 (s, 1H, olefinic), 2.91 (m, 2H, $CH_2$), 2.80 (m, 2H, $CH_2$), 2.70 (m, 1H, CH), 2.55 (m, 2H, $CH_2$), 2.00 (s, 3H, $CH_3$), 1.63 (m, 4H, $2CH_2$), 1.60 (s, 4H, $CH_2$), 1.20–1.22 (m, 12H, $CH_3$).

EXAMPLE 44

Preparation of Compound 128b According to Schemes I and VI (2E,4E)-3-Methyl-6-[5,6,7,8-tetrahydro-5,5,8,8-tetramethylnaphthyl-(2,3-b)-2,2- dimethyl-pyran-4-yl]hexa-2,4-dienoic acid (structure 22, where $R_1$, $R_2$, $R_3$, $R_4$, $R_7$, $R_8$, and $R_{19}$ are methyl; $R_5$, $R_6$, $R_9$, $R_{10}$ are hydrogen; $R_{15}$ is hydroxy; X and Y are carbon; Z is oxygen; m=n=1).

[(E)-3,4,5,6,7,8-Hexahydro-2,2,5,5,8,8-hexamethylnaphtho(2,3-b)-1,2-pyran-4-ylidene]ethanitrile (400 mg, 1.30 mmol, from Example 8) was converted to the corresponding aldehyde by means of the procedure described in Example 1. Flash chromatography (10% EtOAc/hexane) gave [(E)-3,4,5,6,7,8-hexahydro-2,2,5,5,8, 8-hexamethylnaphtho(2,3-b)-1,2-pyran-4-ylidene] acetaldehyde as a light yellow solid (220 mg, 0.70 mmol, 54%): $^1$H NMR (400 MHz, $CDCl_3$) δ 10.1 (d, 1H), 7.53 (s, 1H), 6.8 (s, 1H), 6.60 (d, 1H), 3.05 (s, 2H), 1.65 (s, 4H), 1.40 (s, 6H), 1.27 (s, 6H), 1.25 (s, 6H).

The above aldehyde (220 mg, 0.70 mmol) was hydrogenated using a procedure similar to that described in Example 41. TLC (20% EtOAc/hexane, cerium molybdate) indicated two products. Filtration and concentration gave a light yellow oil (140 mg), which was purified by flash chromatography (20% EtOAc/hexane) to give [3,4,5,6,7,8-hexahydro-2,2,5,5,8,8-hexamethylnaphtho(2,3-b)-1,2-pyran-4-yl]acetaldehyde as a clear oil which solidified on standing (39 mg, 0.12 mmol, 18% yield): $R_f$=0.43 (20% EtOAc/hexane); $^1$H NMR (400 MHz, $CDCl_3$) δ 9.9 (t, 1H), 7.00 (s, 1H), 6.7 (s, 1H), 3.45 (m, 1H), 3.05 (dd, 1H), 2.70 (dd, 1H), 2.00 (dd, 1H), 1.65 (s, 4H), 1.60 (dd, 1H), 1.31 (s, 6H), 1.26 (s, 6H), 1.24 (s, 6).

Using the procedure described in Example 1, the above saturated aldehyde (39 mg, 0.124 mmol) was coupled with diethyl 3-ethoxycarbonyl-2-methylprop-2-enylphosphonate. A total of 1.5 equivalents of phosphonate and sodium hydride were used in place of the original conditions. Aqueous work up, followed by flash chromatography (20% EtOAc/hexane) afforded a mixture of ethyl (2E,4E)- and (2Z,4E)-3-methyl-6-[5,6,7,8-tetrahydro-5,5,8,8-tetramethylnaphthyl-(2,3-b)-2,2-dimethylpyran-4-yl]hexa-2,4-dienoate as a clear oil (38 mg, 0.089 mmol, 73% yield.). $^1$H NMR indicated a 2:1 ratio of isomers favoring the trans product. These could not be separated by chromatography and were used as a crude mixture in the subsequent reaction: $^1$H NMR (400 MHz, $CDCl_3$) δ 7.79 (d, 1H), 7.15 (s, 2H), 6.7 (s, 2H), 6.20 (m, 1H), 6.15 (m, 2H,), 5.7 (d, 1H), 5.6 (d, 1H), 4.10 (m, 4H), 2.95 (m, 2H), 2.90 (m, 2H), 2.50 (m, 1H), 2.40 (m, 1H), 2.10 (s, 3H), 2.00 (s, 3H), 1.82 (m, 2H), 1.62 (s, 8H), 1.60 (dd, 2H), 1.31 (t, 6H), 1.29 (s, 12H ), 1.26 (s, 12H), 1.24 (s, 12H).

The above mixture of esters (38 mg, 0.089 mmol) was hydrolyzed according to the standard procedure described in Example 2. A mixture of (2E,4E)- and (2Z,4E)-3-methyl-6-[5,6,7,8-tetrahydro-5,5,8,8-tetramethylnaphthyl (2,3-b )2,2-dimethylpyran-4-yl]hexa-2,4-dienoic acid was isolated as a light yellow solid (34 mg, 0.86 mmol, 96%): $^1$H NMR indicated a 2:1 ratio of isomers favoring the trans product. A 5 mg sample of the crude material was purified by HPLC (MeOH /10 mM ammonium acetate) to give the title acid (128a) as an oily yellow solid (2.4 mg): $^1$H NMR (400 MHz, $CDCl_3$) δ 7.15 (s, 1H), 6.7 (s, 1H), 6.22 (m, 2H), 5.75 (s, 1H), 2.90 (m, 2H), 2.40 (m, 1H), 2.30 (s, 3H), 1.82 (m, 1H ), 1.65 (s, 4H), 1.60 (dd, 1H), 1.29 (s, 6H), 1.26 (s, 6H), 1.24 (s, 6H).

EXAMPLE 45

Preparation of Compound 129b According to Schemes I and II (2Z,4E)-3-Methyl-6-[5,6,7,8-tetrahydro-5,5,8,8-tetramethylnaphthyl-(2,3-b)-2,2-dimethylpyran-4-yl]hexa-2,4-dienoic acid (structure 22, where $R_1$, $R_2$, $R_3$, $R_4$, $R_7$, $R_8$, and $R_{19}$ are methyl; $R_5$, $R_6$, $R_9$, $R_{10}$ are hydrogen; $R_{15}$ is hydroxy; X and Y are carbon; Z is oxygen; m=n=1).

A mixture of (2E,4E)- and (2Z,4E)-3-methyl-6-[5,6,7,8-tetrahydro-5,5,8,8-tetramethyl naphthyl(2,3-b)-2,2-dimethylpyran-4-yl]hexa-2,4-dienoic acid from Example 44 was purified by HPLC (MeOH /10 mM ammonium acetate) to give the title acid as an oily yellow solid (2.2 mg): $^1$H NMR (400 MHz, CDCl$_3$) δ 7.65 (d, 1H), 7.15 (s, 1H), 6.7 (s, 1H), 6.20 (m, 1H), 5.68(s, 1H), 2.95 (m, 2H), 2.50 (m, 1H), 2.00 (s, 3H), 1.82 (m, 1H), 1.62 (s, 4H), 1.60 (dd, 1H), 1.29 (s, 6H ), 1.26 (s, 6H), 1.24 (s, 6H).

EXAMPLE 46

Preparation of Compound 130b According to Schemes IV and VI (2E,4E)-3-Methyl-6-[5,6,7,8-tetrahydro-5,5,8,8-tetramethylnaphthyl-(2,3-b)-pyran-4-yl]-hexa-2,4-dienoic acid (structure 22, where $R_1$, $R_2$, $R_3$, $R_4$, and $R_{19}$ are methyl; $R_5$, $R_6$, $R_{7, R8}$, $R_9$, $R_{10}$ are hydrogen; $R_{15}$ is hydroxy; X and Y are carbon; Z is oxygen; m=n=1).

To a stirred solution of diethyl cyanomethylphosphonate (13.1 g, 74.3 mmol) in THF (50 ml) at −20° C. under nitrogen was added dropwise, n-BuLi (29.5ml of a 2.5M solution in hexanes). The resulting white viscous mixture was stirred for 1.5 h and treated with 4-chromanone (10.0 g, 67.6 mmol, Aldrich) in THF (30 ml). The turbid, orange solution was stirred in an ice water bath, then allowed to warm to room temperature over 45 min. TLC of the reaction mixture (20% EtOAc/hexanes, cerium molybdate) indicated the formation of two product spots, $R_f$=0.23 and 0.36 respectively. The reaction mixture was quenched by dropwise addition of saturated ammonium chloride. Aqueous workup (and EtOAc extract), followed by filtration through a silica gel plug to remove excess phosphonate gave an isomeric mixture of 4-cyanomethylidenebenzopyrans (4:1 favoring the trans product) as a yellow oil (10.1 g, 59.1 mmol, 87%): $^1$H NMR (400 MHz, CDCl$_3$) δ 8.35 (dd, 1H), 7.5 (d, 2H), 7.32 (m, 2H ), 7.0 (m, 1H), 6.9 (m, 2H), 5.73 (s, 1H), 5.17 (s, 1H ), 4.3 (m, 4H), 3.0 (dd, 2H ), 2.75 (dd, 2H).

To a solution of the above nitriles (3.06 g, 17.9 mmol) in EtOAc (25 ml) was added 10% palladium on carbon (600 mg). This heterogeneous mixture was placed under an atmosphere of hydrogen and stirred at 25° C. for 16 h. The reaction mixture was filtered and the solvent removed to give 4-cyanomethylbenzopyran as a rose colored oil (2.97 g, 17.2 mmol, 96%): $_1$H NMR (400 MHz, CDCl$_3$) δ 7.16 (m, 2H), 6.9 (dd, 1H), 6.83 (d, 1H), 4.2 (m, 2H), 3.25 (m, 1H), 2.82 (dd, 1H), 2.6 (dd, 1H), 2.3 (m, 1H), 2.15 (m, 1H).

To a solution of the above nitrile (2.9 g, 16.8 mmol), 2,5-dichloro-2,5-dimethylhexane (3.1 g, 16.8 mmol) in 1,2-dichloroethane (25 ml) at 25° C. was added aluminum trichloride (3.1 g, 16.8 mmol) in portions. The exothermic reaction was stirred for 2 h, and the orange mixture was poured over ice. Aqueous work up (EtOAc extraction), followed by recrystallization (MeOH /water) gave [5,6,7,8-tetrahydro-5,5,8,8-tetramethylnaphthyl-(2,3-b)pyran-4-yl] cyanomethane, as white needles (3.0 g, 10.6 mmol, 63%): $_1$H NMR (400 MHz, CDC$_3$) δ 7.05 (s, 1H,), 6.77 (s, 1H ), 4.15 (m, 2H), 3.22 (m, 1H), 2.6 (dd, 1H), 2.3 (dd, 1H), 2.25 (m, 1H), 1.95 (m, 1H ), 1.65 (s, 4 H), 1.25 (s, 12H).

To a solution of the above tricyclic nitrile (1.3 g, 4.6 mmol) in THF (25 ml) at −78° C. under nitrogen was added dropwise, DIBAL (3 ml of 1.0M solution in CH$_2$Cl$_2$). The mixture was stirred for 30 min, warmed to 25° C., and stirred for 16 h. The reaction mixture was quenched by addition of saturated ammonium chloride, followed with 1N HCl and sodium potassium tartrate. Extractive work-up (EtOAc) gave [5,6,7,8-tetrahydro-5,5,8,8-tetramethylnaphthyl (2,3-b)- pyran-4-yl]acetaldehyde as a light yellow solid (1.2 g, 4.2 mmol, 91.5%): $^1$H NMR (400 MHz, CDCl$_3$) δ 9.90 (t, 1H), 7.00 (s, 1H), 6.75 (s, 1H), 4.15 (m, 2H), 3.45 (m, 1H), 2.93 (dd, 1H), 2.73 (dd, 1H), 2.20 (m, 1H), 1.80 (m, 1H), 1.62 (s, 4H), 1.26 (s, 6H), 1.24 (s, 6H).

To a solution of diethyl 3-ethoxycarbonyl-2-methylprop-2-enylphosphonate (475 mg, 1.80 mM) in THF (10ml ) at −78° C. under nitrogen was added n-BuLi (0.75 ml of a 2.5M solution in hexanes). The mixture was warmed to −20° C. over 40 min, and the above aldehyde (467 mg, 1.63 mmol) in THF (2 ml) was added in one portion. The reaction mixture was stirred at 0° C. for 1 h, then quenched with saturated ammonium chloride. Extractive work-up (EtOAc) gave ethyl (2E,4E)- and (2Z,4E)-3-methyl-6-[5,6,7,8-tetrahydro-5,5,8,8-tetramethylnaphthyl (2,3-b) pyran-4-yl] hexa-2,4-dienoate as a yellow oil. Flash chromatography (20% EtOAc/hexane) gave the mixture of esters as a pale yellow oil (400 mg, 1.01 mmol, 62.9%): $^1$H NMR indicated the isomers in a 3:1 ratio favoring the trans product. These could not be resolved by chromatography and were used as a mixture in subsequent reactions: $^1$H NMR (400 MHz, CDCl$_3$) δ 7.6 (d, 1H), 7.05(s, 2H), 6.72(s, 1H), 6.25(m, 3H), 5.75(s, 1H ), 5.65 (s, 1H), 4.15(m, 8H), 2.90(m, 2H), 2.71(m, 2H), 2.42 (m, 2H ), 2.30 (s, 3H), 2.05 (m, 2H), 2.03 (s, 3H), 1.8 (m, 2H), 1.62 (s, 8H), 1.30 (t, 6H), 1.28 (s, 12H), 1.25 (s, 12H).

The mixture of esters (400 mg, 1.01 mmol) in ethanol (5 ml) was treated with sodium hydroxide (500 mg, 12.5 mmol) in a 60% ethanol/water solution (5 ml) and refluxed for 3 h. The reaction mixture was cooled to 25° C., diluted with water, acidified with 1N HCl and extracted (EtOAc) to give a mixture of (2E,4E) and (2Z,4E)-3-methyl-6-[5,6,7,8-tetrahydro-5,5,8,8-tetramethylnaphthyl(2,3-b )pyran-4-yl]hexa-2,4-dienoic acid as a light yellow solid (284 mg, 78 mmol, 78%). Recrystallization (MeOH/water) afforded 130b as an off-white solid (74 mg): TLC $R_f$=0.24 (20% EtOAc/Hexane); mp 195.6° C.; $^1$H NMR (400 MHz, CDCl$_3$) δ 7.05 (s, 1H), 6.72 (s, 1H), 6.25 (m, 2H), 5.75 (d, 1H), 4.15 (dd, 2H), 2.90 (m, 1H), 2.71 (m, 1H ), 2.42 (m, 1H), 2.30 (s, 3H), 2.05 (m, 1H), 1.8 (m, 1H), 1.62 (s, 4 H), 1.26 (s, 6H), 1.24 (s, 6H).

EXAMPLE 47

Preparation of Compound 131b According to Schemes IV and VI (2Z,4E)-3-Methyl-6-[5,6,7,8-tetrahydro-5,5,8,8-tetramethyl naphthyl (2,3-b ) pyran-4-yl]-hexa-2,4-dienoic acid (structure 22, where $R_1$, $R_2$, $R_3$, $R_4$, and $R_{19}$ are methyl; $R_5$, $R_6$, $R_7$, $R_8$, $R_9$, $R_{10}$ are hydrogen; $R_{15}$ is hydroxy; X and Y are carbon; Z is oxygen; n=m=1).

Concentration of the second crop mother liquors from Example 46 gave a yellow oil. $^1$H NMR confirmed the structure as the corresponding (2Z,4E) acid. GC analysis of this material indicated 89% geometric purity with the remainder being the (2E,4E) isomer: Compound 131b had TLC $R_f$=0.23 (20% EtOAc/Hexane); $^1$H NMR (400 MHz, CDCl$_3$) δ 7.60 (d, 1H ), 7.05 (s, 1H), 6.72 (s, 1H ), 6.25 (m, 1H), 5.65 (m, 1H), 4.18 (dd, 2H), 2.95 (m, 1H ), 2.71 (m, 1H), 2.50 (m, 1H), 2.05 (m, 1H), 2.03 (s, 3H), 1.8 (m, 1H), 1.62 (s, 4 H), 1.26 (s, 6H), 1.24 (s, 6H).

EXAMPLE 48

Preparation of Compounds 132b and 133b According to Scheme VII (+)-(2E,4E)-3-Methyl-6-(1,2,3,4,5,6,7,8-octahydro-5,5,8,8-tetramethylanthracen-1-yl)hexa-2,4-dienoic acid (structure 28, where $R_1$, $R_2$, $R_3$, $R_4$ and $R_{19}$ are methyl; $R_5$, $R_7$, $R_8$, $R_9$ and $R_{10}$ are hydrogen; $R_{15}$ is hydroxy; X, Y and Z are carbon and m=n=1). The assigned absolute stereochemistry is arbitrary.

Ester 18 (where $R_1$, $R_2$, $R_3$, and $R_4$ are methyl; $R_5$, $R_7$, $R_8$, $R_9$, and $R_{10}$ are hydrogen; X, Y and Z are carbon) (prepared in Example 34) (740 mg, 2.49 mmol) was dissolved in EtOAc (5.0 mL) and Pd/C 10% (20 mg) was added. The mixture was stirred under an atmosphere of hydrogen for 12 h. The mixture was filtered through a pad of celite and thoroughly rinsed with excess EtOAc. The solvent was evaporated to give 730 mg (98% yield) of the ester: methyl (R,S)-2-(1,2,3,4,5,6,7,8-octahydro-5,5,8,8-tetramethylanthracen-1-yl)acetate: $^1$H NMR (400 MHz, CDCl$_3$) δ 7.07 (s, 1H, Ar), 6.99 (s, 1H, Ar), 3.72 (s, 3H, OCH$_3$), 3.30 (m, 1H), 2.72 (m, 3H), 2.53 (dd, J=9.9, 8.2 Hz, 1H), 1.89 (m, 1H), 1.79 (m, 2H), 1.75 (m, 1H), 1.75 (s, 4H), 1.24 (s, 12H).

The above ester (730 mg, 2.44 mmol) was dissolved in THF (5.0 mL) and LiOH (2.0 mL of a 2.0M aqueous solution) was added. The mixture was stirred at room temperature for 40 h, then acidified using 1 N HCL and extracted with EtOAc. The organic layer was dried over MgSO$_4$, filtered, and evaporated to give the corresponding acid as a white solid, 648 mg (88% yield). The crude acid (648 mg, 2.16 mmol) was dissolved in dichloromethane (5.0 mL) and a drop of dimethylformamide was added. Oxalyl chloride (0.380 mL, 4.32 mM) was added dropwise, followed by stirring at room temperature until the evolution of CO$_2$ ceased (~2 h). The solvent was evaporated and the residue dried under high vacuum (~0.1 mmHg) to give the corresponding acid chloride (689 mg), (R,S)-2-(1,2,3,4,5,6,7,8-octahydro-5,5,8,8-tetramethylanthracen-1-yl)-acetyl chloride.

A 50 mL round-bottom flask was flame-dried and charged with (S)-4-benzyl-2-oxazolidinone (576 mg, 3.25 mmol) and anhydrous THF (10 mL). The solution was cooled to −78° C. and n-BuLi (2.1 mL, 1.55M in hexanes) was added. The solution was stirred at −78° C. for 30 min and a solution of the above acid chloride in THF (10 mL) was added slowly. Stirring was continued for 30 min, and the mixture was warmed to room temperature. After 5 min, the reaction mixture was cooled to −78° C., quenched with a saturated solution of ammonium chloride, and extracted with EtOAc (2×20 mL). The organic layer was washed with water (2×10 mL), brine (2×10 ml) and dried over MgSO$_4$. Evaporation of the solvent gave a diastereomeric mixture of the corresponding amides (70% yield), which were chromatographically separated (hexanes:EtOAc=95:5). The less polar amide had $^1$H NMR (400 MHz, CDCl$_3$) δ 7.36–7.22 (m, 5H, Ar), 7.18 (s, 1H, Ar), 6.99 (s, 1H, Ar), 4.71 (m, 1H), 4.18 (m, 2H), 3.42 (m, 1H), 3.35 (dd, J=14.9, 3.9 Hz, 1H), 3.29 (s, 1H), 3.27 (s, 1H), 2.80 (d, J=12 Hz, 1H), 2.80 (d, J=12 Hz, 1H), 2.75 (m, 2H), 1.90 (m, 2H), 1.76 (m, 2H), 1.65 (s, 4H), 1.26 (s, 6H), 1.24 (s, 6H); the more polar amide had $^1$H NMR (400 MHz, CDCl$_3$) δ 7.36–7.22 (m, 5H, Ar), 7.00 (s, 1H, Ar), 4.73 (m, 1H), 4.20 (m, 2H), 3.50 (m, 1H), 3.34 (m, 2H), 3.20 (m, 1H), 2.75 (m, 3H), 1.90 (m, 2H), 1.75 (m, 2H), 1.66 (s, 4H), 1.28 (s, 6H), 1.27 (s, 6H).

A solution of the above more polar amide (190 mg, 4.13 mmol) in THF (10.0 mL) was cooled to −78° C. LiAlH4 (0.425 mL of 1.0M solution in THF) was added at −78° C., stirred for 30 min, then warmed to 0° C. The mixture was quenched with water (0.1 mL), NaOH (15%, 0.1 mL), and water (0.3 mL), then extracted with EtOAc (30 mL). The organic layer was dried over MgSO$_4$, and the solvent evaporated. The crude residue was purified by silica gel chromatography (hexanes:EtOAc=4:1) to give 61 mg of the desired alcohol, (+)-2-(1,2,3,4,5,6,7,8-octahydro-5,5,8,8-tetramethylanthracen-1-yl)ethan-1-ol (55% yield), [a]D+12.7 (c 0.59, CHCl$_3$).

The above alcohol (60 mg, 0.21 mmol) was dissolved in dichloromethane (5.0 mL) and Dess-Martin reagent (2×135 mg, 0.63 mmol) was added in two portions and stirred for 60 min. A saturated solution of sodium bicarbonate (3.0 mL) was added, followed by solid sodium thiosulfate. The mixture was stirred vigorously and extracted with dichloromethane. The organic layer was washed with water (2×5 mL), brine (2×5 mL) and dried over MgSO$_4$. The solvent was evaporated and the residue was purified over a short silica gel chromatography column to give 48 mg of the desired aldehyde, (+)-2-(1,2,3,4,5,6,7,8-octahydro-5,5,8,8-tetramethylanthracen-1-yl)ethan-1-al (81% yield).

The above aldehyde was transformed to the title compound using a procedure similar to that described for the racemic material (Examples 37 and 38). Compound 132b had [a]D+16.2 (c 0.36, CHCl$_3$). The $^1$HNMR spectrum was indistinguishable from that of the racemate 124b.

(−)-(2E,4E)-3-Methyl-6-(1,2,3,4,5,6,7,8-octahydro-5,5,8,8-tetramethylanthracen-1-yl)hexa-2,4-dienoic acid (133b) (structure 29, where $R_1$, $R_2$, $R_3$, $R_4$ and $R_{19}$ are methyl; $R_5$, $R_7$, $R_8$, $R_9$ and $R_{10}$ are hydrogen; $R_{15}$ is hydroxy; X, Y, and Z are carbon; and m=n=1).

The title compound was prepared from the diastereomeric, less polar amide described above using the procedure for compound 132b. Compound 133b had $[\alpha]_D$-16.4 (c 0.33, CHCl$_3$). $^1$HNMR data is indistinguishable from racemic 124b.

EXAMPLE 49

Preparation of Compound 134a According to Scheme VIII

Methyl (2E)-3-methyl-6-(1,2,3,4,6,7,8,9-octahydro-6,6,9,9-tetramethylanthracen-1-yl)hex-2-enoate (structure 32, where $R_1$, $R_2$, $R_3$, $R_4$ and $R_{19}$ are methyl; $R_5$, $R_6$, $R_7$, $R_8$, $R_9$, and $R_{10}$ are hydrogen; $R_{15}$ is methoxy; X, Y, and Z are carbon; m=n=1) (1,2,3,4,6,7,8,9-octahydro-6,6,9,9-tetramethylanthracen-1-yl)acetaldehyde, an intermediate for the preparation of compound 124a of Example 37, was condensed with the sodium anion of diethyl (2-oxopropyl) phosphonate to give (3E)-1-(1,2,3,4,6,7,8,9-octahydro-6,6,9,9-tetramethylanthracen-1-yl)pent-2-en-4-one: $^1$H NMR (400 MHz, CDCl$_3$) δ 7.07 (s, 1H, ArH), 7.00 (s, 1H, ArH), 6.89 (m, 1H, olefinic), 6.12 (d, J=15.9 Hz, 1H, olefinic), 2.94 (m, 1H, benzylic), 2.72 (br t, 2H, CH$_2$, benzylic), 2.68–2.47 (m, 2H, CH$_2$, allylic), 2.26 (s, 3H, CH$_3$), 1.82–1.62 (m, 4H, 2CH$_2$), 1.66 (s, 4H, 2CH$_2$), 1.26 (s, 6H, 2CH$_3$) 1.24 (s, 6H, 2CH$_3$).

The above enone was subjected to hydrogenation using 10% Pd on C as a catalyst, followed by condensation with trimethyl phosphonoacetate using NaH as a base to give methyl (2E)-3-methyl-6-(1,2,3,4,6,7,8,9-octahydro-6,6,9,9-tetramethylanthracen-1-yl)hex-2-enoate: $R_f$=0.25 (hexane); $^1$H NMR (400 MHz, CDCl$_3$) δ 7.05 (s, 1H, ArH), 6.97 (s, 1H, ArH), 5.69 (s, 1H, olefinic), 3.68 (s, 3H, OCH$_3$), 2.69 (m, 3H, benzylic), 2.17 (s, 3H, CH$_3$), 2.16 (m, 2H, allylic), 1.81 (m, 2H, CH$_2$), 1.68 (s, 4H, 2CH$_2$), 1.68–1.54 (m, 6H, 3CH$_2$), 1.26 (s, 6H, 2Ch$_3$), 1.24 (s, 6H, 2CH$_3$).

EXAMPLE 50

Preparation of Compound 134b According to Scheme VIII (2E)-3-methyl-6-(1,2,3,4,6,7,8,9-octahydro-6,6,9,9-tetramethylanthracen-1-yl)-hex-2-enoic acid (structure 32, where $R_1$, $R_2$, $R_3$, $R_4$ and $R_{19}$ are methyl; $R_5$, $R_6$, $R_7$, $R_8$, $R_9$, and $R_{10}$ are hydrogen; $R_{15S}$ is hydroxy; X, Y, and Z are carbon; m=n=1)

The title compound was prepared by hydrolysis of compound 134a using the standard hydrolysis conditions described in Example 2. Compound 134a had $R_f$=0.31 (50% ether in hexane); mp 190–192° C.; $^1$H NMR (400 MHz, CDCl$_3$) δ 7.05 (s, 1H, ArH), 6.98 (s, 1H, ArH), 5.72 (s, 1H, olefinic), 2.71 (m, 3H, benzylic), 2.20 (m, 2H, allylic), 2.18 (s, 3H, CH$_3$), 1.82 (m, 2H, CH$_2$), 1.75–1.59 (m, 6H, 3CH$_2$), 1.66 (s, 4H, 2CH$_2$), 1.26 (s, 6H, 2CH$_3$), 1.25 (s, 6H, 2CH$_3$).

EXAMPLE 51

Preparation of Compound 135a According to Scheme IX

Ethyl (2E,4E)-3-methyl-6-[(E)-2,3,6,7,8,9-hexahydro-6,6,9,9-tetramethyl-1H-cyclopenta[a]naphthalen-3-ylidene]hexa-2,4-dienoate (structure 35, where $R_1$, $R_2$, $R_3$, $R_4$, and $R_{19}$ are methyl; $R_9$ and $R_{10}$ are hydrogen; $R_{15}$ is ethoxy; X and Y are carbon; m=1, and n=0).

The title compound was prepared from 2,3,6,7,8,9-hexahydro-6,6,9,9-tetramethyl-1H-cyclopenta[a]naphthalen-3-one [a by-product isolated from the preparation of 2,3,5,6,7,8-hexahydro-5,5,8,8-tetramethyl-cyclopenta[b]naphthalen-1-one in Example 3] in a manner similar to that described for compound 51a using the procedure described in Example 1. Compound 135a had $^1$H NMR (400 MHz, CDCl$_3$) δ 7.36 (d, J=8.27 Hz, 1H, ArH), 7.26 (d, J=8.27 Hz, 1H, ArH), 6.90 (dd, J=11.2, 15.1 Hz, 1H, olefinic), 6.59 (d, J=11.2 Hz, 1H, olefinic), 6.31 (d, J=15.1 Hz, 1H, olefinic), 5.78 (s, CH, olefinic), 4.18 (q, J=7.02 Hz, 2H, OCH$_2$), 3.23 (br m, 2H, benzylic), 2.92 (br m, 2H, allylic), 2.37 (s, 3H, CH$_3$), 1.69 (br s, 4H, 2CH$_2$), 1.36 (s, 6H, 2CH$_3$), 1.32 (s, 6H, 2CH$_3$), 1.31 (t, J=7.0 Hz, 3H, CH$_3$).

EXAMPLE 52

Preparation of Compound 135b According to Scheme VIII (2E,4E)-3-Methyl-6-[(E)-2,3,6,7,8,9-hexahydro-6,6,9,9-tetramethyl-1H-cyclopenta[a]naphthalen-3-ylidene]hexa-2,4-dienoic acid (structure 35, where $R_1$, $R_2$, $R_3$, $R_4$, and $R_{19}$ are methyl; $R_9$ and $R_{10}$ are hydrogen; $R_{15}$ is hydroxy; X and Y are carbon; m=1, and n=0).

The title compound was prepared from compound 135a using the standard hydrolysis condition described in Example 2. Acid 135b had mp 195–197° C.; $^1$H NMR (400 MHz, CDCl$_3$) δ 7.30 (d, J=8.2 Hz, 1H, ArH), 7.21 (d, J=8.2 Hz, 1H, ArH), 6.88 (dd, J=11.3, 15.1 Hz, 1H, olefinic), 6.54 (d, J=11.3 Hz, 1H, olefinic), 6.27 (d, J=15.1 Hz, 1H, olefinic), 5.74 (s, 1H, olefinic), 3.17 (br m, 2H, CH$_2$, benzylic), 2.86 (m, 2H, CH$_2$, allylic), 2.32 (s, 3H, CH$_3$), 1.62 (br s, 4H, 2CH$_2$), 1.28 (s, 6H, 2CH$_3$), 1.24 (s, 6H, 2CH$_3$).

EXAMPLE 53

Preparation of Compound 136a According to Scheme IX

Ethyl (2E,4E)-3-methyl-6-(2,3,6,7,8,9-hexahydro-6,6,9,9-tetramethyl-1H-cyclopentafa]naphthalen-3-yl]hexa-2,4-dienoate (structure 36, where $R_1$, $R_2$, $R_3$, $R_4$, and $R_{19}$ are methyl; $R_9$ and $R_{10}$ are hydrogen; $R_{15}$ is ethoxy; X and Y are carbon; m=1, and n=0).

The title compound was prepared from (2,3,6,7,8,9-hexahydro-6,6,9,9-tetramethyl-1H-cyclopenta[a]naphthalen-3-ylidene)ethanitrile, which was prepared from the condensation of 2,3,6,7,8,9-hexahydro-6,6,9,9-tetramethyl-1H-cyclopenta[a]naphthalen-3-one (Example 51) with cyanomethylphosphonate using NaH as a base in a manner similar to that described for compound 124a as detailed in Example 37. Compound 136a had $^1$H NMR(400 MHz, CDCl$_3$) δ 7.20 (d, J=8.0 Hz, 1H, ArH), 7.03 (d, J=8.0 Hz, 1H, ArH), 6.18 (m, 2H, 2×olefinic), 5.71 (s, 1H, olefinic), 4.17 (q, J=7.6 Hz, 2H, OCH$_2$), 3.09 (m, 2H, CH$_2$, benzylic), 2.97 (m, 1H, benzylic), 2.67 (m, 1H, allylic), 2.86 (s, 3H, CH$_3$), 2.19 (m, 1H, allylic), 1.66 (m, 6H, 3CH$_2$), 1.34 (s, 6H, 2CH$_3$), 1.33 (s, 6H, 2CH$_3$), 1.24 (t, J=7.0 Hz, 3H, CH$_3$).

EXAMPLE 54

Preparation of Compound 136b According to Scheme IX (2E,4E)-3-Methyl-6-(2,3,6,7,8,9-hexahydro-6,6,9,9-tetramethyl-1H-cyclopenta[a]naphthalen-3-yl)hexa-2,4-dienoic acid (structure 36, where $R_1$, $R_2$, $R_3$, $R_4$, and $R_{19}$ are methyl; $R_9$ and $R_{10}$ are hydrogen; $R_{15}$ is hydroxy; X and Y are carbon; m=1, and n=0)

The title compound was prepared by hydrolysis of compound 136a using the standard hydrolysis conditions described in Example 2. Compound 136b had mp 208–210° C.; $^1$H NMR (400 MHz, CDCl$_3$) δ 7.22 (d, J=8.0 Hz, 1H, ArH), 7.03 (d, J=8.0 Hz, 1H, ArH), 6.22 (m, 2H, 2×olefinic), 5.75 (s, 1H, olefinic), 3.10 (m, 2H, benzylic), 2.95 (m, 1H, benzylic), 2.70 (m, 1H, allylic), 2.30 (s, 3H, CH$_3$), 2.20 (m, 1H, allylic), 1.66 (m, 6H, 3CH$_2$), 1.32 (s, 6H, 2CH$_3$), 1.28 (s, 6H, 2CH$_3$).

EXAMPLE 55

Preparation of Compound 137a According to Scheme IX

Ethyl (2E,4E)-3-methyl-6-[(Z)-1,2,3,4,7,8,9-heptahydro-7,7,9,9-tetramethyl-cyclopenta[f]naphthalen-4-ylidene]hexa-2,4-dienoate (structure 35, where $R_1$, $R_2$, $R_3$, $R_4$, and $R_{19}$ are methyl; $R_9$ and $R_{10}$ are hydrogen; $R_{15}$ is ethoxy; X and Y are carbon; m=0, and n=1)

The title compound was prepared from 1,2,3,4,7,8,9-heptahydro-7,7,9,9-tetramethyl-cyclopenta[f]naphthalen-4-one (isolated as a by-product for the preparation of 1,2,3,6,7,8-hexahydro-1,1,3,3-tetramethyl-cyclopenta[b]naphthalen-5-one in Example 5) using the procedure described in example 51. Compound 137a had $R_f$=0.50 (15% ether in hexane); $^1$H NMR (400 MHz, CDCl$_3$) δ:7.25 (d, J=7.9 Hz, 1H, ArH), 7.15 (dd, J=15.2, 11.4 Hz, 1H, olefinic), 7.00 (d, J=7.9 Hz, 1H, ArH), 6.30 (d, J=15.2 Hz, 1H, olefinic), 6.14 (d, J=11.4 Hz, 1H, olefinic), 5.76 (s, 1H, olefinic), 4.16 (q, 2H, OCH$_2$), 2.88 (t, J=6.4 Hz, 2H, benzylic), 2.51 (t, J=6.5 Hz, 2H, allylic), 2.29 (s, 3H, CH$_3$), 1.91 (m, 4H, 2CH$_2$), 1.42 (s, 6H, 2CH$_3$), 1.29 (m, 9H, 3CH$_3$).

EXAMPLE 56

Preparation of Compound 137b According to Scheme IX (2E,4E)-3-Methyl-6-[(Z)-1,2,3,4,7,8,9-heptahydro-7,7,9,9-tetramethyl-cyclopenta[f]naphthalen-4-ylidene]hexa-2,4-dienoic acid (structure 35, where $R_1$, $R_2$, $R_3$, $R_4$, and $R_{19}$ are methyl; $R_9$ and $R_{10}$ are hydrogen; $R_{15}$ is hydroxy; X and Y are carbon; m=0, and n=1)

The title compound was prepared from compound 137a using the standard hydrolysis conditions described in Example 2. Compound 137b had $R_f$=0.45 (50% ether in hexane), mp 176–178° C.; $^1$H NMR (400 MHz, CDCl$_3$) δ 7.24 (d, J=7.8 Hz, 1H, ArH), 7.19 (dd, J=15.2, 11.3 Hz, 1H, olefinic), 7.00 (d, J=7.9 Hz, 1H, ArH), 6.33 (d, J=15.2 Hz, 1H, olefinic), 6.16 (d, J=11.3 Hz, 1H, olefinic), 5.79 (s, 1H, olefinic), 2.88 (t, J=6.4 Hz, 2H, benzylic), 2.53 (t, J=6.4 Hz, 2H, allylic), 2.30 (s, 3H, CH$_3$), 1.93 (m, 4H, 2CH$_2$), 1.43 (s, 6H, 2CH$_3$), 1.31 (m, 6H, 2CH$_3$).

EXAMPLE 57

Preparation of Compound 138a According to Scheme X

Ethyl (2E,4E)-3-methyl-6-(7,7,10,10-tetramethyl-2,3,4,5,7,8,9,10-octahydronaphtho[2,3-6]-azepinyl)hexa-2,4-dienoate (structure 40, where $R_1$, $R_2$, $R_3$, $R_4$, and $R_{19}$ are methyl; $R_5$, $R_6$, $R_7$, $R_8$, $R_9$, and $R_{10}$ are hydrogen; $R_{15}$ is ethoxy; X, Y, and Z are carbon; m=n=1).

To a solution of 3,4,5,6,7,8-hexahydro-6,6,9,9-tetramethyl-2H-anthracen-1-one (256 mg, 1 mmol, from Example 1) in EtOH (10 ml) and pyridine (3 drops) was added H$_2$NOH-HCl (140 mg, 2 mmol) at 25° C., and resulting mixture was heated at reflux for 5 h. The mixture was cooled to room temperature and the filtered through filter paper and the solid was washed with hexane (50 ml). The solid was dried under vacuum to give pure trans-(3,4,6,7,8-hexahydro-6,6,9,9-tetramethyl-2H-anthracene-1-yl)-oxime (219 mg, 84%): $^1$H NMR(400 MHz, CDCl$_3$) δ 7.85 (s, 1H, ArH), 7.05 (s, 1H, ArH), 2.76 (t, J=6.1 Hz, 2H, benzylic), 2.69 (t, J=6.0 Hz, 2H, CH$_2$), 1.85 (m, 2H, CH$_2$), 1.65 (s, 4H, 2CH$_2$), 1.32 (s, 6H, 2CH$_3$) (s, 6H, 2CH$_3$).

The above oxime (271 mg, 1 mmol) in THF(10 ml) was treated with LiAlH$_4$ (3 ml, 1M, 3 mM) at room temperature, and the resulting mixture was heated at reflux (80° C.) for 8 h. The reaction mixture was cooled to 0° C., quenched with sodium potassium tartrate (20 ml), extracted with EtOAc (100 ml), dried over MgSO$_4$ and concentrated under reduced pressure. The crude product was chromatographed (20% ether in hexane) to afford pure 5,6,7,8-tetrahydro-5,5,8,8-tetramethyl-(2,3)-naphthyl-[blazepine (218 mg, 85%): $^1$H NMR(400 MHz, CDCl$_3$) δ 6.95 (s, 1H, ArH), 6.62 (s, 1H, ArH), 3.01 (t, J=6.2 Hz, 2H, benzylic), 2.69 (br m, 2H, CH$_2$), 1.73 (m, 2H, CH$_2$), 1.62 (m, 2H, CH$_2$), 1.61 (s, 4H, 2CH$_2$), 1.25 (s, 12H, 4CH$_3$).

To a solution of the above azepine (257 mg, 1 mmol) in THF (5 ml) was added NaH (80 mg, 60% in oil, 2 mmol) at 0° C., and the resulting mixture was stirred at 0° C. for 30 min. To this solution was added ethyl (2E,4E)-3-methyl-6-bromohexa-2,4-dienoate (233 mg, 1 mmol) [prepared by NaBH$_4$ reduction of ethyl (2E,4E)-(3-methyl-5-formyl)penta-2,4-dienoate in Example 14, followed by bromination using PBr$_3$ in ether at 0° C. to afford the necessary bromo compound] in THF (5 ml) at room temperature, and the resulting mixture was stirred for 8 h. Standard work-up procedure as described in Example 1, followed by chromatographic purification (10% ether in hexane) gave the title ester (294 mg, 72%): R$_f$=0.78(20% ether in hexane); $^1$H NMR(400 MHz, CDCl$_3$) δ 6.97 (s, 1H, ArH), 6.75 (s, 1H, ArH), 6.32 (d, J=15.8 Hz, 1H, olefinic), 6.22 (dt, J=15.8, 5.6 Hz, 1H, olefinic), 5.72 (s, 1H, olefinic), 4.15 (q, J=7.0 Hz, 2H, OCH$_2$), 3.85 (br d, J=5.6 Hz, 2H, allylic), 2.86 (br t, 2H, NCH$_2$), 2.73 (m, 2H, benzylic), 2.25 (s, 3H, CH$_3$), 1.66 (m, 4H, CH$_2$), 1.61 (s, 4H, 2CH$_2$), 1.58 (m, 2H, CH$_2$), 1.25 (t, J=7.0 Hz, 3H, CH$_3$), 1.21 (s, 6H, 2CH$_3$), 1.20 (s, 6H, 2CH$_3$).

EXAMPLE 58

Preparation of Compound 138b According to Scheme X (2E,4E)-3-Methyl-6-[7,7,10,10-tetramethyl-2,3,4,5,7,8,9,10-octahydronaphtho[2,3-6]azepinyl)hexa-2,4-dienoic acid (structure 42, where $R_1$, $R_2$, $R_3$, $R_4$, and $R_{19}$ are methyl; $R_5$, $R_6$, $R_7$, $R_8$, $R_9$, and $R_{10}$ are hydrogen; $R_{15}$ is hydroxy; X, Y, and Z are carbon; m=n=1).

The title compound was prepared from compound 138a using the standard hydrolysis conditions described in Example 2. Compound 138b as an amorphous solid had R$_f$=0.33 (50% ether in hexane); $^1$H NMR (400 MHz, CDCl$_3$) δ 6.99 (s, 1H, ArH), 6.75 (s, 1H, ArH), 6.36 (d, J=15.7 Hz, 1H, olefinic), 6.22 (dt, J=15.7, 5.6 Hz, 1H, olefinic), 5.78 (s, 1H, olefinic), 3.89 (d, J=5.6 Hz, 2H, allylic), 2.88 (br t, 2H, NCH$_2$), 2.73 (m, 2H, benzylic), 2.28 (s, 3H, CH$_3$), 1.69 (m, 2H, CH$_2$), 1.63 (s, 4H, 2CH$_2$), 1.59 (m, 2H, CH$_2$), 1.23 (s, 6H, 2CH$_3$), 1.22 (s, 6H, 2CH$_3$).

EXAMPLE 59

Preparation of Compound 139a According to Scheme X

Ethyl 3-methyl-6-(3,4,6,7,8,9-hexahydro-6,6,9,9-tetramethyl-2H-benzo[g]quinolin-1-yl)hexa-2,4-dienoate (structure 40, where $R_1$, $R_2$, $R_3$, $R_4$, and $R_{19}$ are methyl; $R_5$, $R_6$, $R_7$, $R_8$, $R_9$, $R_{10}$ are hydrogen; $R_{15}$ is ethoxy; X, Y, and Z are carbon; m=1, and n=0).

The title compound was prepared from 2,3,5,6,7,8-hexahydro-5,5,8,8-tetramethyl-cyclopenta[b]naphthalen-1-one [(U.S. Pat. No. 2,815,382 (1957)] in a manner similar to that described for compound 138a of Example 57. Ester 139a had $^1$H NMR(400 MHz, CDCl$_3$) δ 6.88 (s, 1H, ArH), 6.51 (s, 1H, ArH), 6.29 (d, J=15.7 Hz, 1H, olefinic), 6.15 (dt, J=15.7, 5.6 Hz, 1H, olefinic), 5.72 (s, 1H, olefinic), 4.16 (q, J=7.0 Hz, 2H, OCH$_2$), 4.00 (d, J=5.6 Hz, 2H, allylic), 3.23 (br t, 2H, NCH$_2$), 2.73(br t, 2H, benzylic), 2.25 (s, 3H, CH$_3$), 1.96 (m, 2H, CH$_2$), 1.63(s, 4H, 2CH$_2$), 1.26 (t, J=7.0 Hz, 3H, CH$_3$), 1.24 (s, 6H, 2CH$_3$), 1.23 (s, 6H, 2CH$_3$).

EXAMPLE 60

Preparation of Compound 139b According to Scheme X (2E,4E)-3-Methyl-6-[3,4,6,7,8,9-hexahydro-6,6,9,9-tetramethyl-2H-benzo[g]quinolin-1-yl)hexa-2,4-dienoic acid (structure 40, where $R_1$, $R_2$, $R_3$, $R_4$, and $R_{19}$ are methyl; $R_5$, $R_6$, $R_7$, $R_8$, $R_9$, and $R_{10}$ are hydrogen; $R_{15}$ is hydroxy; X, Y, and Z are carbon; m=1, and n=0).

The title compound was prepared from compound 139a using the standard hydrolysis conditions detailed in Example 2. Compound 139b had mp 211–213° C.; $^1$H NMR (400 MHz, CDCl$_3$) δ 6.88 (s, 1H, ArH), 6.44 (s, 1H, ArH), 6.33 (d, J=15.7 Hz, 1H, olefinic), 6.20 (dt, J=15.7, 5.6 Hz, 1H, olefinic), 5.75 (s, 1H, olefinic), 3.98 (d, J=5.6 Hz, 2H, allylic), 3.23 (br t, 2H, NCH$_2$), 2.74 (br t, 2H, benzylic), 2.27 (s, 3H, CH$_3$), 1.98 (m, 2H, CH$_2$), 1.63 (s, 4H, 2CH$_2$), 1.24 (s, 6H, 2CH$_3$), 1.23 (s, 6H, 2CH$_3$).

EXAMPLE 61

Preparation of Compound 140a According to Scheme X

Ethyl (2E,4E)-3-methyl-6-oxo-6-[5,6,7,8-tetrahydro-5,5,8,8-tetramethyl(2,3)naphthyl[b]piperidin-1-yl]hexa-2,4-dienoate (structure 42, where $R_1$, $R_2$, $R_3$, $R_4$, and $R_{19}$ are methyl; $R_5$, $R_6$, $R_7$, $R_8$, $R_9$, and $R_{10}$ are hydrogen; $R_{15}$ is ethoxy; X, Y, and Z are carbon; m=1, and n=0)

5,6,7,8-Tetrahydro-5,5,8,8-tetramethyl(2,3)naphthyl[b]piperidine (from Example 57) was coupled with ethyl (2E,4Z)-3-methyl-5-carboxylic acid-penta-2,4-dienoate [prepared by Jone's oxidation of ethyl (2E,4E)-(3-methyl-5-formyl)-penta-2,4-dienoate of Example 4] in the presence of DCC and DMAP and CSA as catalyst in $CH_2Cl_{12}$ to give the title ester: $R_f$=0.50 (50% ether in hexane); $^1$H NMR (400 MHz, $CDCl_3$) δ 7.35 (d, J=15.3 Hz, 1H, olefinic), 7.08 (s, 1H, ArH), 6.85 (br s, 1H, ArH), 6.63 (d, J=15.3 Hz, 1H, olefinic), 6.05 (s, 1H, olefinic), 4.18 (q, 2H, $OCH_2$), 3.85 (t, J=6.5 Hz, 2H, $NCH_2$), 2.65 (t, J=6.5 Hz, 2H, benzylic), 2.17 (s, 3H, $CH_3$), 1.95 (m, 2H, $CH_2$), 1.65 (s, 4H, $2CH_2$), 1.25 (m, 9H, $3CH_3$), 1.21 (s, 6H, $2CH_3$)

EXAMPLE 62

Preparation of Compound 140b According to Scheme X (2E,4E)-3-methyl-6-oxo-6-(6,6,9,9-tetramethyl-3,4,6,7,8,9-hexahydro-2H-benzo[g]quinolin-1-yl)hexa-2,4-dienoic acid (structure 41, where $R_1$, $R_2$, $R_3$, $R_4$, and $R_{19}$ are methyl; $R_5$, $R_6$, $R_7$, $R_8$, $R_9$, and $R_{10}$ are hydrogen; X, Y, and Z are carbon; m=1, and n=0)

The title compound was prepared from compound 140a using the standard hydrolysis conditions described in Example 2. Compound 140b had $R_f$=0.25 (in ether); mp 225–227° C.; $^1$H NMR (400 MHz, $CDCl_3$) δ 7.37 (d, J=15.3 Hz, 1H, olefinic), 7.08 (s, 1H, ArH), 6.87 (br s, 1H, ArH), 6.67 (d, J=15.3 Hz, 1H, olefinic), 6.08 (s, 1H, olefinic), 3.86 (t, J=6.5 Hz, 2H, $NH_2$), 2.68 (t, J=6.5 Hz, 2H, benzylic), 2.19 (s, 3H, $CH_3$), 1.96 (m, 2H, $CH_2$), 1.66 (s, 4H, $2CH_2$), 1.27 (s, 6H, $2CH_3$), 1.98 (s, 6H, $2CH_3$).

EXAMPLE 63

Preparation of Compound 141a According to Scheme XI

Ethyl (2E,4E)-3-methyl-6-oxo-6-[(2,3,5,6,7,8-hexahydro-5,5,8,8-tetramethyl)-benzo[f]indol-1-yl]hexa-2,4-dienoate (structure 47, where $R_1$, $R_2$, $R_3$, $R_4$, and $R_{19}$ are methyl; $R_5$, $R_6$, $R_9$ and $R_{10}$ are hydrogen; $R_{15}$ is ethoxy; X is carbon; m=1, and n=0)

2,5-Dimethyl-2,5-dichlorohexane was coupled with oxindole in $CH_2Cl_2$ at 25° C. in the presence of $AlCl_3$ to obtain 2,3,5,6,7,8-hexahydro-5,5,8,8-tetramethyl-1H-benz-[f]-2-oxo-indole, which was reduced with DIBAL in $CH_2Cl_2$ at reflux temperature to give 2,3,5,6,7,8-hexahydro-5,5,8,8-tetramethyl-1H-benz[f]-indole: $^1$H NMR (400 MHz, $CDCl_3$) δ 7.08 (s, 1H, ArH), 6.61 (s, 1H, ArH), 3.51 (t, J=8.0 Hz, 2H, N-$CH_2$), 2.98 (t, J=8.1 Hz, 2H, benzylic), 1.64 (s, 4H, $2CH_2$), 1.24 (s, 6H, $2CH_3$), 1.23 (s, 4H, $2CH_2$).

The above indole was then coupled with ethyl (2E,4E)-3-methyl-5-carboxylic acid-pent-2,4-dienoate (Example 61) using DCC and DMAP as reagents and CSA as a catalyst in $CH_2Cl_2$ at −78° C. to give the title ester: $R_f$=0.50 (50% ether in hexane); $^1$H NMR (400 MHz, $CDCl_3$) δ 8.32 (s, 1H, ArH), 7.44 (d, J=15.1 Hz, 1H, olefinic), 7.15 (s, 1H, ArH), 6.62 (d, J=15.1 Hz, 1H, olefinic), 6.06 (s, 1H, olefinic), 4.20 (m, $CH_2$; $OCH_2$), 3.19 (brt, J=9.3 Hz, 2H, benzylic), 2.30 (s, 3H, $CH_3$), 1.68 (s, 4H, $2CH_2$), 1.31 (m, 9H, $3CH_3$), 1.26 (s, 6H, $2CH_3$)

EXAMPLE 64

Preparation of Compound 141b According to Scheme XI (2E,4E)-3-Methyl-6-oxo-6-[(2,3,5,6,7,8-hexahydro-5,5,8,8-tetramethyl)benzo-[f]-indol-1-yl]hexa-2,4-dienoic acid (structure 46, where $R_1$, $R_2$, $R_3$, $R_4$, and $R_{19}$ are methyl; $R_9$ and $R_{10}$ are hydrogen; X, and Y are carbon; and m=1)

The title acid was prepared from compound 141a using the standard hydrolysis conditions described in Example 2. Compound 141b had $R_f$=0.15 (50% ether in hexane); mp 226–228° C.; $^1$H NMR (400 MHz, $CDCl_3$) δ8.33 (s, 1H, ArH), 7.47 (d, J=15.1 Hz, 1H olefinic), 7.16 (s, 1H, ArH), 6.67 (d, J=15.1 Hz, 1H, olefinic), 6.11 (s, 1H, olefinic), 4.21 (t, J=8.1 Hz, 2H, $NCH_2$), 3.20 (t, J=8.1 Hz, 2H, benzylic), 2.36 (s, 3H, $CH_3$), 1.68 (s, 4H, $2CH_2$) 1.32 (s, 6H, $2CH_3$), 1.27 (s, 6H, $2CH_3$).

EXAMPLE 65

Preparation of Compound 142a According to Scheme XI

Ethyl (2E,4E)-3-methyl-6-(2,3,5,6,7,8-hexahydro-5,5,8,8-tetramethylbenzo-[f]-indol-1-yl]hexa-2,4-dienoate (structure 46,where $R_1$, $R_2$, $R_3$, $R_4$ and $R_{19}$ are methyl; $R_9$ and $R_{10}$ are hydrogen; $R_{15}$ is ethoxy; X and Y are carbon; and m=1)

2,3,5,6,7,8-Hexahydro-5,5,8,8-tetramethyl-1H-benz-[f]-indole (prepared previously in Example 63) was coupled with (2E,4E)-3-methyl-6-bromo-hexa-2,4-dienoate (prepared previously in Example 57) using NaH as base and THF as solvent to give the title compound: $R_f$=0.80 (50% ether in hexanes); $^1$H NMR (400 MHz, $CDCl_3$) δ 6 7.05 (s, 1H, ArH), 6.42 (s, 1H, ArH), 6.41 (d, J=16.4 Hz, 1H, olefinic), 6.19 (m, 1H, olefinic), 5.85 (s, 1H, olefinic), 4.16 (q, 2H, $OCH_2$), 3.80 (d, J=5.7 Hz, 2H, $NCH_2$,allylic), 3.30 (t, J=8.0 Hz, 2H, $NCH_2$), 2.91 (t, J=8.0 Hz, 2H, benzylic), 2.28 (s, 3H, $CH_3$), 1.64 (s, 6H, $2CH_3$), 1.27 (m, 9H, $3CH_3$).

EXAMPLE 66

Preparation of Compound 142b According to Scheme XI (2E,4E)-3-Methyl-6-(2,3,5,6,7,8-hexahydro-5,5,8,8-tetramethylbenzo[f]indol -1-yl]hexa-2,4-dienoic acid (structure 47, where $R_1$, $R_2$, $R_3$, $R_4$, and $R_{19}$ are methyl; $R_9$ and $R_{10}$ are hydrogen; $_{15}$S is hydroxy; X and Y are carbon; and m=1)

The title compound was prepared from compound 142a using the standard hydrolysis conditions described in Example 2. Acid 142b had $R_f$=0.30 (50% ether in hexane); mp 170–171° C.; $^1$H NMR (400 MHz, $CDCl_3$) δ 7.06 (s, 1H, ArH), 6.41 (s, 1H, ArH), 6.39 (d, H=16.2 Hz, 1H, olefinic), 6.28 (m, 1H, olefinic), 5.79 (s, 1H, olefinic), 3.81 (d, J=5.7 Hz, 2H, N—$CH_2$, allylic), 3.30 (t, J=8.1 Hz, 2H, $NCH_2$), 2.92 (t, J=8.1 Hz, 2H, benzylic), 2.30 (s, 3H, $CH_3$), 1.64 (s, 4H, $2CH_2$), 1.23 (s, 12H, $4CH_3$).

EXAMPLE 67

Preparation of Compound 143a According to Scheme XII

Ethyl (2E,4E)-3-methyl-6-(7,7,10,10-tetrahydro-5,5,8,8-tetramethyl)benzo[f]quinolin-4-yl)hexa-2,4-dienoate (structure 50,where $R_1$, $R_2$, $R_3$, $R_4$, and $R_{19}$ are methyl; $R_9$ and $R_{10}$ are hydrogen; $R_{15}$ is ethoxy; X and Y are carbon; m=1, and n=0)

2,3,6,7,8,9-Hexahydro-6,6,9,9-tetramethyl-1H-cyclopenta[a]naphthalen-3-one (prepared previously in Example 51) was coupled with $H_2NOH$-HCl to give the oxime which, without further purification, was subjected to LAH reduction to give 5,6,7,8-tetrahydro-5,5,8,8-tetramethyl(1,2)-naphthyl-[b]-piperidine: $^1$H NMR (400 MHz, $CDCl_3$) δ 6.95 (d, J=8.7 Hz, 1H, ArH), 6.32 (d, J=8.7 Hz, 1H, ArH), 3.25 (t, J=6.3 Hz, 2H, $NCH_2$), 2.90 (t, J=6.0 Hz, 2H, benzylic), 1.87 (m, 2H, $CH_2$), 1.61 (m, 4H, $2CH_2$), 1.40 (s, 6H, $2CH_3$). 1.22 (s, 6H, $2Ch_3$)

The above piperidine was then converted to the title compound in a manner similar to that of compound 89a as described in Example 59. Compound 143a had $R_f$=0.75 (20% ether in hexane); $^1$H NMR (400 MHz, CDCl$_3$) δ 7.05 (d, J=8.7 Hz, 1H, ArH), 6.46 (d, J=8.7 Hz, 1H, ArH), 6.24 (d, J=15.8 Hz, 1H, olefinic), 6.13 (m, 1H, olefinic), 5.73 (s, 1H, olefinic), 4.15 (q, J=7.2 Hz, 2H, OCH$_2$), 3.94 (d, J=4.8 Hz, 2H, N—CH$_2$-allylic), 3.17 (t, J=6.3 Hz, 2H, N—Ch$_2$), 2.90 (t, J=5.9 Hz, 2H, benzylic), 2.26 (s, 3H, CH$_3$), 1.97 (m, 2H, CH$_2$), 1.62 (m, 6H, 2CH$_2$), 1.27 (t, J=7.2 Hz, 3H, CH$_3$), 1.24 (s, 6H, 2CH$_3$).

EXAMPLE 68

Preparation of Compound 143b According to Scheme XII (2E,4E)-3-Methyl-6-(1,2,3,4,7,8,9,10-octahydro-7,7,10,10-tetramethylbenzo[f]quinolin-4-yl)hexa-2,4-dienoic acid (structure 50, where R$_1$, R$_2$, R$_3$, R$_4$, and R$_{19}$ are methyl; R$_9$ and R$_{10}$ are hydrogen; R$_{15}$ is hydroxy; X and Y are carbon; m=1, and n=0)

The title compound was prepared from compound 143a using the standard hydrolysis conditions in Example 2. Compound 143b had $R_f$=0.50 (50% ether in hexane); amorphous solid HRMS Calc. C$_{26}$H$_{33}$O$_2$N 367.2511, found 367.2504; $^1$H NMR (400 MHz, CDCl$_3$) δ 7.06 (d, J=8.7 Hz, 1H, ArH), 6.46 (d, J=8.7 Hz, 1H, ArH), 6.28 (d, J=15.7 Hz, 1H, olefinic), 6.22 (m, 1H, olefinic), 5.75 (s, 1H, olefinic), 3.95 (d, J=4.7 Hz, 2H, N—CH$_2$-allylic), 3.18 (t, J=6.2 Hz, 2H, N—CH$_2$), 2.90 (t, J=6.0 Hz, 2H, benzylic), 2.27 (s, 3H, CH$_3$), 1.90 (m, 2H, CH$_2$), 1.61 (m, 4H, 2CH$_2$), 1.40 (s, 6H, 2CH$_3$), 1.27 (s, 6H, 2CH$_3$).

EXAMPLE 69

Preparation of Compound 144b According to Scheme II (2E,4E)-3-Methyl-6-[(Z)-5,6,7,8-tetrahydro-5,5,8,8-tetramethylnaphthyl-(2,3-b-pyran-4-ylidene]hexa-2,4-dienoic acid (structure 7, where R$_1$, R$_2$, R$_3$, R$_4$ and R$_{19}$ are methyl; R$_5$, R$_6$, R$_7$, R$_8$, R$_9$ and R$_{10}$ are hydrogen; R$_{15}$ is hydroxy; X and Y are carbon; Z is oxygen; m=n=1).

The title compound was prepared in a manner similar to that of compounds 56a and 56b (Examples 10 and 11) except that 6,6,9,9-tetramethyl-6,7,8,9-tetrahydrobenzo[g]-chromene-4-one was used as the starting ketone (structure 1 in Scheme II). The synthesis of this intermediate ketone is detailed below.

A 200 ml round bottom flask was flame dried under nitrogen and charged with sodium metal (3.2 g, 140 mmol). A solution of 3-aceto-5,6,7,8-tetrahydro-5,5,8,8-tetramethyl-2-naphthol (15 g, 61.0 mmol, from Example 7) in ethyl formate (350 ml) was added dropwise over 1 h. The resulting yellow solution was stirred at 35° C. for 4 h. The mixture was cooled to 25° C. solution, diluted with 1N HCl (20 ml) and extracted with ether. The extracts were washed with water, brine, and dried over MgSO$_4$. The extracts were concentrated under vacuum to give 2-hydroxy-6,6,9,9-tetramethyl-2,3,6,7,8,9-hexahydrobenzo[g]chromen-4-one structure 1 where R$_1$, R$_2$, R$_3$, and R$_4$ are methyl; R$_5$, R$_6$, and R$_7$ are hydrogen; R$_8$ is hydroxy; X and Y are carbon; Z is oxygen; and m=n=1)]: $^1$H NMR (400 MHz, CDCl$_3$) δ 7.85 (s, 1H), 6.9 (s, 1H), 5.85 (t, 1H), 3.32 (br s, 1H), 2.9 (dd, 2H), 1.67 (s, 4H), 1.27 (s, 12H).

To a solution of above benzochromen-4-one (19.6 g, 71.5 mmol) in methanol (250 ml) was added conc HCl (0.5 ml) dropwise. The mixture was stirred at 60° C. for 2.5 h. TLC analysis indicated the reaction was complete. The mixture was cooled to 25° C. and diluted with water (200 ml). A light brown solid precipitate was collected by filtration and dissolved in ether, washed with water, brine and dried over sodium sulfate. Concentration under vacuum gave 6,6,9,9-tetramethyl-6,7,8,9-tetrahydrobenzo[g]chromen-4-one (13.3 g, 52.0 mmol, 73%) as a light brown solid: mp 202.1° C.; $^1$H NMR (400 MHz, CDCl$_3$) δ 8.15 (s, 1H), 7.8 (d, 1H), 7.4 (s, 1H), 6.25 (d, 1H), 1.75 (s, 4H), 1.35 (s, 12H).

A solution of 6,6,9,9-tetramethyl-6,7,8,9-tetrahydrobenzo[g]chromen-4-one (4.4 g, 17.2 mmol) in 1:1 EtOAc/methanol (250 ml) containing 10% palladium on carbon (1:1 g, 7% by weight) was stirred at room temperature under an atmosphere of hydrogen (balloon) for 14 h. TLC analysis indicated complete reaction. The mixture was filtered and concentrated to give a yellow oil. The oil was passed through a small column of silica (10% EtOAc in hexane) and concentration to give 6,6,9,9-tetramethyl-2,3,6,7,8,9-hexahydrobenzo[g]chromen-4-one (4.2 g, 16.3 mmol, 95%) as a light yellow solid: $^1$H NMR (400 MHz, CDCl$_3$) δ 7.85 (s, 1H), 6.86 (s, 1H), 4.46 (t, 2H), 2.75 (t, 2H), 1.65 (s, 4H), 1.25 (s, 12H).

The above hexahydrobenzo[g]chromen-4-one was transformed to the title compound as outlined in Scheme II and Examples 10 and 11. Compound 144b was obtained as a bright yellow solid: mp 228.5° C.; $R_f$=0.26 (40% ether in hexane); $^1$H NMR (400 MHz, CDCl$_3$) δ7.42 (dd, 1H), 7.38 (s, 1H), 6.8 (s, 1H), 6.4 (d, 1H), 6.07 (d, 1H), 5.32 (s, 1H), 4.32 (t, 2H), 2.66 (t, 2H), 2.35 (s, 3H), 1.68 (s, 4H), 1.28 (s, 6H), 1.26 (s, 6H).

EXAMPLE 70

Preparation of Compound 145b According to Scheme II (2E,4E)-3-methyl-6-[(E)-3,4,5,6,7,8-hexahydro-2,2,5,5,8,8-hexamethyl-2H-anthracen-1-ylidene]hexa-2,4-dienoic acid (structure 7, where R$_1$, R$_2$, R$_3$, R$_4$, R$_5$, R$_6$, and R$_{19}$ are methyl; R$_7$, R$_8$, R$_9$, and R$_{10}$ are hydrogen; R$_{15}$ is hydroxy; X, Y, Z are carbon; m=n=1)

The title compound was prepared in a manner similar to Example 10, except that 2,5,5,8,8-3,4,5,6,7,8-hexahydro-2,2,5,5,8,8-hexamethyl-2H-anthracen-1-one was used as the starting tricyclic ketone which was prepared by the following sequence.

The tricyclic ketone, 2,5,5,8,8-3,4,5,6,7,8-hexahydro-2,5,5,8,8-pentamethyl-2H-anthracen-1-one (0.640 g, 2.50 mmol) in THF (5.00 mL) was added dropwise to a prepared solution of LDA (2.75 mmol, 1.1 eq) in THF at −78° C. The resulting blue-green solution was stirred at −78° C. for 45 min. Iodomethane (0.707 g, 5.00 mmol, 0.311 mL) was added dropwise and the solution was stirred for 1 h at −78° C. The reaction solution was warmed to room temperature and became red in color. After stirring for 1.5 h, the reaction solution was quenched with water and the aqueous layer extracted with EtOAc (3×10 mL). The combined organic extracts were washed with H$_2$O and brine, dried (MgSO$_4$), filtered, and concentrated to give the crude methylated tricycle (0.687 g). Purification by radial chromatography (20:1 =Hex:THF) gave the dimethylated tricycle (0.090 g, 13%) as a white solid: $^1$H NMR (400 MHz, CDC3) δ 8.02 (s, 1H, Ar-H), 7.13 (s, 1H, Ar-H), 2.92 (t, 2H, 2CH), 1.95 (t, 2H, 2CH), 1.67 (s, 4H, CH$_2$), 1.30 (s, 6H, 2CH$_3$), 1.29 (s, 6H, 2CH$_3$), 1.21 (s, 6H, 2CH$_3$).

Procedures similar to those in Examples 10 and 11 afforded the compound 145b as a yellow solid. $^1$H NMR (400 MHz, CDCl$_3$) δ 7.22 (s, 1H, Ar-H), 7.18 (dd, J=11.0, 15.2 Hz, 1H, olefinic), 7.07 (s, 1H, Ar-H), 6.41 (d, J=15.2 Hz, 1H, olefinic), 6.28 (d, J=11.0 Hz, 1H, olefinic), 5.80 (s, 1H, olefinic), 2.76 (t, J=6.6 Hz, 2H, CH$_2$), 2.28 (s, 3H, CH$_3$), 1.69 (s, 4H, CH$_2$), 1.68 (t, J=6.6 Hz, 2H, CH$_2$), 1.29 (s, 12H, 4CH$_3$), 1.16 (s, 6H, 2CH$_3$).

EXAMPLE 71

Preparation of Compound 146a According to Scheme II

Ethyl (2E,4E)-3-methyl-6-[(Z)-N-acetyl-3,4,5,6,7,8-hexahydro-10-amino-5,5,8,8-tetramethyl-2H-anthracen-1-ylidene]hexa-2,4-dienoate (structure 7,where $R_1$, $R_2$, $R_3$, $R_4$, and $R_{19}$ are methyl; $R_5$, $R_6$, $R_7$, $R_8$ and $R_{10}$ are hydrogen; $R_9$ is N-acetylamino; $R_{15}$ is ethoxy; X, Y, Z are carbon; m=n=1)

The title compound was prepared in a manner similar to Example 10,except that 10-nitro-1,2,3,4,5,6,7,8-octahydro-5,5,8,8-tetramethylanthracen-1-one (from Example 8) was used as the starting tricyclic ketone and generation of the intermediate cis-olefinic ester was accomplished with catalytic TsOH in EtOH; the 10-nitrotricyclic cis-allylic alcohol was prepared from the ester as described in Example 10: $^1$H NMR (400 MHz, CDCl$_3$) δ 7.32 (s, 1H, aromatic), 5.71 (t, J=6.8 Hz, 1H, olefinic), 4.36 (collapsed dd, 2H, allylic), 2.59 (apparent t, J=6.6 Hz, 2H, CH$_2$), 2.42 (m, 2H, CH$_2$), 1.91 (m, 2H, CH$_2$), 1.73 (m, 2H, Ch$_2$), 1.68 (m, 2H, CH$_2$), 1.57 (s, 6H, 2CH$_3$), 1.31 (s, 6H, 2CH$_3$).

The intermediate 10-nitrotricyclic cis-allylic alcohol (250 mg, 0.76 mmol) in EtOH (4.5 mL) and water (1.0 mL) was treated with calcium chloride (54 mg) in water (0.1 mL) and zinc dust (1.63 g) at ambient temperature and the mixture was heated at reflux for 2 h. The hot mixture was filtered through a pad of celite and the filter pad was rinsed with hot EtOH (50 mL). The solution was concentrated in vacuo, diluted with water and extracted with EtOAc. The EtOAc layer was washed with water, saturated aqueous NaHCO$_3$, water, and brine. The solution was dried (Na$_2$SO$_4$), filtered, and concentrated to give 10-aminotricyclic cis-allylic alcohol, 225 mg (99%) as a yellow oil: $_1$H NMR (400 MHz, CDCl$_3$) δ 6.66 (s, 1H, aromatic), 5.56 (t, J=6.5 Hz, 1H, olefinic), 4.46 (d, J=6.5 Hz, 2H, allylic), 3.82 (broad s, 2H, 2.51 (m, 2H, CH$_2$), 2.38 (m, 2H, CH$_2$), 2.04 (m, 2H, CH$_2$), 1.73 (m, 2H, CH$_2$), 1,73 (m, 2H, CH$_2$), 1.64 (m, 2H, CH$_2$), 1.45 (s, 6H, 2CH$_3$), 1.29 (s, 6H, 2CH$_3$).

The amino alcohol (200 mg, 0.67 mmol), in methylene chloride (1 mL) and lutidine (0.2 mL) was treated with t-butyldimethylsilyl triflate (195 mg, 0.74 mmol) at ambient temperature and the solution was allowed to stir for 8 h. The reaction was quenched with saturated aqueous NH$_4$Cl and diluted with EtOAc. The EtOAc layer was washed with water, saturated aqueous NaHCO$_3$, water, and brine. The solution was dried (Na$_2$SO$_4$), filtered, and concentrated to give the crude product. The product was purified by silica gel radial chromatography (20:1=Hex:EtOAc) to give the 10-amino silyl protected cis-allylic alcohol 128 mg (46%) as a colorless oil: $^1$H NMR (400 MHz, CDCl$_3$) δ 6.71 (s, 1H, aromatic), 5.57 (t, J=6.2 Hz, 1H, olefinic), 4.53 (d, J=6.2 Hz, 2H, allylic), 3.84 (broad s, 2H, NH$_2$), 2.54 (apparent t, J=6.7 Hz, 2H, CH$_2$), 2.42 (m, 2H, CH$_2$), 2.06 (m, 2H, CH$_2$), 1.77 (m, 2H, CH$_2$), 1.68 (m, 2H, CH$_2$), 1.49 (s, 6H, 2CH$_3$), 1.34 (s, 6H, 2CH$_3$), 0.96 (s, 6H, 2CH$_3$).

The 10-amino silyl protected cis-allylic alcohol (95 mg, 0.23 mmol), in methylene chloride (2 nmL) and pyridine (0.3 mL) was treated with a catalytic amount of DMAP and acetic anhydride (1.15 mmol) and the solution was heated at reflux for 12 h. The reaction was quenched with the adition of water and diluted with EtOAc. The EtOAc layer was washed with water, saturated aqueous NaHCO$_3$, water, and brine. The solution was dried (Na$_2$SO$_4$), filtered, and concentrated to give the crude product. The product was purified by silica gel radial chromatography (1:1=Hex:Et$_2$O) to give the N-acyl-10-amino silyl protected cis-allylic alcohol 67 mg (70%) as a colorless oil. The protected cis-allylic alcohol (0.16 mmol) was dissolved in THF (0.5 mL) and treated with tetrabutylammonium fluoride (1M, 2.1 eq) at ambient temperature and the solution was allowed to stir for 8 h. The reaction was quenched with water and diluted with EtOAc. The EtOAc layer was washed with water, saturated aqueous NaHCO$_3$, water, and brine. The solution was dried (Na$_2$SO$_4$), filtered, and concentrated to give the crude product. The product was crystallized (CH$_2$Cl$_2$/hexanes) to give the N-acyl-10-amino cis-allylic alcohol 44 mg (89%) as a yellow solid. The alcohol (0.13 mmol) was oxidized with MnO$_2$ (20 mg, 0.23 mmol) in methylene chloride (0.5 mL) at ambient temperature for 18 hours. The reaction was quenched with the addition of water and diluted with EtOAc. The EtOAc layer was washed with water, saturated aqueous NaHCO$_3$, water, and brine. The solution was dried (Na$_2$SO$_4$), filtered, and concentrated to give the N-acyl-10-amino cis-unsaturated aldehyde 43 mg (99%) as a yellow oil: $^1$H NMR (400 MHz, CDCl$_3$) δ 9.78 (d, J=7.9 Hz, 1H, CHO), 7.02 (s, 1H, aromatic), 6.02 (d, J=7.9 Hz, 1H, olefinic), 2.69 (m, 2H, CH$_2$), 2.58 (m, 2H, CH$_2$), 2.23 (s, 3H, CH$_3$), 1.92 (m, 2H, CH$_2$), 1.69 (m, 4H, 2CH$_2$), 1.40 (m, 6H, 2CH$_2$), 1.27 (s, 6H, 2CH$_3$).

Using the procedure described in Example 1,the above aldehyde was transformed into the title compound 146a, which was obtained as a yellow oil: $^1$H NMR (400 MHz, CDCl$_3$) δ7.34 (s, 1H, aromatic), 7.13 (dd, J=15.1, 11.1 Hz, 1H, olefinic), 6.43 (d, J=15.1 Hz, 1H, olefinic), 6.15 (d, J=11.1 Hz, 1H, olefinic), 5.80 (broad s, 1H, olefinic), 4.14 (q, J=7.0 Hz, 2H, —OCH$_2$); 2.64 (m, 2H, CH$_2$), 2.48 (m, 2H, CH$_2$), 2.29 (s, 3H, CH$_3$), 2.22 (s, 3H, CH$_3$ allylic), 1.94 (m, 2H, CH$_2$), 1.87 (m, 2H, CH$_2$), 1.69 (m, 2H, CH$_2$), 1.30 (s, 12H, 4CH$_3$); 1.28 (t, J=7.0 Hz, 3H, CH$_3$ ethyl).

EXAMPLE 72

Preparation of Compound 146b According to Scheme II (2E,4E)-3-methyl-6-[(Z)-N-acetyl-3,4,5,6,7,8-hexahydro-10-amino-5,5,8,8-tetramethyl-2H-anthracen-1-ylidene] hexa-2,4-dienoic acid (structure 7,where $R_1$, $R_2$, $R_3$, $R_4$, and $R_{19}$ are methyl; $R_5$, $R_6$, $R_7$, $R_8$ and $R_{10}$ are hydrogen; $R_9$ is N-acetylamino; $R_{15}$ is hydroxy; X, Y, Z are carbon; m=n=1)

Compound 143a was hydrolyzed using the procedure of Example 2, to give the title compound 143b 20.5 mg (30%) as a yellow film: $^1$H NMR (400 MHz, CDCl$_3$) δ 7.36 (s, 1H, aromatic), 7.16 (dd, J=15.1, 11.1 Hz, 1H, olefinic), 6.73 (s, 1H, NH), 6.36 (d, J=15.1 Hz, 1H, olefinic), 6.18 (d, J=11.1 Hz, 1H, olefinic), 5.81 (broad s, olefinic), 2.64 (m, 2H, CH$_2$), 2.48 (m, 2H, CH$_2$), 2.29 (s, 3H, CH$_3$), 2.22 (s, 3H, CH$_3$), 1.94 (m, 2H, CH$_2$), 1.94 (m, 2H, CH$_2$), 1.87 (m, 2H, CH$_{2),}$ 1.69 (m, 2H, CH$_2$), 1.30 (s, 12H, 4CH$_3$).

EXAMPLE 73

Preparation of compound 147b according to Scheme XIII (2E,4E)-3-methyl-6-[(E)1-ethyl-6,6,9,9-tetramethyl-2,3,6,7,8,9-hexahydro-1H-benzo[g]quinolin-4-ylidene]hexa-2,4-dienoic acid (structure 7, where $R_1$, $R_2$, $R_3$, $R_4$, and $R_{19}$ are methyl; $R_5$, $R_6$, $R_7$, $R_8$, $R_9$ and $R_{10}$ are hydrogen; $R_{15}$ is hydroxy; X, Y are carbon, Z is N-ethyl; m=n=1)

The title compound was prepared in a manner similar to Example 1 except that 1-ethyl-6,6,9,9-tetramethyl-2,3,6,7,8,9-hexahydro-1H-benzo[g]quinolin-4-one was used as the starting tricyclic ketone, which was prepared by the following sequence.

Nitric acid (15.3 g, 218 mmol ) was added dropwise to 1,2,3,4-tetrahydro-1,1,4,4 tetramethylnaphthalene (13.7 g, 72.9 mmol ) at 0° C. Following this addition, the reaction mixture was allowed to warm to 25° C. over 2 hours. The reaction mixture was poured onto ice (200 g), neutralized by addition of sodium carbonate and extracted with ethyl acetate. Removal of solvent under reduced pressure yielded a light brown oil which crystallized upon standing (15.7 g, 68.0 mmol, 93% ): $^1$H NMR (400 MHz, $CDC_{13}$) δ 8.17 (d, 1H, ArH), 7.95 (dd, 1H, ArH), 7.45 (d, 1H, ArH), 1.75 (br s, 4H, $CH_2$), 1.32 (s, 6H, $CH_3$), 1.28(s, 6H, $CH_3$).

A solution of 1,1,4,4-tetramethyl-6-nitro-1,2,3,4-tetrahydronaphthalene (1 5.7 g, 68.0 mmol) and 10% palladium on carbon (1.57 g ) in ethyl acetate (190 ml) was stirred under an atmosphere of hydrogen at 25° C. for 24 hours. Filtration through celite and removal of solvent under reduced pressure yielded the amine as a golden brown oil (13.2 g, 65.7 mmol, 96% ): $^1$H NMR (400 MHz, $CDC_{13}$) δ 7.10 (d, 1H, ArH), 6.63(d, 1H, ArH), 6.50 (dd, 1H, ArH), 3.50 (br s, 2H, $NH_2$), 1.65 (br s, 4H, $CH_2$), 1.28 (s, 6H, $CH_3$), 1.26(s, 6H, $CH_3$).

A solution of 2-amino-5,5,8,8-tetramethyl-5,6,7,8-tetrahydronaphthalene (3.0 g, 14.8 mmol) and acrylic acid (1.0 g, 14.8 mmol ) in toluene (60 ml ) was heated to reflux for 14 hours. Removal of solvent under reduced pressure yielded a viscous brown oil (3.0 g, 10.9 mmol, 74%): $^1$H NMR (400 MHz, $CDC_{13}$) 8 7.16 (d, 1H, ArH), 6.62 (d, 1H, ArH), 6.54 (dd, 1H, ArH), 3.48 (t, 2H, N—$CH_2$), 2.68 (t, 2H, $CH_2$), 1.67 (br s, 4H, $CH_2$), 1.28 (s, 6H, $CH_3$), 1.26 (s, 6H, $CH_3$).

2-amino-3-(5,5,8,8-tetramethyl-5,6,7,8-tetrahydronaphthalene)-propionic acid (3.0 g, 10.9 mmol ) was dissolved into PPA (100 ml) and stirred at 100° C. for 16 hours. The red reaction mixture was poured onto ice (200 g), neutralized by addition of sodium carbonate and extracted with ethyl acetate. Removal of solvent under reduced pressure yielded a yellow semisolid. Column chromatography (10% EtOAc/Hex) gave the desired product as a yellow solid (2.2 g, 8.6 mmol, 79% ): $^1$H NMR (400 MHz, $CDC_{13}$) δ 7.80 (s, 1H, ArH), 6.60 (s, 1H, ArH), 3.55 (t, 2H, N—$CH_2$), 2.68 (t, 2H, $CH_2$), 1.65 (br s, 4H, $CH_2$), 1.28 (s, 6H, $CH_3$), 1.26(s, 6H, $CH_3$).

A solution of 6,6,9,9-tetramethyl-2,3,6,7,8,9-tetrahydro-1H-benzo[g]quinoline-4-one (255 mg, 1.0 mmol), iodoethane (2.0 g, 12.4 mmol ), and anhydrous potassium carbonate (1.4 g, 10.0 mmol) in DMA (50 ml) was stirred at 50–60° C. for 48 hours. The reaction mixture was diluted with water and extracted with ethyl acetate. Removal of solvent under reduced pressure yielded a yellow/brown oil (150 mg) which partially solidified on standing. Column chromatography (10%–20% EtOAc/Hex) gave the desired product as a bright yellow/green solid (80 mg, 0..28 mmol, 28% ): $^1$H NMR (400 MHz, $CDCl_3$) δ 7.85 (s, 1H, ArH), 6.63 (s, 1H, ArH), 3.40 (q, 2H, N—$CH_2$), 3.38 (t, 2H, N—$CH_2$), 2.65 (t, 2H, $CH_2$), 1.65 (br s, 4H, $CH_2$), 1.3 (s, 6H, $CH_3$), 1.28(s, 6H, $CH_3$), 1.16 (t, 3H, $CH_3$)

Procedures similar to those in Examples 1 and 2 afforded the title compound 147b as a orange semi-solid material. The final product was purified by HPLC (90/10 MeOH/$H_2O$) to give a yellow solid.: $^1$H NMR (400 MHz, $CDCl_3$) δ 7.46 (s, 1H, ArH), 7.05 (dd, 1H, CH), 6.62 (d, 1H, CH), 6.56 (s, 1H, ArH), 6.42 (d, 1H, CH), 5.83 (br s, 1H, CH), 3.38 (q, 2H, N—$CH_2$), 3.26 (t, 2H, N—$CH_2$), 2.83 (t, 2H, $CH_2$), 2.40 (s, 3H, $CH_3$), 1.67 (br s, 4H, $CH_2$), 1.28 (s, 6H, $CH_3$), 1.26(s, 6H, $CH_3$), 1.15 (t, 3H, $CH_3$).

EXAMPLE 74

Preparation of Compound 148b According to Scheme XIII

T-butyl-4-(5-carboxy-penta-2E-4E-dieneylidene)-6,6,9,9-tetramethyl-3,4,6,7,8,9-hexahydro-2H-benzo[g]quinolin-1-carboxylate (structure 54,where $R_1$, $R_2$, $R_3$, $R_4$, and $R_{19}$ are methyl; $R_5$, $R_7$, $R_8$, $R_9$, $R_{10}$, $R_{26}$, $R_{27}$, $R_{28}$, and $R_{29}$, are hydrogen; $R_{15}$ is hydroxy; X, Y are carbon, Z is N-1-carboxylic acid tert-butyl ester; m=n=1)

The title compound was prepared as in Example 73 except for the nitrogen alkylation step which involved the use of t-butylchloroformate. Following the standard hydrolysis procedure of Example 2 gave 50 mg of the title compound obtained as a yellow orange oil. Column chromatography (40% Diethyl ether/Hexane) gave the desired product as a yellow film: $^1$H NMR (400 MHz, $CDCl_3$) δ 7.57 (s, 1H, ArH), 7.43 (s, 1H, ArH), 6.98 (dd, 1H, CH), 6.72 (d, 1H, CH), 6.45 (d, 1H, CH), 5.80 (s, 1H, CH), 3.80 (t, 2H, N—$CH_2$), 2.90 (t, 2H, $CH_2$), 2.38 (s, 3H, $CH_3$), 1.70 (br s, 4H, $CH_2$), 1.50 (s, 9H, $CH_3$), 1.30 (s, 6H, $CH_3$), 1.26(s, 6H, $CH_3$).

EXAMPLE 75

Preparation of Compound 149b According to Scheme XVI (2E,4E)-3-methyl-(6,6,9,9-tetramethyl-2,3,6,9-tetrahydronaphtho[2,3-b]-[1,4]oxazin-4-yl-hexa-2,4-dienoic acid (structure 68, where $R_1$, $R_2$, $R_3$, $R_4$, and $R_{19}$ are methyl; $R_5$, $R_6$, $R_7$, $R_8$, $R_9$, $R_{10}$, $R_{26}$, $R_{27}$, $R_{28}$, and $R_{29}$, are hydrogen; $R_{15}$ is hydroxy; X, Y are carbon, W is nitrogen, Z is oxygen; m=n=1)

To a solution of 6-6-9-9-tetramethyl-6,9-dihydro-4H-naphtho[2,3-b][1,4]oxazin-3-one (400 mg, 1.5 mmol) [prepared by Friedel Crafts alkylation/annulation of 2H-1,4-benzoxazin-3-(4H)-one with 2,5-dichloro-2,5-dimethyl hexane in the presence of aluminum chloride at ambient temperatue (24° C.) in dichloromethane]in THF at ambient temperature was added LiAlH4 (4.6 ml, 4.6 mmol). The reaction mixture was allowed to stir and then was heated to 80° C. for 30 min. The reaction mixture was poured over saturated sodium potassium tartrate solution (100 ml), extracted with EtOAc (100 ml), dried with anhydrous $MgSO_4$ (0.5 g), and concentrated to give 6,6,9,9-tetramethyl-3,4,6,9-tetrahydro-2H-naphtho[2,3-b][1,4] oxazine (300 mg, 70% yield of theory): $^1$H NMR (400 MHz, $CDCl_3$) δ 6.70 (s, 1H, benzylic), 6.52 (s, 1H, benzylic), 4.23 (t, 2H, J=2.8, 1.6 Hz, ring $CH_2$), 3.39 (t, 2H, J=4.4, 6.8 Hz, ring $CH_2$), 1.63 (s, 4H, 2 $CH_2$), 1.22 (s, 12H, 4 $CH_3$).

To a solution of ethyl-6-bromohexa-2,4-dienoate (45 mg, 0.19 mmol) in THF at ambient temperature was added NaH (4 mg, 0.14 mmol) under $N_2$(gas). The solution was stirred for 10 min and then added to 6,6,9,9-tetramethyl-3,4,6,9-tetrahydro-2H-naphtho[2,3-b][1,4]oxazine (24 mg, 0.1 mmol) at ambient temperature. The reaction was then heated to 65° C. overnight. The reaction was then quenched over saturated $NH_4Cl$ solution (100 ml) extracted with EtOAc (100 ml), dried with anhydrous $MgSO_4$ (0.5 g), and concentrated. The product ran on prep tlc plates (20% EtOAc/Hexane) to give ethyl-3-methyl-(6,6,9,9-tetramethyl-2,3,6,9-tetrahydronaphtho [2,3-b][1,4]oxazin-4-yl)hexa-2,4-dienoate (25 mg, 89% yield of theory): $^1$H NMR (400 MHz, $CDCl_3$) δ 6.71 (s, 1H, benzylic), 6.56 (s, 1H, benzylic), 6.31 (d, 1H, J=15.6 Hz, olefinic), 6.17 (dt, 1H, olefinic), 5.57 (s, 1H, olefinic), 4.25 (t, 2H, J=4, 4 Hz, N—$CH_2$), 4.17 (q, 2H, $CH_2CH_3$), 3.95 (d, 2H, J=6.8 Hz, N—$CH_2$), 3.28 (t, 2H, J=4 Hz, ring $CH_2$), 2.27 (s, 3H, $CH_3$), 1.63 (s, 4H, 2$CH_2$), 1.28 (t, 3H, $CH_3$), 1.22 (s, 6H, 2$CH_3$), 1.21 (s, 6H, 2$CH_3$)

Standard hydrolysis conditions, as in Example 2 were used to obtain 3-methyl-(6,6,9,9-tetramethyl-2,3,6,9-tetrahydronaphtho[2,3-b][1,4]oxazin-4-yl)hexa-2,4-dienoic acid (12.5 mg, 88% of theory): $^1$H NMR (400 MHz, $CDC_{13}$) δ 6.71 (s, 1H, benzylic), 6.56 (s, 1H, benzylic), 6.31 (d, 1H, J=15.6 Hz, olefinic), 6.17 (dt, 1H, olefinic), 5.57 (s, 1H, olefinic), 4.25 (t, 2H, J=4, 4 Hz, N—CH$_2$), 3.95 (d, 2H, J=6.8 Hz, ring CH$_2$), 3.28 (t, 2H, J=4 Hz, ring CH$_2$), 2.27 (s, 3H, CH$_3$), 1.63 (s, 4H, 2CH$_2$), 1.22 (s, 6H, 2CH$_3$), 1.21 (s, 6H, 2CH$_3$).

EXAMPLE 76

Preparation of Compound 150b According to Scheme XVI (2E,4E)-3-methyl-6-oxo-6-(6,6,9,9-tetrahydro-2,3,6,9-tetrahydro-naphtho[2,3-b][1,4[oxazin-4-yl)hexa-2,4-dienoic acid (structure 69, where R$_1$, R$_2$, R$_3$, R$_4$, and R$_{19}$ are methyl; R$_5$, R$_6$, R$_7$, R$_8$, R$_9$, R$_{10}$, R$_{26}$, R$_{27}$, R$_{28}$, and R$_{29}$, are hydrogen; R$_{15}$ is hydroxy; X, Y are carbon, W is nitrogen, Z is oxygen; m=n=1).

To a solution of 6,6,9,9-tetramethyl-3,4,6,9-tetrahydro-2H-naphtho[2,3-b][1,4]oxazine (prepared in Example 75, 100 mg, 0.408 mmol) was added hexa-2,4-dienedioic acid mono ethylester (90 mg, 0.489 mmol) in dichloromethane, at ambient temperature. To this solution was added DMAP (50 mg, 0.489 mmol), CSA (47 mg, 0.204 mmol), and DCC (100 mg, 0.489 mmol). The reaction was stirred at ambient temperature for 30 min. EtOAc was added, and the reaction mixture was filtered and evaporated. Prep TLC was used (20% EtOAc/Hexane) to give ethyl-3-methyl-6-oxo-6-(6,6, 9,9-tetrahydro-2,3,6,9-tetrahydro-naphtho[2,3-b][1,4] oxazin-4-yl)hexa-2,4-dienoate (30 mg, 40% yield of theory): $^1$H NMR (400 MHz, CDCl$_3$) δ 7.40 (d, 1H, olefinic), 6.90 (br s, 1H, benzylic), 6.86 (d, 1H, olefinic), 6.85 (s, 1H, benzylic), 6.09 (d, 1H, olefinic), 4.29 (t, 2H, ring CH$_2$), 4.21 (q, 2H, CH$_2$), 4.04 (t, 2H, ring CH$_2$) 2.25 (s, 3H, CH$_3$), 1.62(s, 4H, 2CH$_2$), 1.30 (t, 3H, CH$_3$), 1.28 (s, 6H, 2CH$_3$), 1.22 (s, 6H, 2CH$_3$).

Standard hydrolysis conditions, as in Example 2, were used to obtain 3-methyl-6-oxo-6-(6,6,9,9-tetrahydro-2,3,6, 9-tetrahydronaphtho[2,3-b][1,4]oxazin-4-yl)hexa-2,4-dienoic acid (18 mg, 40% yield of theory): $^1$H NMR (400 MHz, CDCl$_{13}$) 7.43 (d, 1H, olefinic), 6.92 (br s, 1H, benzylic), 6.90 (d, 1H, olefinic), 6.86 (s, 1H, benzylic), 6.13(s, 1H, olefinic), 4.31 (t, 2H, ring CH$_2$), 4.04 (t, 2H, ring CH$_2$), 2.27 (s, 3H, CH$_3$), 1.67 (s, 4H, 2CH$_2$), 1.26 (s, 6H, 2CH$_3$), 1.22 (s, 6H, 2CH$_3$).

EXAMPLE 77

Preparation of Compound 151a According to Scheme XVII (2E,4E)-3-methyl-6-(6-ethyl-1,9,9-trimethyl-7-oxo-2,3,6,7, 8,9-hexahydro-1H-pyrido[2,3-g]quinolin-4-ylidene)hexa-2, 4-dienoic acid (structure 76, where R$_1$ is ethyl; R$_2$, R$_3$, R$_4$, R$_{19}$ and R$_{24}$ are methyl; R$_5$, R$_7$, R$_8$, R$_9$, R$_{10}$ and R$_{28}$ are hydrogen; R$_{15}$ is hydroxy; X, Z are N; Y is carbon; m=n=1)

To a solution of aniline (19.73 g, 0.212mol) in CH$_2$Cl$_2$ (200 ml) at 0° C. was added dropwise 3,3-dimethyl acryloyl chloride (25.0 g, 0.212mol) and triethylamine (21.4 g, 0.212mol) at equal rates. This mixture was allowed to warm to 25° C. and stirred at for 17 hours. The reaction mixture was diluted with water and extracted with ethyl acetate. Removal of solvent under reduced pressure yielded the amide as a fine white fibrous solid (28.9 g, 0.165mol, 78%). $^1$H NMR (400 MHz, CDC$_{13}$) 6 7.52 (br d, 2H, ArH), 7.40 (br s, 1H, NH), 7.28 (t, 2H, ArH), 7.05 (t, 1H, ArH), 5.72 (s, 1H, CH), 2.20 (s, 3H, CH$_3$), 1.86 (s, 3H, CH$_3$).

To a solution of 3-methylbut-2-enoic acid phenylamide (10.0 g, 0.057 mol) in CH$_2$Cl$_2$ (150ml) at 25° C. was added aluminum chloride (5.0 g, 0.037 mol). This mixture was heated to reflux and stirred for 6 hours. The reaction mixture was poured onto ice (30 g) extracted with CH$_2$Cl$_2$. Removal of solvent under reduced pressure yielded the lactam as an off white-solid (9.5 g, 0.054 mol, 95%): $^1$ H NMR (400 MHz, CDCl$_{13}$) δ 9.10 (br s, 1H, NH), 7.32 (d, 1H, ArH), 7.18 (t, 1H, ArH), 7.05 (t, 1H, ArH), 6.85 (d, 1H, ArH), 2.25 (s, 2H, CH$_2$), 1.35 (s, 6H, CH$_{33}$).

4,4-dimethyl-3,4-dihydro-1H-quinolin-2-one (4.5 g, 0.0257mol) was dissolved in sulfuric acid (30 ml) and cooled to 10° C. To this solution was added dropwise fuming nitric acid(2.16 g, 0.031 mol). This mixture was stirred at 10° C. for 30 min and at 25° C. for 2 hours. The reaction mixture was poured onto ice (50 g) and the solid nitro lactam was filtered and rinsed with saturated sodium bicarbonate and water. The nitro lactam was collected as a fine brown powder (5.5 g, 0.025 mol, 97%). $^1$H NMR (400 MHz, CDCl$_3$) δ 8.76 (br s, 1H, NH), 8.21 (d, 1H, ArH), 8.10 (dd, 1H, ArH), 6.90 (d, 1H, ArH), 2.57 (s, 2H, CH$_2$), 1.40 (s, 6H, CH$_3$).

A solution of 4,4-dimethyl-6-nitro-3,4-dihydro-1H-quinolin-2-one (3.0 g, 0.01 36 mol) in THF (20 ml) was added to a solution of sodium hydride (420 mg, 0.017 mol) in THF (30 ml) at 25° C. under nitrogen. This mixture was stirred for 1.5 hours and iodomethane (12.8 g, 0.082 mol) was added all at once. The reaction mixture was heated to 50° C. for 20 hours, quenched by slow addition of water and extracted with ethyl acetate. Removal of solvent under reduced pressure afforded the ethyl lactam as a brown solid (4.5 g). This material was not purified. $^1$H NMR (400 MHz, CDCl$_{13}$) 6 8.19 (d, 1H, ArH), 8.17 (dd, 1H, ArH), 7.12 (d, 1H, ArH), 4.10 (q, 2H, CH$_2$), 2.57 (s, 2H, CH$_2$), 1.35 (s, 6H, CH$_3$), 1.27 (t, 3H, CH$_3$).

1-ethyl-4,4-dimethyl-6-nitro-3,4-dihydro-1H-quinolin-2-one (4.1 g crude) was suspended in a 75% solution of ethanol\water (20 ml). To this mixture was added calcium chloride monohydrate (2.0 g, 0.0136 mol) and zinc dust (30 g, 0.461 mol). The reaction mixture was heated at reflux for 4 hours and stirred at 25° C. for an additional 14 hours. The mixture was diluted with water, filtered and extracted with ethyl acetate. Removal of solvent under reduced pressure gave a brown oil (3.5 g). Column chromatography (50% EtOAc/hex ) afforded the amino lactam as a yellow oil (1.8 g, 8.3 mmol). $^1$H NMR (400 MHz, CDCl$_3$) δ 6.84 (d, 1H, ArH), 6.66 (d, 1H, ArH), 6.57 (dd, 1H, ArH), 3.97 (q, 2H, CH$_2$), 3.57 (br s, 2H, NH$_2$), 2.43 (s, 2H, CH$_2$), 1.27 (s, 3H, CH$_3$), 1.25 (s, 3H, CH$_3$), 1.23(t, 3H, CH$_3$).

A solution of 6-amino-(1-ethyl-4,4-dimethyl-3,4-dihydro-1H-quinolin-2-one) (750 mg, 3.5 mmol) and acrylic acid (252 mg, 3.5 mmol ) in toluene (10 ml) was heated to reflux for 28 hours. Removal of solvent under reduced pressure gave a brown oil (900 mg). Column chromatography (5%–10% MeOH/CHCl$_3$) afforded the amino lactam as a yellow oil (597 mg, 2.1 mmol, 60%): $^1$H NMR (400 MHz, CDCl$_3$) δ 6.90 (d, 1H, ArH), 6.63(d, 1H, ArH), 6.54 (dd, 1H, ArH), 3.98 (q, 2H, CH$_2$), 3.46 (t, 2H, N—CH$_2$), 2.70 (t, 2H, CH$_2$), 2.45 (s, 2H, CH$_2$), 1.27 (s, 3H, CH$_3$), 1.25 (s, 3H, CH$_3$), 1.22(t, 3H, CH$_3$).

3-(1-ethyl-4,4-dimethyl-2-oxo-1,2,3,4-tetrahydro-quinolin-6-yl-amino)propionic acid (597 mg, 2.1 mmol) was dissolved into PPA (5 ml ) and stirred at 100° C. for 16 hours. The red reaction mixture was poured onto ice (20 g), neutralized by addition of sodium carbonate and extracted with ethyl acetate. Removal of solvent under reduced pressure gave the tricyclic ketone as a yellow semi-solid. Column chromatography (3% MeOH/CHCl$_3$) afforded the desired product as a yellow oil (340 mg, 1.3 mmol, 62% ) 11H NMR (400 MHz, CDCl$_3$) δ 7.50(s, 1H, ArH), 6.63 (s, 1H, ArH), 4.33 (br s, 1H, NH), 4.03 (q, 2H, CH$_2$), 3.60 (t, 2H, N—CH$_2$), 2.70 (t, 2H, CH$_2$), 2.43 (s, 2H, CH$_2$), 1.27 (s, 3H, CH$_3$), 1.25 (s, 3H, CH$_3$), 1.22 (t, 3H, CH$_3$).

Conversion of the tricylic ketone 53 to the title compound 76 followed the procedures given in Examples 1 and 2. TLC (50% EtOAc/hex) afforded the desired 6-(6-ethyl-1,9,9-trimethyl-7-oxo-2,3,6,7,8,9-hexahydro-1H-pyrido [2,3-g] quinolin-4-ylidene)-3-methyl-hexa-2,4-dienoic acid (5 mg) as a red orange film. 1H NMR (400 MHz, CDCl$_3$) δ 7.00 (dd, 1H, CH), 6.84 (s, 1H, ArH), 6.63 (s, 1H, ArH), 6.57 (d, 1H, CH), 6.37 (d, 1H, CH), 5.79 (s, 1H, CH), 3.37 (q, 2H, CH$_2$), 3.20 (t, 2H, N—CH$_2$), 3.10 (t, 2H, CH$_2$), 2.83 (s, 3H, N—CH$_3$), 2.80 (s, 3H, CH$_3$), 2.38 (s, 2H, CH$_2$), 1.35 (s, 6H, CH$_3$), 1.25 (t, 3H, CH$_3$).

EXAMPLE 78

Preparation of Compound 152b According to Scheme XVIII

E-4-[N'-(5,5,8,8-tetramethyl-3,4,5,6,7,8-hexahydro-2H-anthracen-1 -ylidene)-hydrazino]benzoic acid (structure 78, where R$_1$, R$_2$, R$_3$, and R$_4$ are methyl; R$_5$, R$_6$, R$_7$, R$_8$, R$_9$, R$_{10}$, R$_{26}$, R$_{27}$, R$_{28}$ and R$_{29}$ are hydrogen; R$_{15}$ is hydroxy; R$_{14}$ is 4-benzoic acid, W is N, X, Y, Z are carbon; m=n=1).

The title compound was prepared from the tricyclic ketone 60 prepared in Example 1. A solution of 6,6,9,9-tetramethyl-1,2,6,7,8,9-hexahydro-3H-anthracen-1-one (100 mg, 0.39 mmol) and 4-hydrazinobenzoic acid (62.5 mg, 0.41 mmol) and one drop of conc. hydrochloric acid in 5 mL of ethanol was heated to reflux for 3.5 h, then cooled to room temperature. The solvent was removed in vacuo to a solid residue that was subjected to flash chromatography (silica gel, hexanes-ethyl acetate, 70:30) which gave 40 mg (26%) of the desired product 1 as a light yellow solid. The geometry of the hydrazone was determined by NOE experiments. $^1$H NMR (400 MHz, CDCl$_{13}$) δ 8.16 (s, 1H, hydrazone N-H), 8.05 (d, J=8.8 Hz, 2H, benzoic acid-3,4-H's), 7.64 (s, 1H, 10-H), 7.18 (d, J=8.8 Hz, 2H, benzoic acid-1, 5-H's), 7.06 (s, 1H, 5-H), (t, J=6.0 Hz, 2H, 2-CH$_2$), 2.59 (t, J=6.Hz, 2H, 4-CH$_2$), 2.01 (m, 2H, 3-CH$_2$), 1.70 (s, 4H, 7,8-CH$_2$'s), 1.36 (s, 6H), 1.29 (s, 6H).

EXAMPLE 79

Preparation of Compound 153b According to Scheme XVIII

E-4-[N'-(6,6,9,9-tetramethyl-2,3,6,7,8,9-hexahydro-benzo [g]chromen-4-ylidene)-hydrazino]benzoic acid (structure 78, where R$_1$, R$_2$, R$_3$, and R$_4$ are methyl; R$_5$, R$_6$, R$_9$, and R$_{10}$ are hydrogen; R$_{15}$ is hydroxy; R$_{14}$ is para-amino benzoate, G is C, W is N, X, Y, are carbon, Z is O, m=n=1)

A solution of 1,2,3,4-tetrahydro-6,6,9,9-tetramethyl naphto (2,3) pyran-4-one (56 mg, 0.215 mmol) and 4-hydrazinobenzoic acid (50 mg, 0.323 mmol) and one drop of conc. hydrochloric acid in 2 mL of ethanol was heated to reflux for 3.5 h, then cooled to rt. The solvent was removed in vacuo to afford a solid residue that was subjected to flash chromatography (silica gel, hexanes-ethyl acetate, 60:40) to give 1.7 mg (2%) of the desired product 4 as a light yellow solid. $^1$H NMR (400 MHz, CDCl$_3$) δ 8.05 (d, J=7.9 Hz, 2H, benzoic acid-3,4-H's), 8.04 (s, 1H, hydrazone N-H), 7.53 (s, 1H, 5-H), 7.18 (d, J=7.9 Hz, 2H, benzoic acid-1,5-H's), 6.84 (s, 1H, 10-H), 4.30 (t, 2H, J=6.0 Hz, 2-CH$_2$), 2.75 (t, J=6.0 Hz, 2H, 3-CH$_2$), 169 (s, 4H, 7,8-CH$_2$), 1.35 (s, 6H), 1.27 (s, 6H).

EXAMPLE 80

Preparation of Compound 154b According to Scheme XVII (2E,4E)-3-methyl-6-(6-ethyl-1,9,9-trimethyl-2,3,6,9-tetrahydro-1H-pyrido[2,3-g]quinolin-4-ylidene)hexa-2,4-dienoic acid (structure 77, where R$_1$ is ethyl; R$_3$, R$_4$, R$_{19}$ and R$_{24}$ are methyl; R$_5$, R$_7$, R$_8$, R$_9$, R$_{10}$ and R$_{28}$ are hydrogen; R$_{15}$ is hydroxy; X, Z are N; Y is carbon; m=n=1)

The title compound was prepared as a by-product from the synthesis of compound 151b (Example 77). To a solution of 6-ethyl-(1,9,9-trimethyl-7-oxo-2,3,6,7,8,9-hexahydro-1H-pryido [2,3-g]quinolin-4-ylidene)acetonitrile (50 mg, 0.168 mol), in anhydrous toluene (4 ml) and anhydrous hexanes (14 ml) at −78° C. was added DIBAL in hexanes (0.5 ml, 0.5 mol). This mixture was stirred at −30° C. for 3 hours, quenched by slow addition of saturated sodium potassium tatrate, 1 N HCL, and extracted with ethyl acetate. Removal of solvent under reduced pressure afforded a mixture of aldehydes as an red orange oil (50 mg). $^1$ H NMR confirmed the presence of aldehyde protons as well as vinyl protons which correspond to enamine formed by partial reduction of the amide. This material was not purified and used crude in subsequent reactions.

Following the standard procedure demonstrated in Examples 1 and 2, the mixture of aldehydes was carried through to the hydrolysis of the ester products. The crude mixture of esters above was hydrolyzed under standard conditions to give a mixture of trienoic acids. TLC (50% EtOAc/hex) afforded the 6-(6-ethyl-1,9,9-trimethyl-2,3,6,9-tetrahydro-1 H-pyrido [2,3-g]quinolin-4-ylidene)-3-methylhexa-2,4-dienoic acid (4 mg) as a red film: $^1$H NMR (400 MHz, CDCl$_3$) d7.10 (dd, 1H, CH), 6.84 (s, 1H, ArH), 6.72 (s, 1H, ArH), 6.57 (d, 1H, CH), 6.40(d, 1H, CH), 6.00 (d, 1H, CH), 5.82 (s, 1H, CH), 4,42 (d, 1H, CH), 3.25 (q, 2H, CH$_2$), 3.23 (t, 2H, N—CH$_2$), 2.90 (t, 2H, CH$_2$), 2.37 (s, 3H, N—CH$_3$), 2.10 (s, 3H, CH$_3$), 1.38 (s, 3H, CH$_3$), 1.25 (t, 3H, CH$_3$).

Evaluation of Retinoid Receptor Subfamily Activity

Utilizing the "cis-trans" or "co-transfection" assay described by Evans et al., Science, 240:889–95 (May 13, 1988), the disclosure of which is herein incorporated by reference, the retinoid compounds of the present invention were tested and found to have strong, specific activity as either selective RAR agonists, selective RXR agonists, or as pan-agonist activators of both RAR and RXR receptors. This assay is described in further detail in U.S. Pat. Nos. 4,981, 784 and 5,071,773, the disclosures of which are incorporated herein by reference.

The co-transfection assay provides a method for identifying functional agonists which mimic, or antagonists which inhibit, the effect of native hormones, and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds Ln vivo pharmacology. See, e.g., T. Berger et al. 41 J. Steroid Biochem. Molec. Biol. 733 (1992), the disclosure of which is herein incorporated by reference.

In the co-transfection assay, a cloned cDNA for an IR (e.g., human RARα, RARβ, RXRγ) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (co-transfected) into the same cells in conjunction with the IR gene. This second gene, comprising the cDNA for a reporter protein, such as firefly luciferase (LUC), controlled by an appropriate hormone responsive promoter containing a hormone response element (HRE). This reporter plasmid functions as a reporter for the transcription-modulating activity of the target IR. Thus, the reporter acts as a surrogate for the products (mRNA then protein) normally expressed by a gene under control of the target receptor and its native hormone.

The co-transfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. To detect antagonists, the co-transfection assay is carried out in the presence of a constant concentration of an agonist to the target IR (e.g., all-trans retinoic acid for RARα) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activity of the retinoid compounds of the present invention were evaluated utilizing the co-transfection assay according to the following illustrative Example.

EXAMPLE 81

Co-Transfection Assay

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine RAR and/or RXR agonist activity of the compounds of the present invention, the CV-1 cells were transiently transfected by calcium phosphate coprecipitation according to the procedure of Berger et al., 41 *J.Steroid Biochem. Mol. Biol.*, 733 (1992) with the following receptor expressing plasmids: pRShRARα: Giguere et al., 330 *Nature*, 624 (1987); pRShRARβ and pRShRARγ, Ishikawa et al., 4 *Mol. Endocrin.*, 837 (1990); pRShRXRα, Mangelsdorf et al., 345 *Nature*, 224 (1990); and pRSmRXRβ and pRSmRXRγ, Mangelsdorf et al., 6 *Genes & Devel.*, 329 (1992), the disclosures of which are herein incorporated by reference. Each of these receptor expressing plasmids was co-transfected at a concentration of 5 ng/well, along with a basal reporter plasmid at 100 ng/well, the internal control plasmid pRS-β-Gal at 50 ng/well and filler DNA, pGEM at 45 ng/well.

The basal reporter plasmid D-MTV-LUC (Hollenberg and Evans, 55 *Cell*, 899 (1988), the disclosure of which is herein incorporated by reference) containing two copies of the TRE-palindromic response element described in Umesono et al., 336 *Nature*, 262 (1988), the disclosure of which is herein incorporated by reference, was used in transfections for the RARs, and the reporter plasmid CRBPIIFKLUC, which contains an RXRE (retinoid X receptor response element, as described in Mangelsdorf et al., 66 *Cell*, 555 (1991), the disclosure of which is herein incorporated by reference), was used in transfections for the RXRs. Each of these reporter plasmids contains the cDNA for firefly luciferase (LUC) under constitutive promoter containing the appropriate RAR or RXR response element. As noted above, pRS-β-Gal, coding for constitutive expression of *E. coli* β-galactosidase (β-Gal), was included as an internal control for evaluation of transfection efficiency and compound toxicity.

Six hours after transfection, media was removed and the cells were washed with phosphate-buffered saline (PBS). Media containing compounds of the present invention in concentrations ranging from $10^{-12}$ to $10^{-5}$ M were added to the cells. Similarly, the reference compounds all-trans retinoic acid (ATRA)(Sigma Chemical), a known RAR selective compound, and 9-cis retinoic acid (9-cis) (synthesized as described in Heyman et al., *Cell*, 68:397–406 (1992)), a compound with known activity on RXRs, were added at similar concentrations to provide a reference point for analysis of the activity of the compounds of the present invention. Retinoid purity was established as greater than 99% by reverse phase highperformance liquid chromatography. Retinoids were dissolved in dimethylsulfoxide for use in the transcriptional activation assays. Three to four replicates were used for each sample.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

$$\text{LUC response}/\beta\text{-Gal rate}$$

where $\beta$-Gal rate=$\beta$-Gal$\cdot 1\times 10^{-5}/\beta$-Gal incubation time.

The mean and standard error of the mean (SEM) of the NR were calculated. Data was plotted as the response of the compound compared to the reference compounds over the range of the dose-response curve. For the agonist compounds of the present invention, the effective concentration that produced 50% of the maximum response ($EC_{50}$) was quantified.

The potency (nM) of selected retinoid compounds of the present invention are in Table 1 below.

TABLE 1

Potency (nM) of selected retinoid compounds of the present invention on RARα, β, γ and RXRα, β, γ, in comparison to the known RAR-active retinoid compound all-trans retinoic acid (ATRA) and RXR-active retinoid compound 9-cis retinoic acid (9-cis).

| Cmpd. No. | RARα Pot nM | RARβ Pot nM | RARγ Pot nM | RXRα Pot nM | RXRβ Pot nM | RXRγ Pot nM |
|---|---|---|---|---|---|---|
| 101b | 32 | 8 | 7 | 35 | 55 | 41 |
| 104b | na | 61 | 83 | 18 | 20 | 11 |
| 106b | 84 | 20 | 14 | na | 52 | 127 |
| 109b | 28 | 3 | 1 | 2022 | 64 | 2267 |
| 119b | 20 | 1 | 1 | 1659 | 1145 | 742 |
| 124b | 101 | 33 | 94 | 38 | 37 | 26 |
| 135b | 1166 | 53 | 47 | 2783 | 1979 | 2531 |
| 138b | na | na | na | 422 | 204 | 301 |
| 141b | 863 | 32 | 12 | na | na | 2930 |
| 143b | na | 466 | 1877 | 393 | 472 | 247 |
| 144b | 14 | 3 | 2 | 36 | 45 | 40 |
| 147b | 35 | 4 | 1 | na | 579 | 1470 |
| 152b | 651 | 8 | 32 | na | na | na |
| ATRA | 436 | 78 | 19 | 1015 | 1211 | 961 |
| 9-cis | 220 | 29 | 50 | 195 | 128 | 124 | na = not active (potency of >10,000 and/or efficacy of ≦20%)

As can been seen in Table 1, Compounds 101b, 109b, 119b and 144b are extremely potent RAR active, with all compounds displaying activity at less than 10 nM on RARβ and RARγ. Further, Compounds 109b and 119b are RAR selective. In fact, these Compounds are 2 to 10 times more potent than the known RAR active compound ATRA on the RARs. In addition, Compound 104b is a potent and selective RXR compound. Likewise, pan-agonist Compounds 101b, 124b and 144b display superior potency profiles to that of the known RXR active pan-agonist compound 9-cis retinoic acid.

EXAMPLE 82

In addition to the cotransfection data of Example 81,the binding of selected compounds of the present invention to the RAR and RXR receptors was also investigated according to the methodology described in M. F., Boehm, et al., "Synthesis and Structure-Activity Relationships of Novel Retinoid X Receptor Selective Retinoids", 37 *J. Med. Chem.*, 2930 (1994); M. F. Boehm, et al., "Synthesis of High Specific Activity [$^3$H]-9-cis Retinoic Acid and Its Application for Identifying Retinoids with Unusual Binding Properties", 37 *J. Med. Chem.*, 408 (1994), and E. A. Allegretto, et al., "Characterization and Comparison of Hormone-Binding and Transactivation Properties of Retinoic Acid and Retinoid X Receptors Expressed in Mammalian Cells and Yeast", 268 *J. Biol. Chem.*, 22625 (1993), the disclosures of which are herein incorporated by reference.

Non-specific binding was defined as that binding remaining in the presence of 500 nM of the appropriate unlabelled compound. At the end of the incubation period, bound from free ligand were separated. The amount of bound tritiated retinoids was determined by liquid scintillation counting of an aliquot (700 mL) of the supernatant fluid or the hydroxylapatite pellet.

After correcting for non-specific binding, $IC_{50}$ values were determined. The $IC_{50}$ value is defined as the concentration of competing ligand needed to reduce specific binding by 50%. The $IC_{50}$ value was determined graphically from a log-logit plot of the data. The $K_i$ values were determined by application of the Cheng-Prussof equation to the $IC_{50}$ values, the labeled ligand concentration and the $K_d$ of the labeled ligand.

The binding activity (Kd in nM) results of selected retinoid compounds of present invention, and the reference compounds ATRA, and 9-cis RA, is shown in Table 2 below.

EXAMPLE 83

Yet another recognized measure of the retinoid activity of the compounds of the present invention is the ornithine decarboxylase assay, as originally described by Verma and Boutwell, 37 *Cancer Research,* 2196 (1977), the disclosure of which is herein incorporated by reference. In Verma & Boutwell original work using retinoic acid, it was established that ornithine decarboxylase (ODC) activity increased in relation to polyamine biosynthesis. In turn, it had previously been established that increases in polyamine biosynthesis is correlated with cellular proliferation. Thus, if ODC activity could be inhibited, cell hyperproliferation could be modulated. Although all causes of increased OCD activity are yet unknown, it is known that 12-O-tetradecanoylphorbor-13-acetate (TPA) induces ODC activity. Importantly, retinoic acid inhibits this induction of ODC by TPA.

An ODC assay essentially following the procedures set out in 35 *Cancer Research,* 1662 (1975), the disclosure of which is herein incorporated by reference, was used to demonstrate the inhibition of TPA induction of ODC by the compounds of the present invention. The results of this assay on exemplary compounds, and the reference compounds ATRA and (E)-4-[2-(5,6,7,8-tetrahydro-5,5,8,8-tetramethyl-2-napthalenyl)-1-propenyl]benzoic acid (TTNPB), known RAR active compounds, are shown below in Table 3. All values are expressed as the concentration of the indicated compounds in nM required to inhibit the TPA induction of ODC by $^{80}$ percent, i.e., the $IC_{80}$ in nM.

TABLE 3

Inhibitory concentration required to inhibit 80% of the maximally observed TPA induction of ODC (ODC $IC_{80}$) in nM for selected Compounds of the present invention and reference compounds ATRA and TTNBP.

| Compound | ODC $IC_{80}$ (nM) |
| --- | --- |
| 101a | 91.0 |
| 101b | 0.78 |
| 109b | 0.08 |
| 144b | 0.60 |
| ATRA | 1.40 |
| TTNPB | 0.09 |

TABLE 2

Binding (Kd in nM) of selected retinoid compounds of the present invention on RARα, β, γ and RXRα, β, γ proteins in comparison to the known RAR-active retinoid compound all-trans retinoic acid (ATRA) and RXR-active retinoid compound 9-cis retinoic acid (9-cis).

| Cmpd. No. | RARα Binding Kd (nM) | RARβ Binding Kd (nM) | RARγ Binding Kd (nM) | RXRα Binding Kd (nM) | RXRβ Binding Kd (nM) | RXRγ Binding Kd (nM) |
| --- | --- | --- | --- | --- | --- | --- |
| 101b | 225 | 299 | 541 | 34 | 30 | 48 |
| 109b | 33 | 68 | 279 | 340 | 332 | 382 |
| 119b | 24 | 50 | 87 | 246 | 372 | 398 |
| 138b | >1000 | >1000 | >1000 | 136 | 276 | 508 |
| 144b | 145 | 313 | 494 | 59 | 146 | 85 |
| 147b | 6 | 4 | 8 | 433 | 548 | 724 |
| ATRA | 15 | 17 | 17 | 53 | 306 | 306 |
| 9-cis | 93 | 97 | 148 | 8 | 15 | 14 |

As can be seen in Table 2, the compounds of the present invention show comparable binding to the known RAR active compound ATRA, and the known RXR active compound 9-cis.

Compound 101b, which is the ester of Compound 101a, has been included to show that such ester analogs exhibit retinoid activity. While not being bound to a theory of operation, it is believed that such esters may operate as pro-drugs in vivo, possibly due to the cleavage of the ester to the active acid form of the compounds of the present invention.

EXAMPLE 84

The in vitro affect of selected compounds of the present invention on the recognized cancer cell lines, RPMI 8226, ME 180 and AML-193, obtained from the American Type Culture Collection (ATCC, Rockville, Md.), was investigated.

RPMI 8226 is a human hematopoietic cell line obtained from the peripheral blood of a patient with multiple myeloma, and as such is a recognized model for multiple myelomas and related malignancies. Y. Matsuoka, G. E. Moore, Y. Yagi and D. Pressman, "Production of free light chains of immunoglobulin by a hematopoietic cell line derived from a patient with multiple myeloma", 125 *Proc. Soc. Exp. Biol. Med.,* 1246 (1967), the disclosure of which is herein incorporated by reference. The cells resemble the lymphoblastoid cells of other human lymphocyte cell lines and secretes λ-type light chains of immunoglobulin. RPMI 8226 cells were grown in RPMI medium (Gibco) supplemented with 10% fetal bovine serum, glutamine and antibiotics. The cells were maintained as suspension cultures grown at 37° C. in a humidified atmosphere of 5% $CO_2$ in air. The cells were diluted to a concentration of $1 \times 10^5$/mL twice a week.

ME 180 is a human epidermoid carcinoma cell line derived from the cervix, and as such is a recognized model for squamous cell carcinomas and related malignancies. J. A. Sykes, J. Whitescarver, P. Jemstrom, J. F. Nolan and P. Byatt, "Some properties of a new epithelial cell line of human origin", 45 MH-Adenoviridae *J. Natl. Cancer Inst.,* 107 (1970), the disclosure of which is herein incorporated by reference. The tumor was a highly invasive squamous cell carcinoma with irregular cell clusters and no significant keratinization. ME 180 cells were grown and maintained in McCoy's 5a medium (Gibco) supplemented with 10% fetal bovine serum, glutamine and antibiotics. The cells were maintained as monolayer cultures grown at 37° C. in a humidified atmosphere of 5% $CO_2$ in air.

The AML-193 cell line was established from the blast cells of a patient with leukemia and was classified as M5 Acute Monocytic Leukemia, and as such is a recognized model for leukemias and related malignancies. G. Rovera, et al., 139 *J. Immunol.,* 3348 (1987), the disclosure of which is herein incorporated by reference. Over 75% of these cells are positive by immunofluorescence for the myelomonocytic antigen CS15. The cells were grown in Iscove's modified Dulbeccos's medium with 5 μg/mL transferring, 5 μg/mL insulin and 2 ng/mL rh GM-CSF. The cells were maintained as suspension cultures grown at 37° C. in a humidified atmosphere of 5% $CO_2$ in air. The cells were diluted to a concentration of $1 \times 10^5$/mL twice a week.

Incorporation of $^3$H-Thymidine

Measurement of the level of radiolabeled thymidine incorporated into the above-identified cell lines provides a direct measurement of the antiproliferative properties of the compounds of the present invention. The method used for determination of the incorporation of radiolabeled thymidine was adapted from the procedure described by S. Shrivastav et al., "An in vitro assay procedure to test chemotherapeutic drugs on cells from human solid tumors", 40 *Cancer Res.,* 4438 (1980), the disclosure of which is herein incorporated by reference. RPMI 8226 or AML-193 cells were plated in a 96 well round bottom microtiter plate (Costar) at a density of 1,000 cells/well. To appropriate wells, retinoid test compounds were added at the final concentrations indicated for a final volume of 150 μL/well. The plates were incubated for 96 hours at 37° C. in a humidified atmosphere of 5% $CO_2$ in air. Subsequently, 1 μCi of [5'-$^3$H]-thymidine (Amersham, U.K, 43 Ci/mmol specific activity) in 25 μL culture medium was added to each well and the cells were incubated for an additional six hours. The cultures were further processed as described below.

ME 180 cells, harvested by trypsinization were plated in a 96 well flat bottom microtiter plate (Costar) at a density of 2,000 cells/well. The cultures were treated as described above for RPMI 8226 with the following exceptions. After incubation, the supernatant was carefully removed, and the cells were washed with a 0.5 mM solution of thymidine in phosphate buffered saline. ME 180 cells were briefly treated with 50 μL of 2.5% trypsin to dislodge the cells from the plate. Both cell lines were then processed as follows: the cellular DNA was precipitated with 10% trichloroacetic acid onto glass fiber filter mats using a SKATRON multi-well cell harvester (Skatron Instruments, Sterling Va.). Radioactivity incorporated into DNA, as a direct measurement of cell growth, was measured by liquid scintillation counting. The mean disintegrations per minute of incorporated thymidine from triplicate wells was determined. The $IC_{50}$ (nM concentration required to inhibit 50% of the maximally observed incorporation of thymidine) for Compounds 101b, 104b, 109b, 119b and 144b of the present invention, and reference compounds ATRA and TTNBP are shown below in Tables 4, 5 and 6 for the cell lines RPMI 8226, ME 180 and AML-193 respectively.

Viability

Selected compounds of the present invention were also measured to determine their cytotoxicity on the above-identified cell lines. The procedure used was identical, with only slight modifications, to the assay described in T. Mosmann, "Rapid calorimetric assay for cellular growth and survival: application to proliferation and cytotoxicity assays", 65 *J. Immunol. Meth.,* 55 (1983), the disclosure of which is herein incorporated by reference. RPMI 8226 or AML-193 cells were plated in a 96 well round bottom microtiter plate (Costar) at a density of 1,000 cells/well. To appropriate wells, retinoid test compounds were added at the final concentrations indicated for a final volume of 150 μL/well. The plates were incubated for 96 hours at 37° C. in a humidified atmosphere of 5% $CO_2$ in air. Subsequently, 15 μL of a filter sterilized tetrazolium dye in phosphate buffered saline (Promega, Madison, Wis.) was added to each well and the cells were incubated for an additional four hours. Subsequent manipulations of the cultures were as described below.

ME 180 cells, harvested by trypsinization were plated in a 96 well flat bottom microtiter plate (Costar) at a density of 2,000 cells/well. The cultures were treated as described above for RPMI 8226.

After the four hours incubation, 100 μL of a solubilization/stop solution was added to each well (Promega, Madison, Wis.). The plates were allowed to stand overnight at 37 ° C in the humidified atmosphere. The absorbance at 570–600 nm wavelength was recorded for each well using a Biomek ELISA plate reader (Beckman Instruments). The $IC_{50}$ (nM concentration required to inhibit 50% of the mitochondrial function, and ultimately, the viability of the cells) for Compounds 101b, 104b, 109b, 119b and 144b of the present invention, and reference compounds ATRA and TTNBP are also shown below in Table 4, 5 and 6 for the cell lines RPMI 8226, ME 180 and AML-193 respectively.

TABLE 4

Inhibitory concentration required to inhibit 50% of the maximally observed radiolabeled thymidine (TdR $IC_{50}$) in nM, and inhibitory concentration required to inhibit 50% of the mitochondrial function (MTS $IC_{50}$) in nM, for selected Compounds of the present invention and reference compounds ATRA and TTNBP on the RPMI 8226 cell line.

| Compound | TdR $IC_{50}$ (nM) | MTS $IC_{50}$ (nM) |
| --- | --- | --- |
| 101b | 6 | 100 |
| 104b | 30 | 90 |
| 109b | 0.05 | 10 |
| 119b | 0.5 | 2.6 |
| 144b | 0.6 | 7.5 |
| ATRA | 102 | 756 |
| TTNPB | 0.2 | 10 |

TABLE 5

Inhibitory concentration required to inhibit 50% of the maximally observed radiolabeled thymidine (TdR $IC_{50}$) in nM, and inhibitory concentration required to inhibit 50% of the mitochondrial function (MTS $IC_{50}$) in nM, for selected Compounds of the present invention and reference compounds ATRA and TTNBP on the ME 180 cell line.

| Compound | TdR $IC_{50}$ (nM) | MTS $IC_{50}$ (nM) |
| --- | --- | --- |
| 101b | 8 | 75 |
| 104b | 90 | 1000 |
| 109b | 5 | 100 |
| 119b | 0.6 | 2 |
| 144b | 4 | 10 |
| ATRA | 253 | 890 |
| TTNPB | 0.4 | 187 |

TABLE 6

Inhibitory concentration required to inhibit 50% of the maximally observed radiolabeled thymidine (TdR $IC_{50}$) in nM, and inhibitory concentration required to inhibit 50% of the mitochondrial function (MTS $IC_{50}$) in nM, for selected Compounds of the present invention and reference compounds ATRA and TTNBP on the AML-193 cell line.

| Compound | TdR $IC_{50}$ (nM) | MTS $IC_{50}$ (nM) |
| --- | --- | --- |
| 101b | 37 | 1000 |
| 104b | 90 | 1000 |
| 109b | 500 | 1000 |
| 119b | 0.6 | 1000 |
| 144b | 0.6 | 1000 |
| ATRA | 197 | 1000 |
| TTNPB | 0.1 | 1000 |

EXAMPLE 85

The following examples provide illustrative pharmacological composition formulations:

Hard gelatin capsules are prepared using the following ingredients:

| | Quantity (mg/capsule) |
| --- | --- |
| Compound 101b | 140 |
| Starch, dried | 100 |
| Magnesium stearate | 10 |
| Total | 250 mg |

The above ingredients are mixed and filled into hard gelatin capsules in 250 mg quantities.

A tablet is prepared using the ingredients below:

| | Quantity (mg/tablet) |
| --- | --- |
| Compound 101b | 140 |
| Cellulose, microcrystalline | 200 |
| Silicon dioxide, fumed | 10 |
| Stearic acid | 10 |
| Total | 360 mg |

The components are blended and compressed to form tablets each weighing 360 mg.

Tablets, each containing 60 mg of active ingredient, are made as follows:

| | Quantity (mg/tablet) |
| --- | --- |
| Compound 101b | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, are then added to the granules which, after mixing, are compressed on a tablet machine to yield tablets each weighing 150 mg.

Suppositories, each containing 225 mg of active ingredient, may be made as follows:

| | |
| --- | --- |
| Compound 101b | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

| | |
|---|---|
| Compound 101b | 100 mg |
| Isotonic saline | 1,000 ml |
| Glycerol | 100 ml |

The compound is dissolved in the glycerol and then the solution is slowly diluted with isotonic saline. The solution of the above ingredients is then administered intravenously at a rate of 1 ml per minute to a patient.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A tricyclic compound of the formula:

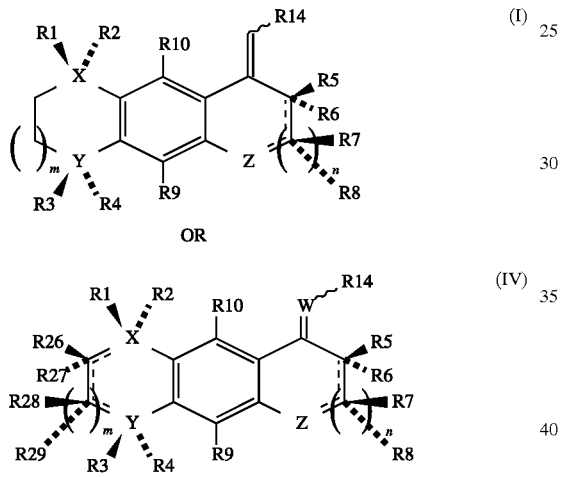

wherein, $R_1$ through $R_4$ each independently are hydrogen, a $C_1$–$C_6$ alkyl, or a $C_7$–$C_{15}$ arylalkyl;

$R_5$ and $R_8$ each independently are hydrogen, a $C_1$–$C_6$ alkyl, or at least two of $R_5$ through $R_8$ taken together are a $C_3$–$C_6$ cycloalkyl;

$R_9$ and $R_{10}$ each independently are hydrogen, a $C_1$–$C_6$ alkyl, F, Cl, Br, $NR_{11}R_{12}$, $NO_2$ or $OR_{13}$, where $R_{11}$ and $R_{12}$ each independently are hydrogen, a $C_1$–$C_8$ alkyl, a $C_7$–$C_{15}$ arylalkyl, a $C_1$–$C_8$ acyl, provided that only one of $R_{11}$ or $R_{12}$ can be acyl, or $R_{11}$ and $R_{12}$ taken together are a $C_3$–$C_6$ cycloalkyl, and where $R_{13}$ is hydrogen or a $C_1$–$C_8$ alkyl or a $C_7$–$C_{15}$ arylalkyl;

$R_{14}$ represents:

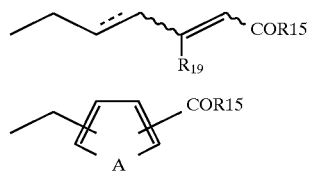

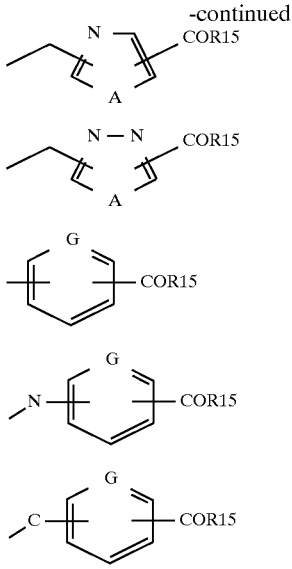

where $R_{15}$ is $OR_{16}$ or $NR_{17}R_{18}$, with $R_{16}$ being hydrogen, a $C_1$–$C_6$ alkyl or a $C_7$–$C_{15}$ arylalkyl, and with $R_{17}$ and $R_{18}$ each independently being hydrogen, a $C_1$–$C_6$ alkyl, a $C_7$–$C_{15}$ arylalkyl, aryl, ortho-, meta-, or para-substituted hydroxyaryl, or taken together are a $C_3$–$C_6$ cycloalkyl, provided that $R_{18}$ must be hydrogen when $R_{17}$ is aryl or hydroxyaryl, $R_{19}$ is a $C_1$–$C_5$ alkyl, and A is O, S or $NR_{20}$, where $R_{20}$ is a hydrogen, $C_1$–$C_6$ alkyl or a $C_7$–$C_{15}$ arylalkyl;

$R_{26}$ through $R_{29}$ each independently are hydrogen or a $C_1$–$C_6$ alkyl, or taken together then one each of $R_{26}$ and $R_{27}$ or $R_{28}$ and $R_{29}$ respectively, form a carbonyl group;

X and Y each independently represent C, O, S, N, SO, or $SO_2$, provided, however, that when X or Y are O, S, SO or $SO_2$, then either $R_1$ and $R_2$ or $R_3$ and $R_4$ respectively do not exist, and further provided, that when X or Y is N, then one each of $R_1$ and $R_2$ or $R_3$ and $R_4$ respetively, do not exist;

Z is O, S, CR, $CR_{22}R_{23}$ or $NR_{24}$, where $R_{22}$ through $R_{24}$ each independently are hydrogen or a $C_1$–$C_6$ alkyl or $R_{22}$ and $R_{23}$ taken together are a $C_3$–$C_6$ cycloalkyl;

W is N or $CR_{25}$, where $R_{25}$ is hydrogen or a $C_1$–$C_6$ alkyl;

G is C or N, provided G cannot be C when W is C;

m is 0 or 1 carbon atoms;

n is 0, 1 or 2 carbon atoms;

the dashed lines in the structures represent optional double bonds, provided, however, that the double bonds cannot be contiguous, and further provided that when such optional double bonds exist then one each of $R_5$ and $R_6$ or $R_7$ and $R_8$ respectively do not exist; and the wavy lines represent olefin bonds that are either in the cis (Z) or trans (E) configuration.

2. A compound according to claim 1, selected from the group consisting of ethyl (2E,4E)-3-methyl-6-[(Z)-3,4,5,6,7,8-hexahydro-5,5,8,8-tetramethyl-2H-anthracen-1-ylidene]hexa-2,4-dienoate; (2E,4E)-3-methyl-6-[(Z)-3,4,5,6,7,8-hexahydro-5,5,8,8-tetramethyl-2H-anthracen-1-ylidene]hexa-2,4-dienoic acid; ethyl (2E,4E)-3-methyl-6-[(Z)-2,3–5,6,7,8-hexahydro-5,5,8,8-tetramethylcyclopenta[b]napthalen-1-ylidene[hexa-2,4-dienoate; (2E,4E)-3-methyl-6-[(Z)-2,3–5,6,7,8-hexahydro-5,5,8,8-tetramethyl-cycopenta[b]naphthalen-1-ylidene]hexa-2,4-dienoic acid; ethyl (2E,4E)-3-methyl-6-[(Z)-1,2,3,6,7,8-heptahydro-1,1, 3,3-tetramethylcyclopenta[b]napthalen-5-ylidene]hexa-2,4-dienoate; (2E,4E)-3-methyl-6-[(Z)-1,2,3,6,7,8-hexahydro-1,1,3,3-tetra-cyclopenta[b]naphthalen-5-ylidene]hexa-2,4-dienoic acid; (2E,4E)-3-methyl-6-(2,3,6,7,8,9-hexahydro-2,2,6,6,9,9-hexamethylbenzo[b]-chromen-4-ylidene)hexa-2,4-dienoic acid; ethyl (2E,4E)-3-methyl-6-[(Z)-3,4,5,6,7-hexahydro-10-nitro-5,5,8,8-tetramethyl-2H-anthracen-1-ylidene]hexa-2,4-dienoate; (2E,4E)-3methyl-6-[(Z)-3,4,5,6,7,8-hexahydro-10-nitro-5,5,8,8-tetramethyl-2H-anthracen-1-ylidene]hexa-2,4-dienoic acid; ethyl (2E,4E)-3-methyl-6-[(Z)-3,4,5,6,7,8-hexahydro-4,4,5,5,8,8-hexamethyl-2H-anthracen-1-ylidene]hexa-2,4-dienoate; (2E,4E)-3-methyl-6-[(Z)-3,4,5,6,7,8-hexahydro-4,4,5,5,8,8-hexamethyl-2H-anthracen-1-ylidene]hexa-2,4-dienoic acid; (2E,4E)-3-methyl-6-[(Z)-2,3,5,6,7,8-hexahydro-3,5,5,8,8-pentamethyl-cyclopenta[b]naphthalen-1-ylidene]hexa-2,4-dienoic acid; (2E,4E)-3-methyl-6-[(Z)-3,5,6,7-tetrahydro-5,5,7,7-tetramethyl-2H-5-indacen-1-ylidene]hexa-2,4-dienoic acid; ethyl (2E,4E)-3methyl-6-(E)-3,4,5,6,7,8-hexahydro-5,5,8,8-tetramethyl-2H-anthracen-1-ylidene]hexa-2,4-dienoate; (2E,4E)-3-methyl-6-[(E)-3,4,5,6,7,8-hexahydro-5,5,8,8-tetramethyl-2H-anthracen-1-ylidene]hexa-2,4-dienoic acid; ethyl (2E,4E)-3-methyl-6-[(E)-2,3,5,6,7,8-hexahydro-5,5,8,8-tetramethylcyclopenta[b]naphthalen-1-yliden]hexa-2,4-dienoate; (2E,4E)-3-methyl-6-[(E)-2,3,5,6,7,8-hexahydro-5,5,8,8-tetramethylcyclopenta[b]naphthalen-1-ylidene]hexa-2,4-dienoic acid; ethyl (2E,4E)-3-methyl-6-[(E)-1,2,3,6,7,8-hexahydro-1,1,3,3-tetramethylcyclopenta[b]naphthalen-5-ylidene]hexa-2,4-dienoate; (2E,4E)-3-methyl-6[(E)-1,2,3,6,7,8-hexahydro-1,1,3,3-tetramethylcyclopenta[b]-5-ylidene]hexa-2,4-dienoic acid; ethyl (2Z,4E)-3-methy-6-[(E)-1,2,3,6,7,8-hexahydro-1,1,3,3-tetramethylcyclopenta[b]naphthalen-5-ylidene]hexa-2,4-dienoate; (2Z,4E)-3-methyl-6-[(E)-1,2,3,6,7,8-hexahydro-1,1,3,3-tetramethylcyclopenta[b]naphthalen-5-ylidene]hexa-2,4-dienoic acid; (2E,4E)-3-methyl-6-(E)-[4,4,6,6,9,9-hexamethyl-1,2,3,4,5,6,7,8-octahyroanthracen-1-ylidene]hexa-2,4-dienoic acid; ethyl (2E,4E,6E)-3-methyl-6-[1,2,3,4,7,8,9,10-octahydro-1,1,4,4-tetramethyl-6H-naphthocycloheptene-10-yl]hexa-2,4,6-trienoate; ethyl (2Z,4E,6E)-3-methyl-6-[1,2,3,4,7,8,9,10-octahydro-1,1,4,4-tetramethyl-6H-naphthocyclohepten-10-yl]hexa-2,4,6-trienoate; ethyl (2Z,4E)-3-methyl-6-[1,2,3,4,7,8,9,10-octahydro-1,1,4,4-tetramethyl-6H-naphthocycloheptene-10-yl]hexa-2,4,6-trienoate; (2E,4E)-3-methyl-6-[1,2,3,4,7,8,9,10-octahydro-1,1,4,4-tetramethyl-6H-naphthocycloheptene-10-yl]hexa-2,4,6-trienoic acid; (2E,4E)-3-methyl-6-[(E)-3,5,6,7-tetrahydro-5,5,7,7-tetramethyl2H-5-indacen-1-ylidene]hexa-2,4-dienoic acid; ethyl (2E,4E)-3-methyl-6-[(E)-3,4,5,6,7,8-hexahydro-10-nitro-5,5,8,8-tetramethyl-2H-anthracen-1-ylidene]hexa-2,4-dienoate; (2E,4E)-3-methyl-6-[(E)-5,3,4,5,6,7,8-hexahydro-10-nitro-5,5,8,8-tetrameth-2H-anthracen-1-ylidene]hexa-2,4-dienoci acid; (2E,4E)-3-methyl-6-[(E)2,3,6,7,8,9-hexahydro-6,6,9,9-tetramethylbenzo[g]chromen-4-ylidene]hexa-2,4-dienoic acid; (2Z,4E)-3-methyl-6[(E)2,3,6,7,8,9,heahydro-6,6,9,9-tetramrthylbenzo[g]chromen-4-yliden[hexa-2,4-dienoic acid; (2E,4E)-3-methyl-6-[(E)-3,6,7,8,9-hexahydro-6,6,9,9-tetramethylbenzo[g]chromen-4-ylidene[hexa-2,4-dienoic acid; (2E,4E)-3-methyl-6-(1,2,3,4,7,8,9,10-octahydro-7,7,10,10-tetramethylbenzo[f]quinolin-4-yl)hexa-2,4-dienoic acid;(2E,4E)-3-methyl-6-[(Z)-5,6,7,8-tetrahydro-5,5,8,8-tetramethylnaphthy(2,3-b-pyran-4-ylidene]hexa-2,4-dienoic acid; (2E,4E)-3-methyl-6-[(E)-3,4,5,6,7,8-hexahydro-2,2,5,5,8,8-hexamethyl-2H-anthracen-1-ylidene]hexa-2,4-dinoic acid; Ethyl-(2E,4E)-3-methyl-6-[(Z)-N-acetyl-3,4,5,6,7,8,-hexahydro-10-amino-5,5,8,8-tetramethyl-2H-anthracen-1-ylidene[hexa-2,4-dienoate; (2E,4E)-3-methyl-6-[(Z)-N-acetyl-3,4,5,6,7,8-hexahydro-10-amino-5,5,8,8-tetramethyl-2H-anthracen-1-ylidene] hexa-2,4-dienoic acid; (2E,4E)-3-methyl-6-[(E)1-ethyl-6,6,9,9-tetramethyl-2,3,6,7,8,9-hexahydro-1H-benzo[g] quinolin-4-ylidene]hexa-2,4-dienoic acid; T-butyl-4-(5-carboxy-penta-2E-4E-dieneylidene)-6,6,9,9-tetramethyl-3,4,6,7,8,9-hexahydro-2H-benzo[g]quinolin-1-carboxylate; (2E,4E)-3-mehtyl-6-(6-ethyl-1,9,9-trimethyl-7-oxo-2,3,6,7,8,9-hexahydro-1H-pyrido[2,3-g]quinolin-4-ylidene)hexa-2,4-dienoic acid; E-4-[N'-(5,5,8,8-tetramethyl-3,4,5,6,7,8-hexahydro-2H-anthracen-1-ylidene)-hydrazino]benzoic acid; E-4-[N'-(6,6,9,9-tetramethyl-2,3,6,7,8,9-hexahydro-benzo[g]chromen-4-ylidene)-hydrazino]benzoic acid and (2E,4E)-3-mehtyl-6-(6-ethyl-1,9,9-trimethyl-2,3,6,9,-tetrahydro-1H-pyrido[2,3-g]quinolin-4-ylidene)hexa-2,4-dienoic acid.

3. A compound according to claim 1, wherein the compound has retinoid activity.

4. A compound according to claim 3, wherein the compound exhibits 50% maximal activation of one or more retinoid receptors at a concentration of less than 100 nM.

5. A compound according to claim 3, wherein the compound exhibits 50% maximal activation of one or more retinoid receptors at a concentration of less than 50 nM.

6. A compound according to claim 3, wherein the compound exhibits 50% maximal activation of one or more retinoid receptors at a concentration of less than 20 nM.

7. A compound according to claim 3, wherein the compound exhibits 50% maximal activation of one or more retinoid receptors at a concentration of less than 10 nM.

8. A compound according to claim 3, wherein the compound exhibits activity as a selective RAR agonist.

9. A compound according to claim 8, wherein the compound is at least two times more potent an activator of RAR than of RXR.

10. A compound according to claim 8, wherein the compound is at least five times more potent an activator of RAR than of RXR.

11. A compound according to claim 8, wherein the compound is at least ten times more potent an activator of RAR than of RXR.

12. A compound according to claim 8, wherein the compound is at least one hundred times more potent an activator of RAR than of RXR.

13. A compound according to claim 3, wherein the compound exhibits activity as a selective RXR agonist.

14. A compound according to claim 13, wherein the compound is at least two times more potent an activator of RXR than of RAR.

15. A compound according to claim 13, wherein the compound is at least five times more potent an activator of RXR than of RAR.

16. A compound according to claim 13, wherein the compound is at least ten times more potent an activator of RXR than of RAR.

17. A compound according to claim 13, wherein the compound is at least one hundred times more potent an activator of RXR than of RAR.

18. A compound according to claim 3, wherein the compound exhibits activity as both an activator of RAR and RXR.

19. A compound according to claim 1, for administiation to a patient at a dosage of from about 1 μg/kg of body weight to about 500 mg/kg of body weight.

20. A compound according to claim 1, for administiation to a patient at a dosage of from about 10 μg/kg of body weight to about 250 mg/kg of body weight.

21. A compound according to claim 1, for administration to a patient at a dosage of from about 20 µg/kg of body weight to about 100 mg/kg of body weight.

22. A compound according to claim 3, wherein the compound is effective in treating skin-related diseases and conditions, cancerous and pre-cancerous conditions, diseases of the eye, cardiovascular diseases, inflammatory diseases, neurodegenerative diseases, diseases involving modulation of apoptosis, diseases of the immune system, improper pituitary function, diseases involving human papilloma virus, wound healing or restoration of hair growth.

23. A pharmaceutical composition comprising a compound of claim 1 and a pharmaceutically acceptable carrier.

24. A pharmaceutical composition according to claim 23, wherein the composition is formulated for oral, topical, intravenous, suppository or parental administration.

25. A pharmaceutical composition according to claim 23, for administration to a patient at a dosage of from about 1 µg/kg of body weight to about 500 mg/kg of body weight.

26. A pharmaceutical composition according to claim 23, for administration to a patient at a dosage of from about 10 µg/kg of body weight to about 250 mg/kg of body weight.

27. A pharmaceutical composition according to claim 23, for administration to a patient at a dosage of from about 20 µg/kg of body weight to about 100 mg/kg of body weight.

28. A pharmaceutical composition according to claim 23, wherein the composition is effective in treating skin-related diseases and conditions, cancerous and pre-cancerous conditions, diseases of the eye, cardiovascular diseases, inflammatory diseases, neurodegenerative diseases, diseases involving modulation of apoptosis, diseases of the immune system, improper pituitary function, diseases involving human papilloma virus, wound healing or restoration of hair growth.

29. A pharmaceutical composition according to claim 23, wherein the composition exhibits activity as a selective RAR or RXR agonist.

30. A pharmaceutical composition according to claim 23, wherein the composition exhibits activity as both an activator of RAR and RXR.

31. A method of affecting RAR and/or RXR activity comprising the in vivo administration of a compound according to claim 3.

32. A method of modulating processes mediated by RAR and/or RXR receptors comprising administering to a patient an amount of a compound according to claim 3, said amount being effective to modulate one or more processed mediated by RAR and/or RXR receptors.

33. A method of treating a patient requiring retinoid therapy comprising administering to the patient a pharmaceutically effective amount of a compound according to claim 3.

34. A method of treating a patient according to claim 33, wherein the compound is effective in treating skin-related diseases and conditions, cancerous and pre-cancerous conditions, diseases of the eye, cardiovascular diseases, inflammatory diseases, neurodegenerative diseases, diseases involving modulation of apoptosis, diseases of the immune system, improper pituitary function, diseases involving human papilloma virus, wound healing or restoration of hair growth.

35. A method of treating a patient requiring retinoid therapy comprising administering to the patient a pharmaceutically effective amount of a pharmaceutical composition according to claim 23.

36. A method of treating a patient according to claim 35, wherein the composition is effective in treating skin-related diseases and conditions, cancerous and pre-cancerous conditions, diseases of the eye, cardiovascular diseases, inflammatory diseases, neurodegenerative diseases, diseases involving modulation of apoptosis, diseases of the immune system, improper pituitary function, diseases involving human papilloma virus, wound healing or restoration of hair growth.

37. A method for determining the presence of one or more RAR and/or RXR receptors in a sample comprising combining a compound according to claim 1 with the sample and detecting the presence of any complexes of the compound bound to a receptor in the sample, wherein the presence of one or more RAR and/or RXR receptors in the sample is determined by the presence of said complexes.

38. A ligand-retinoid receptor complex formed by the binding of a compound according to claim 1 to a RAR and/or RXR receptor.

39. A method of purifying retinoid receptors comprising combining a compound according to claim 1 with a sample containing RAR and/or RXR receptors, allowing said compound to bind said receptors, and separating out the bound combination of said compound and said RAR and/or RXR receptors.

* * * * *